US011474106B2

(12) United States Patent
Henderson et al.

(10) Patent No.: US 11,474,106 B2
(45) Date of Patent: Oct. 18, 2022

(54) METHODS FOR CYTOTOXIC CHEMOTHERAPY-BASED PREDICTIVE ASSAYS

(71) Applicants: ACCELERATED MEDICAL DIAGNOSTICS, INC., Berkeley, CA (US); LAWRENCE LIVERMORE NATIONAL SECURITY, LLC, Livermore, CA (US); THE REGENTS OF THE UNIVERSITY OF CALIFORNIA, Oakland, CA (US)

(72) Inventors: Paul Henderson, Berkeley, CA (US); George D. Cimino, Lafayette, CA (US); Chong-Xian Pan, Davis, CA (US); Ralph William de Vere White, Sacramento, CA (US); Maike Zimmermann, Davis, CA (US); Kenneth W. Turteltaub, Livermore, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 443 days.

(21) Appl. No.: 15/742,454

(22) PCT Filed: Jul. 7, 2016

(86) PCT No.: PCT/US2016/041382
§ 371 (c)(1),
(2) Date: Jan. 5, 2018

(87) PCT Pub. No.: WO2017/007961
PCT Pub. Date: Jan. 12, 2017

(65) Prior Publication Data
US 2018/0209984 A1    Jul. 26, 2018

Related U.S. Application Data

(60) Provisional application No. 62/190,002, filed on Jul. 8, 2015.

(51) Int. Cl.
*G01N 33/574*  (2006.01)
*G01N 33/53*   (2006.01)
(Continued)

(52) U.S. Cl.
CPC ....... *G01N 33/57484* (2013.01); *A61K 31/28* (2013.01); *A61K 31/395* (2013.01);
(Continued)

(58) Field of Classification Search
CPC ......... G01N 33/5308; G01N 33/57484; G01N 33/60
See application file for complete search history.

(56) References Cited

U.S. PATENT DOCUMENTS 4,411,881 A   10/1983  Tzodikov
5,561,064 A   10/1996  Marquet et al.
(Continued)

FOREIGN PATENT DOCUMENTS

CA        2779843 A1      5/2011
WO    WO 2001/010468 A2   2/2001
(Continued)

OTHER PUBLICATIONS

Hah (Chem Res Toxicol 2006 vol. 19 pp. 622-626).*
(Continued)

*Primary Examiner* — Diana B Johannsen
(74) *Attorney, Agent, or Firm* — Goodwin Procter LLP

(57) ABSTRACT

The invention relates to methods, systems and kits for determining therapeutic effectiveness or toxicity of cancer-treating compounds that incorporate into or bind to DNA. In particular, the invention is directed to methods, systems and
(Continued)

kits for predicting a patient's treatment outcome after administration of a microdose of therapeutic composition to the patient. The methods provides physicians with a diagnostic tool to segregate cancer patients into differential populations that have a higher or lower chance of responding to a particular therapeutic treatment.

11 Claims, 30 Drawing Sheets

(51) Int. Cl.
| | |
|---|---|
| G01N 33/60 | (2006.01) |
| A61K 31/555 | (2006.01) |
| A61K 31/7068 | (2006.01) |
| A61K 33/243 | (2019.01) |
| A61K 31/28 | (2006.01) |
| A61K 31/395 | (2006.01) |
| G01N 33/68 | (2006.01) |
| G01N 33/96 | (2006.01) |

(52) U.S. Cl.
CPC ........ *A61K 31/555* (2013.01); *A61K 31/7068* (2013.01); *A61K 33/243* (2019.01); *G01N 33/5308* (2013.01); *G01N 33/60* (2013.01); *G01N 33/6848* (2013.01); *G01N 33/96* (2013.01); *A61K 2300/00* (2013.01); *G01N 2800/52* (2013.01); *G01N 2800/56* (2013.01)

(56) References Cited

U.S. PATENT DOCUMENTS

| | | | |
|---|---|---|---|
| 9,879,266 | B2 | 1/2018 | Khvorova et al. |
| 2008/0280774 | A1 | 11/2008 | Burczynski et al. |
| 2008/0286774 | A1 | 11/2008 | Turteltaub et al. |
| 2009/0325893 | A1 | 12/2009 | Garland et al. |
| 2018/0209984 | A1 | 7/2018 | Henderson et al. |

FOREIGN PATENT DOCUMENTS

| | | |
|---|---|---|
| WO | WO 2002/028345 A2 | 4/2002 |
| WO | 2012/023960 A2 | 2/2012 |
| WO | WO-2013-055735 A1 | 4/2013 |
| WO | WO 2013/164365 A2 | 11/2013 |

OTHER PUBLICATIONS

Pieck, A.C. et al. British Journal of Cancer 98:1959-1965. (Year: 2008).*

Wurz, G.T. et al. International Journal of Cancer 136:1485 (online Feb. 8, 2014). (Year: 2014).*

PCT International Search Report & Written Opinion, International Application No. PCT/US2016/041382, dated Nov. 7, 2016, 27 Pages.

"Bacterial Endotoxins/Pyrogens," U.S. Food & Drug Administration, Technical Guide, Mar. 1985, pp. 5, Retrieved from the Internet <URL:http://www.fda.gov/ICECI/Inspections/InspectionGuides/InspectionTechnicalGuides/ucm07291 8.htm> [retrieved on Sep. 20, 2016].

"Carboplatin Injection," Sagent Product Insert, Dec. 2012, pp. 1, Retrieved from the Internet <URL:http://www.sagentpharma.com/wp-content/uploads/2014/11/Carboplatin_PI.pdf> [retrieved on Sep. 20, 2016].

"Ethanol Precipitation of Nucleic Acids," Openwetware, Jul. 2012, pp. 1, Retrieved from the Internet <URL:http://openwetware.org/index.php?title=Ethanol_precipitation_of_nucleic_acids> [retrieved on Sep. 20, 2016].

"Information questionnaire for pharmaceutical specialties for Hospital Pharmacists," Gemcitabin Labatec® I.V. (Labatec-Pharma SA, Datasheet, Apr. 2012, pp. 12, Retrieved from the Internet <URL: http://www.labatecpharma.com/wp-content/uploads/2012/07/GSASA +MSDS-Gemcitabin-v1-072012.pdf> [retrieved on Sep. 20, 2016].

"MSDS, Product Name: Oxaliplatin Injection (Solution for Intravenous Use)," Hospria, Datasheet, Feb. 2010, Retrieved from the Internet <URL:https://www.hospira.com/en/images/SDS-Oxaliplatin_Injection-060214-tcm81-95525.pdf> [retrieved on Sep. 20, 2016].

De Castria, T.B., et al., "Cisplatin versus Carboplatin in Combination with Third-generation Drugs for Advanced Non-small Cell Lung Cancer (Review)," Cochrane Database of Systematic Reviews, 2013, p. 8, vol. 16, No. 8.

Hah, S.S. et al., "Kinetics of carboplatin-DNA binding in genomic DNA and bladder cancer cells as determined by accelerator mass spectrometry," Chem. Res. Toxicol., 2006, pp. 622-626, vol. 19, No. 5. Abstract.

Hah, S.S. et al., "Characterization of Oxaliplatin—DNA Adduct Formation in DNA and Differentiation of Cancer Cell Drug Sensitivity at Microdose Concentrations," Chem. Res. Toxicol., 2007, pp. 1745-1751, vol. 20, No. 12.

Kulp, K., "Annual Progress Report for the Resource for the Development of Biomedical Accelerator Mass Spectrometry," Mar. 2013, Retrieved from the Internet <URL:http://www.osti.gov/scitech/biblio/1077176> [retrieved on Sep. 20, 2016].

Leinwand, J.C., et al., "Body Surface Area Predicts Plasma Oxaliplatin and Pharmacokinetic Advantage in Hyperthermic Intraoperative Intraperitoneal Chemotherapy," Ann Surg Oncol., 2013, vol. 20, No. 4, pp. 1101-1104.

Mazumdar, M., et al., "Calvert's Formula for Dosing Carboplatin: Overview and Concerns of Applicability in High-Dose Setting," J Natl Cancer Inst., 2000, vol. 92, No. 17, pp. 1434-1436.

Wickremsinhe, E., et al., "Preclinical Absorption, Distribution, Metabolism, and Excretion of an Oral Amide Prodrug of Gemcitabine Designed to Deliver Prolonged Systemic Exposure," Pharmaceutics, 2013, vol. 5, No. 2, pp. 261-276.

Baskerville-Abraham, I. et al., "Development of an Ultraperformance Liquid Chromatography/Mass Spectrometry Method to Quantify Cisplatin 1,2 Intrastrand Guanine-Guanine Adducts," Chemical Research in Toxicology, 2009, vol. 22, pp. 905-912.

Bennett, C.L. et al., "Radiocarbon Dating Using Electrostatic Accelerators: Negative Ions Provide the Key Science," Science, 1977, vol. 198, No. 4316, pp. 508-510.

Binks, S.P. et al., "Kinetics and mechanism of uptake of platinum-based pharmaceuticals by the rat small intestine," Biochemical Pharmacology, 1990, vol. 40, No. 6, pp. 1329-1336.

Blommaert, F.A. et al., "Formation of DNA adducts by the anti-cancer drug carboplatin: different nucleotide sequence preferences in vitro and in cells." Biochemistry, 1995, vol. 34, No. 26, pp. 8474-8480.

Blommaert, F.A. et al., "Drug-induced DNA modification in buccal cells of cancer patients receiving carboplatin and cisplatin combination chemotherapy, as determined by an immunocytochemical method: interindividual variation and correlation with disease response," Cancer Research, 1993, vol. 53, No. 23, pp. 5669-5675.

Brown, K. et al., "Accelerator mass spectrometry for biomedical research," Methods in enzymology, 2005, vol. 402, No. 2005, pp. 423-443.

Bruhn, SL, et al., "Isolation and characterization of human cDNA clones encoding a high mobility group box protein that recognizes structural distortions to DNA caused by binding of the of the anticancer agent cisplatin," PNAS, Mar. 1992, vol. 89, pp. 2307-2311.

Calvert, A.H. et al., "Carboplatin dosage: prospective evaluation of a simple formula based on renal function," Journal of Clinical Oncology, 1989, vol. 7, No. 11, pp. 1748-1756.

Cimino, G.D. et al., "Personalized medicine for targeted and platinum-based chemotherapy of lung and bladder cancer," Bioanalysis, 2013, vol. 5, No. 3, pp. 369-391.

Cockcroft, D.W. et al., "Prediction of creatinine clearance from serum creatinine," Nephron, 1976, vol. 16, No. 1, pp. 31-41.

Coldwell, K. et al., "Detection of adriamycin-DNA adducts by accelerator mass spectrometry," Drug DNA Interaction Protocols, 2010, vol. 613, pp. 103-118.

Darcy, K.M. et al., "A Gynecologic Oncology Group study of platinum-DNA adducts and excision repair cross-complementation

(56) References Cited

OTHER PUBLICATIONS group 1 expression in optimal, stage III epithelial ovarian cancer treated with platinum-taxane chemotherapy" Cancer research, 2007, vol. 67, No. 9, pp. 4474-4481.

Degregorio, M.W. et al. "Accelerator mass spectrometry allows for cellular quantification of doxorubicin at femtomolar concentrations," Cancer chemotherapy and pharmacology, 2006, vol. 57, No. 3, pp. 335-342.

Dimopoulos, M.A. et al., "Extent of damage and repair in the p53 tumor-suppressor gene after treatment of myeloma patients with high-dose melphalan and autologous blood stem-cell transplantation is individualized and may predict clinical outcome," Journal of Clinical Oncology, 2005, vol. 23, No. 19, pp. 4381-4389.

Dingley, K., et al., "Attomole Detection of 3H in Biological Samples Using Accelerator Mass Spectrometry: Application in Low-Dose, Dual-Isotope Tracer Studies in Conjunction with 14C Accelerator Mass Spectrometry," Chemical Research in Toxicology, 1998, vol. 11, No. 10, pp. 1217-1222.

Duffull, S.B. and Robinson, B.A. "Clinical pharmacokinetics and dose optimisation of carboplatin," Clinical pharmacokinetics, 1997, vol. 33, No. 3, pp. 161-183.

Fichtinger-Schepman, A.M. et al., "Kinetics of the formation and removal of cisplatin-DNA adducts in blood cells and tumor tissue of cancer patients receiving chemotherapy: comparison with in vitro adduct formation," Cancer Research, 1990, vol. 50, No. 24, pp. 7887-7894.

Fichtinger-Schepman, A.M. et al., "Cis-Diamminedichloroplatinum(II)-induced DNA adducts in peripheral leukocytes from seven cancer patients: quantitative immunochemical detection of the adduct induction and removal after a single dose of cis-diamminedichloroplatinum(II)," Cancer research, 1987, vol. 47, No. 11, pp. 3000-3004.

Fink, D., et al., "In Vitro and in vivo resistance to cisplatin in Cells That Have Lost DNA Mismatch Repair," Cancer Research, May 15, 1997, vol. 57, No. 10, pp. 1841-1845.

Flygare, J.A. et al., "Antibody-drug conjugates for the treatment of cancer," Chemical biology & drug design, 2013, vol. 81, No. 1, pp. 113-121.

Gately, D.P. et al., "Cellular accumulation of the anticancer agent cisplatin: a review," British Journal of Cancer, 1993, vol. 67, No. 6, pp. 1171-1176.

Ghazal-Aswad, S. et al., "Pharmacokinetically guided dose escalation of carboplatin in epithelial ovarian cancer: effect on drug-plasma AUC and peripheral blood drug-DNA adduct levels," Annals of oncology, 1999, vol. 10, No. 3, pp. 329-334.

Graham, M., et al., "Clinical pharmacokinetics, of oxaliplatin: a critical review," Clinical Cancer Research, 2000, vol. 6, No. 4, pp. 1205-1218.

Grossman, H.B. et al., "Neoadjuvant chemotherapy plus cystectomy compared with cystectomy alone for locally advanced bladder cancer," New England Journal of Medicine, 2003, vol. 349, No. 9, pp. 859-866.

Guilderson, T.P. et al., "Radiocarbon as a diagnostic tracer in ocean and carbon cycle modeling," Global Biogeochemical Cycles, 2000, vol. 14, No. 3, pp. 887-902.

Gupta-Burt, S. et al. "Relationship between patient response in ovarian and breast cancer and platinum drug-DNA adduct formation," Cancer Epidemiology, Biomarkers & Prevention, 1993, vol. 2, pp. 229-234.

Hah, S.S., et al., "Recent advances in biomedical applications of accelerator mass spectrometry," Journal of biomedical science, 2009, vol. 16, No. 1, pp. 54.

Hah, S.S. et al., "Towards biomarker-dependent individualized chemotherapy: exploring cell-specific differences in oxaliplatin-DNA adduct distribution using accelerator mass spectrometry," Bioorganic & medicinal chemistry letters, 2010, vol. 20, No. 8, pp. 2448-2451.

Hah, S.S. et al., "Measurement of 7,8-dihydro-8-oxo-2'-deoxyguanosine metabolism in MCF-7 cells at low concentrations using accelerator mass spectrometry," Proceedings of the National Academy of Sciences, 2007, vol. 104, No. 27, pp. 11203-11208.

Hah, S.S., "Kinetics of carboplatin-DNA binding in genomic DNA and bladder cancer cells as determined by accelerator mass spectrometry," Chemical research in toxicology, 2006, vol. 19, No. 5, pp. 622-626.

Hah, S.S., "Characterization of oxaliplatin-DNA adduct formation in DNA and differentiation of cancer cell drug sensitivity at microdose concentrations," Chemical research in toxicology, 2007, vol. 20, No. 12, pp. 1745-1751.

Harland, S.J. et al., "Pharmacokinetics of cis-diammine-1,1-cyclobutane dicarboxylate platinum(II) in patients with normal and impaired renal function," Cancer Research, 1984, vol. 44, No. 4, pp. 1693-1697.

Henderson, P.T. et al., "Human microdosing for the prediction of patient response," Bioanalysis, 2010, vol. 2, No. 3, pp. 373-376.

Henderson, P.T et al., "A microdosing approach for characterizing formation and repair of carboplatin-DNA monoadducts and chemoresistance," International journal of cancer, 2011, vol. 129, No. 6, pp. 1425-1434.

Himmelstein, K.J. et al., "Clinical kinetics on intact cisplatin and some related species," Clinical Pharmacology & Therapeutics, 1981, vol. 29, No. 5, pp. 658-664.

Hromas, R.A. et al., "Decreased cisplatin uptake by resistant L1210 leukemia cells," Cancer Letters, 1987, vol. 36, No. 2, pp. 197-201.

Ishida, S. et al., "Uptake of the anticancer drug cisplatin mediated by the copper transporter Ctr1 in yeast and mammals," Proceedings of the National Academy of Sciences, 2002, vol. 99, No. 22, pp. 14298-14302.

Johnson, S.W. et al., "Increased platinum-DNA damage tolerance is associated with cisplatin resistance and cross-resistance to various chemotherapeutic agents in unrelated human ovarian cancer cell lines," Cancer Research, 1997, vol. 57, No. 5, pp. 850-856.

Johnson, S.W. et al., "Relationship between platinum-DNA adduct formation and removal and cisplatin cytotoxicity in cisplatin-sensitive and -resistant human ovarian cancer cells," Cancer Research, 1994, vol. 54, No. 22, pp. 5911-5916.

Lappin, G. et al., "Comparative pharmacokinetics between a microdose and therapeutic dose for clarithromycin, sumatriptan, propafenone, paracetamol (acetaminophen), and phenobarbital in human volunteers," European Journal of Pharmaceutical Sciences, 2011, vol. 43, No. 3, pp. 141-150.

Mann, S.C. et al., "Modulation of cis-diamminedichloroplatinum(II) accumulation and sensitivity by forskolin and 3-isobutyl-1-methylxanthine in sensitive and resistant human ovarian carcinoma cells," International journal of cancer, 1991, vol. 48, No. 6, pp. 866-872.

Martin, E.A. et al., "Tamoxifen DNA damage detected in human endometrium using accelerator mass spectrometry," Cancer research, 2003, vol. 63, No. 23, pp. 8461-8465.

Matsuoka, S. et al., "ATM and ATR substrate analysis reveals extensive protein networks responsive to DNA damage," Science, 2007, vol. 316, No. 5828, pp. 1160-1166.

Nelson, D.E. et al., "Carbon-14: Direct Detection at Natural Concentrations," Science, 1977, vol. 198, No. 4316, pp. 507-508.

Oshita, F. et al., "Correlation of therapeutic outcome in non-small cell lung cancer and DNA damage assayed by polymerase chain reaction in leukocytes damaged in vitro," Cancer research, 1995, vol. 55, No. 11, pp. 2334-2337.

PCT International Search Report and Written Opinion for PCT/US18/13663, dated May 14, 2018, 18 pages.

PCT Invitation to Pay Additional Fees and, Where Applicable, Protest Fee for PCT/US18/13663, dated Mar. 8, 2018, 2 pages.

Perez, E.A. "Carboplatin in combination therapy for metastatic breast cancer," The oncologist, 2004, vol. 9, No. 5, pp. 518-527.

Perkins, N.J. et al., "The Youden Index and the optimal cut-point corrected for measurement error," Biometrical Journal: Journal of Mathematical Methods in Biosciences, 2005, vol. 47, No. 4, pp. 428-441.

Poirier M.C. et al., "Platinum drug-DNA interactions in human tissues measured by cisplatin-DNA enzyme-linked immunosorbent assay and atomic absorbance spectroscopy," Environmental health perspectives, 1993, vol. 99, pp. 149-154.

(56) References Cited

OTHER PUBLICATIONS

Pommier, Y. et al., "Chk2 molecular interaction map and rationale for Chk2 inhibitors," Clinical Cancer Research, 2006, vol. 12, No. 9, pp. 2657-2661.
Reed, E. et al., "Platinum-DNA adduct in leukocyte DNA of a cohort of 49 patients with 24 different types of malignancies," Cancer Research, 1993, vol. 53, No. 16, pp. 3694-3699.
Reed, E. et al., "Evaluation of platinum-DNA adduct levels relative to known prognostic variables in a cohort of ovarian cancer patients," Cancer research, 1990, vol. 50, No. 8, pp. 2256-2260.
Reed, E. et al., "The measurement of cisplatin-DNA adduct levels in testicular cancer patients," Carcinogenesis, 1988, vol. 9, No. 10, pp. 1909-1911.
Rixe O. et al., "Oxaliplatin, tetraplatin, cisplatin, and carboplatin: spectrum of activity in drug-resistant cell lines and in the cell lines of the National Cancer Institute's Anticancer Drug Screen panel," Biochemical pharmacology, 1996, vol. 52, No. 12, pp. 1855-1865.
Safaei, R. et al., "The role of copper transporters in the development of resistance to Pt drugs," Journal of inorganic biochemistry, 2004, vol. 98, No. 10, pp. 1607-1613.
Sar, D.G. et al., "Quantitative methods for studying DNA interactions with chemotherapeutic cisplatin," TrAC Trends in Analytical Chemistry, 2010, vol. 29, No. 11, pp. 1390-1398.
Schellens, J.H., "Relationship between the exposure to cisplatin, DNA-adduct formation in leucocytes and tumour response in patients with solid tumours," British journal of cancer, 1996, vol. 73, No. 12, pp. 1569-1575.
Schiller, J.H. et al., "Comparison of four chemotherapy regimens for advanced non-small-cell lung cancer," New England Journal of Medicine, 2002, vol. 346, No. 2, pp. 92-98.
Silvestris, N. et al., "Role of gemcitabine in metastatic breast cancer patients: a short review," The Breast, 2008, vol. 17, No. 3, pp. 220-226.
Sharma, H. et al., "Blood clearance of radioactively labelled cis-diammine 1,1-cyclobutane dicarboxylate platinum (II) (CBDCA) in cancer patients," Cancer Chemotherapy and Pharmacology, 1983, vol. 11, No. 1, pp. 5-7.
Siddik, Z., "Cisplatin: mode of cytotoxic action and molecular basis of resistance," Oncogene, 2003, vol. 22, No. 47, pp. 7265-7279.
Sparreboom, A. et al., "Evaluation of alternate size descriptors for dose calculation of anticancer drugs in the obese," Journal of clinical oncology, 2007, vol. 25, No. 30, pp. 4707-4713.
Stornetta, A., et al., "ONA Adducts from Anticancer Drugs as Candidate Predictive Markers for Precision Medicine," Chem. Res. Toxicol, Dec. 12, 2016, vol. 30, pp. 388-409.
Terheggen, P.M. et al., "Monitoring of interaction products of cis-diamminedichloroplatinum(II) and cis-diammine(1,1-cyclobutanedicarboxylato)platinum(II) with DNA in cells from platinum-treated cancer patients," Cancer research, 1988, vol. 48, No. 19, pp. 5597-5603.
Toney, J., et al., "Isolation of cDNAs encoding a human protein that binds selectively DNA modified by the anticancer drug cis-diamminedichloroplatinum (II)," Proceedings of the National Academy of Sciences, 1989, vol. 86, No. 21, pp. 8328-8332.
Turteltaub, K.W., "Accelerator mass spectrometry in biomedical dosimetry: relationship between low-level exposure and covalent binding of heterocyclic amine carcinogens to DNA," Proceedings of the National Academy of Sciences, 1990, vol. 87, No. 14, pp. 5288-5292.
Turteltaub, K.W. et al., "Application of accelerated mass spectrometry (AMS) in DNA adduct quantification and identification," Toxicology letters, 1998, vol. 102, pp. 435-439.
Turteltaub, K.W. et al., "Bioanalytical applications of accelerator mass spectrometry for pharmaceutical research," Current pharmaceutical design, 2000, vol. 6, No. 10, pp. 991-1007.
Van De Vaart, P.J. et al., "DNA-adduct levels as a predictor of outcome for NSCLC patients receiving daily cisplatin and radiotherapy," International journal of cancer, 2000, vol. 89, No. 2, pp. 160-166.
Van De Vaart, P.J. et al., "Intraperitoneal cisplatin with regional hyperthermia in advanced ovarian cancer: pharmacokinetics and cisplatin-DNA adduct formation in patients and ovarian cancer cell lines," European journal of cancer, 1998, vol. 34, No. 1, pp. 148-154.
Vermorken, J.B. et al., "Pharmacokinetics of free and total platinum species after short-term infusion of cisplatin," Cancer Treatment Reports, 1984, vol. 68, pp. 505-513.
Vogel, J.S. et al., "Accelerator mass spectrometry for quantitative in vivo tracing," Biotechniques, 2005, vol. 38, No. S6, pp. 13-17.
Vogel, J.S. et al., "Accelerator mass spectrometry: Isotope quantification at attomole sensitivity," Analytical Chemistry, 1995, vol. 67, pp. A353-A359.
Von Der Maase, H. et al., "Gemcitabine and cisplatin versus methotrexate, vinblastine, doxorubicin, and cisplatin in advanced or metastatic bladder cancer: results of a large, randomized, multinational, multicenter, phase III study," Journal of clinical oncology, 2000, vol. 18, No. 17, pp. 3068-3077.
Wang, S. et al., "Gemcitabine causes minimal modulation of carboplatin-DNA monoadduct formation and repair in bladder cancer cells," Chemical research in toxicology, 2010, vol. 23, No. 11, pp. 1653-1655.
Yang, Z. et al., "Decreased cisplatin/DNA adduct formation is associated with cisplatin resistance in human head and neck cancer cell lines," Cancer chemotherapy pharmacology, 2000, vol. 46, No. 4, pp. 255-262.
Zimmermann, M., et al., "Microdose-induced Drug-DNA Adducts as Biomarkers of Chemotherapy Resistance in Humans and Mice," Molecular Cancer Therapeutics, Nov. 30, 2016, vol. 16, No. 2, pp. 376-387.
Zisowsky, J. et al., "Relevance of drug uptake and efflux for cisplatin sensitivity of tumor cells," Biochemical pharmacology, 2007, vol. 73, No. 2, pp. 298-307.
PCT International Search Report Written Opinion for PCT/US2015/054881, dated Feb. 16, 2016, 19 Pages.
Zimmermann, M., et al. "Microdose-induced Drug-DNA Adducts as Biomarkers of Chemotherapy Resistance in Humans and Mice", Mol Cancer Ther. Feb. 2017; 16(2): 376-387. doi:10.1158/1535-7163.MCT-16-0381.
International Preliminary Report on Patentability for PCT/US2018/013663 dated Jul. 25, 2019.

\* cited by examiner

|  | Condition (as determined by "Gold Standard") | | |
|---|---|---|---|
|  | Condition Positive | Condition Negative | Positive Predictive Value = $\dfrac{\Sigma \text{ True Positive}}{\Sigma \text{ Test Outcome Positive}}$ |
| Test Outcome / Test Outcome Positive | True Positive | False Positive | |
| Test Outcome Negative | False Negative | True Negative | Negative Predictive Value = $\dfrac{\Sigma \text{ True Negative}}{\Sigma \text{ Test Outcome Negative}}$ |
|  | Sensitivity = $\dfrac{\Sigma \text{ True Positive}}{\Sigma \text{ Condition Positive}}$ | Specificity = $\dfrac{\Sigma \text{ True Negative}}{\Sigma \text{ Condition Negative}}$ | |

PK identical for therapeutic and microdose (plasma ultrafiltrate)

B

Drug-DNA damage in tumor is proportional to dose

B

Oxaliplatin-DNA adduct formation and repair

| Cell line | 2h* | 4h* | 8h* | 24h* | 28h* | 48h* | $AUC_{0-48h}$# | DNA repair@ |
|---|---|---|---|---|---|---|---|---|
| 5637 | 191±15 | 367±13 | 607±32 | 710±32 | 667±77 | 505±63 | 27,720 ± 2,985 | 1.34 ± 0.30 |
| 5637R | 101±13 | 182±37 | 204±2 | 259±37 | 178±13 | 78±4 | 9,426 ± 2,457 | 3.48 ± 0.15 |
| P | 0.0014 | 0.0013 | 0.0031 | 0.0001 | 0.0004 | 0.0010 | 0.0012 | 0.0004 |

*: adducts/$10^8$ nucleotides; #: Adducts/$10^8$ nucleotides·hour, @: Adducts/$10^8$ nucleotides/hour

C

| Cell lines | Oxaliplatin | Carboplatin | Cisplatin | Gemcitabine | Doxorubicin | Methotrexate | Vinblastine |
|---|---|---|---|---|---|---|---|
| 5637 (μM) | 2.45 | 24.34 | 0.59 | 0.12 | 0.27 | 1.24 | 0.000605 |
| 5637R (μM) | 27.27 | 72.18 | 2.99 | 1.44 | 0.29 | 2.01 | 0.000595 |
| P values | <0.0001 | <0.0001 | 0.049 | 0.0015 | 0.45 | 0.18 | 0.48 |

STRUCTURE OF RADIOLABELED GEMCITABINE

A

B

C

D

A

B

C

D

E

F

METHODS FOR CYTOTOXIC CHEMOTHERAPY-BASED PREDICTIVE ASSAYS

CROSS REFERENCE TO RELATED APPLICATIONS

This application is a national phase application of International Application No. PCT/US2016/041382, filed Jul. 7, 2016, which claims the benefit of U.S. Provisional Application No. 62/190,002, filed Jul. 8, 2015, each of which is incorporated herein by reference in its entirety.

STATEMENT OF GOVERNMENT SUPPORT

This invention was made with government support under HEISN26120100013C, HEISN26120100048C, HEISN26120100084C and 1K12CA138464-01A2 awarded by National Institute of Health/National Cancer Institute; VA Merit—2 awarded by the U.S. Department of Veterans Affairs; P41 RR13461 awarded by National Institute of Health/National Institute of General Medical Sciences; and LDRD 08-LW-100 awarded by the U.S. Department of Energy. The government has certain rights in the invention.

FIELD OF THE INVENTION

The invention relates to methods, systems and kits for determining therapeutic effectiveness or toxicity of cancer-treating compounds that incorporate into or bind to DNA.

BACKGROUND OF THE INVENTION

Current prescription of chemotherapeutic drugs, including the choice of drugs and the dose, is based on the information from clinical trials that include a large population of patients. However, there is a wide range of variations in response and side effects between individual patients. Therefore, the efficacy is usually suboptimal for many patients and the side effects may be overwhelming in other patients. For example, most patients with metastatic non-small cell lung cancer (the most common cause of cancer death) receive similar platinum-based doublet chemotherapy. However, less than 30% of patients respond to this treatment. Currently, the only approach for managing drug resistance, non-response, or side effects is the "trial-and-error" scenario in which drugs are prescribed followed by monitoring of response over several weeks to many months.

There are some assays currently available that "genotype" the cancer cells. The genotyping is generally utilized for targeted therapies aimed at targeting a small molecule or antibody to a cellular protein, such as EGFR or HER2. Genotype assays for DNA damaging chemotherapy agents such as platinum-based antineoplastic drugs (e.g., platins) are currently not used in the clinic. Individual aspects of patient and tumor genetic make-ups contribute to intrinsic or acquired resistance to platinum-based drug resistance phenotypes. Numerous studies have been performed to explore the mechanisms of resistance to platinum (Siddik, Zahid H. "Cisplatin: mode of cytotoxic action and molecular basis of resistance." *Oncogene* 22.47 (2003): 7265-7279). The chemoresistance mechanisms are very complicated and involve more than 700 genes from multiple signaling pathways that include: drug metabolism, cellular transport, intracellular inactivation, repair of DNA damage, and toleration or DNA polymerase bypass of DNA damage (Matsuoka, Shuhei, et al. "ATM and ATR substrate analysis reveals extensive protein networks responsive to DNA damage." *Science* 316.5828 (2007): 1160-1166). Studies exploring individual gene alterations have essentially failed to identify clinically applicable markers for chemoresistance. Therefore, alternative tests prior to chemotherapy are needed to predict patient response to chemotherapy.

Platinum (Pt) derivatives, e.g., platinum-based antineoplastic drugs (or platins), are among the most effective and commonly used chemotherapeutic drugs for lung, bladder, breast, gynecological, gastrointestinal, testicular, hematological and other malignancies. The pharmacodynamic mechanism of platinum chemotherapy is the formation of covalent platinum-DNA adducts (FIG. 1). Platinum-based drugs preferentially interact with the nucleophilic N7-site of purine bases of DNA to form a variety of monoadducts and diadducts (crosslinks) when Pt interacts with nucleotides through one or two covalent bonds, respectively (Eastman, Alan. "The formation, isolation and characterization of DNA adducts produced by anticancer platinum complexes." *Pharmacology & therapeutics* 34.2 (1987): 155-166). These adducts induce local perturbations in the DNA double helical structure, which activate the proteins that recognize DNA damage (Toney, Jeffrey H., et al. "Isolation of cDNAs encoding a human protein that binds selectively to DNA modified by the anticancer drug cis-diamminedichloroplatinum (II)." *Proceedings of the National Academy of Sciences* 86.21 (1989): 8328-8332; Bruhn, Suzanne L., et al. "Isolation and characterization of human cDNA clones encoding a high mobility group box protein that recognizes structural distortions to DNA caused by binding of the anticancer agent cisplatin." *Proceedings of the National Academy of Sciences* 89.6 (1992): 2307-2311; and Fink, Daniel, et al. "In vitro and in vivo resistance to cisplatin in cells that have lost DNA mismatch repair." *Cancer Research* 57.10 (1997): 1841-1845). The activation of these proteins also results in cell cycle arrest, induction of DNA repair processes, and the initiation of programmed cell death.

However, the efficacy of platinum-based chemotherapy varies significantly depending on the types of cancer and individual molecular characteristics of a specific tumor. A paradigm shift to utilization of platin agents on selective patients has not occurred due to the lack of a diagnostic test to predict personalized chemotherapy response. What is needed therefore is a non-toxic, in vivo diagnostic assay that predicts patient response to subsequent chemotherapy, and possible toxic response.

Methods described herein provide such a diagnostic tool to predict patient response to subsequent chemotherapy, and possible toxic response. The methods enable a physician to segregate cancer patients into differential populations that have a higher or lower chance of responding to a particular chemotherapy. The goals of the assay described herein are to identify patients as true non-responders so that they can avoid unnecessary, toxic chemotherapy, and to increase the odds of response for test positive patients.

SUMMARY OF THE INVENTION

The instant invention is based, at least in part, on the discovery that in vivo drug activity can be measured using extremely small amounts of isotope-labeled drugs that can be given to patients and quantified through use of ultrasensitive detection of the isotope with technologies such as accelerator mass spectrometry (AMS) or equivalent. In one embodiment, the invention comprises a new diagnostic reagent consisting of a "microdose formulation" of a new radiolabeled version of a chemotherapeutic compound designed to bind to DNA or to be incorporated into DNA. In one embodiment, the diagnostic reagent is administered to a patient at a dose that is safe for the patient and allows detection of a transient biomarker, a radiolabeled drug-DNA adduct, or radiolabeled modified bases incorporated into the DNA (FIG. 2).

Accordingly, provided herein are methods and compositions for individually optimizing drug therapy to a patient. In one embodiment, optimization of said drug therapy is performed by the steps shown in FIG. 3.

For example, the invention is directed to a method of predicting a patient's response to chemotherapy, comprising: (1) obtaining a sample collected from the patient after administration of a microdose of a chemotherapeutic drug, wherein said chemotherapeutic drug binds to a DNA of the patient and forms a DNA-drug adduct, and wherein said chemotherapeutic drug is at least in part radiolabled; (2) isolating DNA and DNA-drug adduct from the sample; (3) measuring an isotope ratio in the isolated DNA and DNA-drug adduct; (4) calculating a DNA-drug adduct frequency in the sample based on the measured isotope ratio; and (5) predicting the patient's response to a therapeutic dose of said chemotherapeutic drug by comparing the DNA-drug adduct frequency with a threshold. In addition, the invention is directed to a method of predicting a patient's response to chemotherapy, comprising: (1) obtaining a sample collected from the patient after administration of a microdose comprising two or more chemotherapeutic drugs, wherein said chemotherapeutic drugs bind to a DNA of the patient and form a DNA-drug adduct, and wherein one or more of the chemotherapeutic drugs are at least in part radiolabled; (2) isolating DNA and a DNA-drug adduct from the sample; (3) measuring isotope ratios in the isolated DNA and DNA-drug adduct; (4) calculating a DNA-drug adduct frequency in the sample based on the measured isotope ratios; and (5) predicting the patient's response to a therapeutic dose of one of the chemotherapeutic drugs or a combination of the chemotherapeutic drugs by comparing the DNA-drug adduct frequency with a threshold.

The invention is also directed to a method of predicting a patient's response to chemotherapy, comprising: (1) obtaining cells collected from the patient; (2) exposing the cells to a diagnostic reagent comprising a microdose of a chemotherapeutic drug, wherein said chemotherapeutic drug binds to a DNA of the cells and forms a DNA-drug adduct, and wherein said chemotherapeutic drug is at least in part radiolabled; (3) isolating DNA and DNA-drug adduct from the cells; (4) measuring an isotope ratio in the isolated DNA and DNA-drug adduct; (5) calculating a DNA-drug adduct frequency in the cells based on the measured isotope ratio; and (6) predicting the patient's response to a therapeutic dose of said chemotherapeutic drug by comparing the DNA-drug adduct frequency with a threshold.

The invention is also directed to a kit for predicting a patient's response to chemotherapy, comprising: (1) a microdose of a chemotherapeutic drug, wherein said chemotherapeutic drug binds to a DNA of the patient and forms a DNA-drug adduct, and wherein said chemotherapeutic drug is at least in part radiolabled; and (2) instructions for administering said microdose to the patient and collecting a sample from the patient.

The invention is also directed to a system for predicting a patient's response to chemotherapy, comprising: (1) a measuring means for measuring an isotope ratio of a sample, wherein the sample comprises DNA and DNA-drug adduct collected from the patient after administration of a microdose of a chemotherapeutic drug, wherein said chemotherapeutic drug binds to a DNA of the patient and forms DNA-drug adduct, and wherein said chemotherapeutic drug is at least in part radiolabled; (2) a first processor calculating a DNA-drug adduct frequency in the sample based on the measured isotope ratio; (3) a memory storing data comprising a correlation between DNA-drug frequencies and therapeutic outcomes; (4) a second processor predicting the patient's response to a therapeutic dose of said chemotherapeutic drug by comparing the DNA-drug adduct frequency in the sample and the data; and (5) an output means providing a report on the prediction.

Furthermore, the invention is directed to (1) optimal dose and compositions of chemotherapeutic drugs, including radioactivity, for the pretreatment diagnostic assay, (2) specific methods for administering chemotherapeutic drugs for the pretreatment diagnostic assay, (3) specific methods for collecting, processing and analyzing samples from patients for the pretreatment diagnostic assay, (4) useful ranges of drug-DNA adduct frequencies induced by administration of chemotherapeutic drugs for the pretreatment diagnostic assay and (5) specific methods of processing and analyzing data for the pretreatment diagnostic assay.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 5 is a chart of possible clinical diagnostic assay outcomes.

DETAILED DESCRIPTION

The details of various embodiments of the invention are set forth in the description below. Other features, objects, and advantages of the invention will be apparent from the description and the drawings, and from the claims.

Definitions

The term "platinum-based antineoplastic drugs" (e.g., platins) as used herein refers to chemotherapeutic agents to treat cancer. Platins are coordination complexes of platinum. They bind to DNA as monoadducts, diadducts (interstrand and intrastrand crosslinks) or DNA-protein crosslinks. The resultant DNA adducts inhibit DNA repair and/or DNA synthesis in cancer cells. Examples of platins include: cisplatin, carboplatin, oxaliplatin, satraplatin, picoplatin, nedaplatin, triplatin, and lipoplatin.

The term "microdose" as used herein refers to a non-therapeutic, non-toxic dosage of a therapeutic compound, e.g., a chemotherapeutic compound. Typically, a microdose ranges from between 10% to 0.01% of a therapeutic dose of a patient in need thereof. In a preferred embodiment, a microdose is about 1% of a therapeutic dose of a patient in need thereof. A therapeutic dose of chemotherapeutic compound is a patient specific dose, e.g., dependent on patient height and weight, disease state, and the like.

The term "Accelerator Mass Spectrometry" (AMS) as used herein refers to an analytical technique that measures isotope ratios at extremely low levels. An AMS instrument separates isotopes of individual atoms based on atomic weight by accelerating the atoms through strong magnetic fields. The extreme sensitivity of AMS is the result of counting rare isotopic atoms directly instead of counting their radioactive decay events. Specificity for individual isotopes occurs by instrument design and operation. Application of AMS allows use of drugs at concentrations so low as to be considered non-radioactive and non-toxic. The sensitivity of AMS allows the use of tissue samples obtained from needle biopsy or in sized blood samples to quantitate extremely low concentrations of drugs and their disposition into DNA. This method can quantify attomoles ($10^{-18}$ moles) of a drug in clinical samples with radiological doses as low as a few hundred nanocuries per person.

Figure 4A:
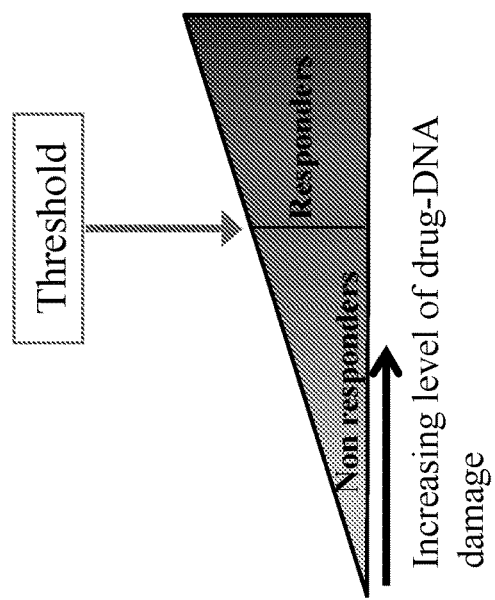
FIG. 4 is a schematic diagram of a clinical trial to demonstrate efficacy of microdose-based predictive diagnostic testing. A) Patients with cancer will be administered radiolabeled drug microdoses prior to blood sampling and tumor biopsy. DNA will be isolated from peripheral blood mononuclear cells (PBMC), tumor tissue or both, and assayed for drug-DNA damage using AMS. Patients will then begin a relevant chemotherapy regimen and will be followed for response to therapy as the primary endpoint. B) The drug-DNA damage levels will be correlated to response in sufficient patient numbers to allow for identification of range of predictive threshold levels, above which patient are more likely or predicted to respond to therapy.
Figure 4B:
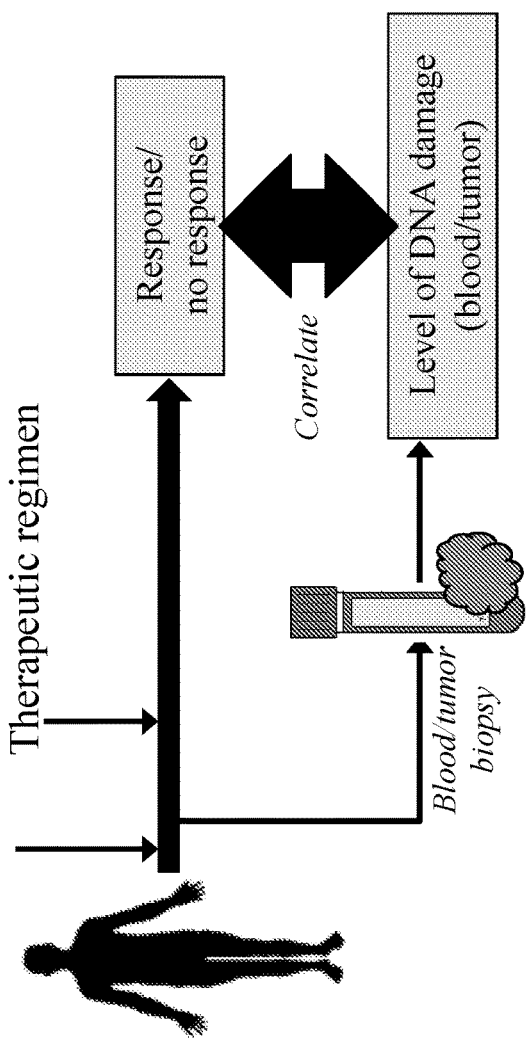

The term "clinically useful adduct frequency range" as used herein refers to the clinically observed and quantified drug-DNA adduct frequency range when (1) all patients from a representative cancer type are dosed with the same formulated microdose of the same drug or drug cocktail, and (2) all the patient samples are collected at about the same time post dosing. Clinically useful implies that the patient population contains responders and non-responders, each with an associated drug-DNA adduct frequency (FIG. 4). Tumor response can be assessed using criteria such as Response Evaluation Criteria In Solid Tumors (RECIST), or patient survival or progression-free survival. Toxic response can be assessed using criteria such as Common Terminology Criteria for Adverse Events (CTCAE). Clinically useful implies that the mean of the drug-DNA adduct frequencies for all responders is statistically different from the mean of the drug-DNA adduct frequencies for all of the non-responders. When such differences exist in the clinically useful range, it is possible to extract standard diagnostic variables ("Clinical Tests: sensitivity and specificity" Lalkhen and McClusky 2008) from the data set that are useful for physicians to assess the probability that their patient will respond to full dose chemotherapy based upon the patient's drug-DNA adduct frequency measurement. By applying one or several cut-off values to the data set, the diagnostic test can be characterized by the clinical test variables of sensitivity, specificity, positive predictive value (PPV), and negative predictive value (NPV).

As used herein, the term "DNA binding agent" refers to a drug that binds to or is incorporated into DNA, and the term "DNA adduct" refers to a modified base of DNA containing a DNA binding agent that is either bound to DNA or is incorporated into DNA as a base analogue. In some embodiments, the DNA binding agent is a chemotherapeutic drug.

Diagnostic Formulations of Radiolabeled Chemotherapeutic Drugs

Provided herein are compositions of novel diagnostic reagents comprising a compound that is at least in part radiolabeled, and binds to or incorporates into DNA. These compounds can be detected with high sensitivity by AMS, for e.g., by detection of DNA adduct formation in vitro or in vivo. Due to the sensitivity of AMS, the dose of the compound can be less than the therapeutic dose. In some embodiments, a dose of a compound that is less than the therapeutic dose is referred to as a "microdose".

In some embodiments, the microdose of the compound is 10%, 9%, 8%, 7%, 6%, 5%, 4%, 3%, 2% 1%, 0.9%, 0.8%, 0.7%, 0.6%, 0.5%, 0.4%, 0.3%, 0.2%, or 0.1% of the therapeutic dose of said compound. In some embodiments, the microdose of radiolabeled compound is 0.01-20% of the therapeutic dose. In some embodiments, the microdose of a compound is 0.01-10% of the therapeutic dose. In some embodiments, the microdose of a compound is 0.01-3% of the therapeutic dose. In a preferred embodiment, the microdose of radiolabeled compound is 1% of the therapeutic dose.

In some embodiments, the therapeutic dose is calculated using Calvert's formula as described in Calvert, A. H., et al. "Carboplatin dosage: prospective evaluation of a simple formula based on renal function." *Journal of Clinical Oncology* 7.11 (1989): 1748-1756).

In some embodiments, the therapeutic dose is calculated using DuBois and DuBois formula.

In some embodiments, the chemotherapeutic drug is an alkylator, an antimetabolite, or a cytotoxic antibiotic. In some embodiments, the radiolabeled compound is carboplatin, oxaliplatin and gemcitabine. In some embodiments, the DNA-binding compound is mechloroethamine, cyclophosphamide, melphalan, chlorambucil, ifosfamide, busulfan, N-nitroso-N-mythylurea, carmustine, lomustine, semustine, fotemustine, streptozotocin, dacarbazine, mitocolomide, temozolomide, thiotepa, mitomycin, diaziquone, carboplatin, oxaliplatin, procarbazine, hexamethylmelamine, gemcitabine, decitabine, vidaza, fludarabine, nelarabine, cladribine, pentostatin, thioguanine, mercaptopurine, doxorubicin, or mitomycin.

In some embodiments, the composition of diagnostic compounds comprises more than one kind of chemotherapeutic drugs. In one embodiment, the radiolabel is $^{14}$C. In another embodiment, the radiolabel is $^{3}$H.

In some embodiment, the composition of diagnostic compounds comprises one chemotheraoeutic drug labeled in $^{14}$C and a different chemotherapeutic drug labeled with $^{3}$H. Thus, provided herein are microdose formulations comprising, for example, $^{14}$C carboplatin or $^{14}$C oxaliplatin that are administered to a patient at a dose of about 1% of a therapeutic dose. In a preferred embodiment, the microdose of radioactive compound is both safe and non-toxic to cancer patients, while being of sufficient dose and specific activity to allow quantification of induced drug-DNA adduct formation.

In one embodiment, the choice of a dose of the radiolabeled drug in the microdose formulation that is administered to a patient is such that the DNA damage induced by exposure to the microdose is predictive of the greater damage induced by a non-radioactive chemotherapy drug given at a therapeutic dose. A patient administered the microdose formulation at the chosen dose of the radiolabeled drug will result in an adduct frequency that is within the clinically useful adduct frequency range.

Administration of Diagnostic Formulation to a Patient

In some embodiments, the assay comprises administration of a microdose of a diagnostic formulation of a radiolabeled DNA binding agent to a patient to stratify patients into predicted responders and nonresponders. The assay is used to measure the damage and repair to surrogate and tumor tissue cells caused by a specific DNA binding agent for an individual patient.

In some embodiments, the patient has cancer. In some embodiments, the patient has a disorder selected from the group consisting of: aggressive non-Hodgkin lymphoma, anal cancer, basal cell cancer, squamous cell skin cancer, bladder cancer, bone cancer, breast cancer, central nervous system cancer, cervical cancer, esophageal cancer, gastric cancer, head and neck cancer, hepatobiliary cancer, Hodgkin lymphoma, small lymphocytic lymphoma, mantle cell lymphoma, melanoma, mesothelioma, multiple myeloma, neuroendocrine tumors, non-small cell lung cancer, ovarian cancer, colon cancer, pancreatic cancer, rectal cancer, penile cancer, prostate cancer, small cell lung cancer, T-cell lymphoma, testicular cancer, thymoma, and uterine cancer.

In some embodiment, a patient is administered with a microdose comprising [$^{14}$C]carboplatin wherein the radioactivity of the microdose is $5\times10^6$ to $20\times10^6$ dpm/kg body weight of the patient. In some embodiments, [$^{14}$C]carboplatin contains $^{14}$C in a cyclobutane dicarboxylic acid group. In some embodiments, [$^{14}$C]carboplatin forms carboplatin-DNA monoadduct.

In some embodiment, a patient is administered with a microdose comprising [$^{14}$C]oxaliplatin, wherein the radioactivity of the microdose is $1\times10^6$ to $10\times10^6$ dpm/kg body weight of the patient. In some embodiments, [$^{14}$C]oxaliplatin contains $^{14}$C in a cyclohexane ring. In some embodiments, [$^{14}$C]oxaliplatin forms oxaliplatin-DNA monoadduct, diadduct or both In some embodiment, a patient is administered with a microdose comprising [$^{14}$C]gemcitabine, wherein the radioactivity of the microdose is $5\times10^4$ to $100\times10^4$ dpm/kg body weight of the patient. In some embodiments, [$^{14}$C]gemcitabine contains $^{14}$C in an aromatic nucleobase.

In some embodiment, a patient is administered with a microdose comprising [$^{14}$C]carboplatin and [$^{14}$C]gemcitabine, wherein the total radioactivity of the microdose is $1\times10^6$ to $20\times10^6$ dpm/kg body weight of the patient.

In some embodiment, a patient is administered with a microdose having radioactivity less than $1.0\times10^8$ dpm/kg of body weight of the patient, or less than $0.5\times10^8$ dpm/kg of body weight of the patient, or less than $0.2\times10^8$ dpm/kg of body weight of the patient, or $0.5\times10^7$ to $2\times10^7$ dpm/kg of body weight of the patient, or $1.0\times10^7$ dpm/kg of body weight of the patient. In some embodiment, a patient is administered with a microdose having radioactivity less than 10, 9, 8, 7, 6, or 5 µCi/kg of body weight of the patient.

In some embodiments, a patient is administered with a formulation comprising a microdose of a chemotherapeutic drug, wherein the formulation is capable of being frozen without precipitation the chemotherapeutic drug.

Application of Diagnostic Formulation to a Cell Culture

In some embodiments, the assay comprises application of a microdose of a diagnostic formulation comprising a radiolabeled DNA binding agent to a cell culture of a patient to stratify patients into predicted responders and nonresponders. The assay is used to measure the damage and repair to surrogate and tumor tissue cells caused by a specific DNA binding agent for an individual patient.

In some embodiments, cells are collected from a patient having cancer. In some embodiments, cells are collected from a patient having a disorder selected from the group consisting of: aggressive non-Hodgkin lymphoma, anal cancer, basal cell cancer, squamous cell skin cancer, bladder cancer, bone cancer, breast cancer, central nervous system cancer, cervical cancer, esophageal cancer, gastric cancer, head and neck cancer, hepatobiliary cancer, Hodgkin lymphoma, small lymphocytic lymphoma, mantle cell lymphoma, melanoma, mesothelioma, multiple myeloma, neuroendocrine tumors, non-small cell lung cancer, ovarian cancer, colon cancer, pancreatic cancer, rectal cancer, penile cancer, prostate cancer, small cell lung cancer, T-cell lymphoma, testicular cancer, thymoma, and uterine cancer.

In some embodiments, the cells are exposed to 0.1 µM to 50 µM of a chemotherapeutic drug. In some embodiments, the cells are exposed to 1 µM to 20 µM of a chemotherapeutic drug. In some embodiments, the cells are exposed to 0.1 µM to 5 µM of a chemotherapeutic drug. In some embodiments, the cells are exposed to 1 µM to 20 µM of carboplatin. In some embodiments, the cells are exposed to 0.1 µM to 5 µM of oxaliplatin.

In some embodiments, the cells are washed 0.5 to 3 hours after exposure to a chemotherapeutic drug. In some embodiments, the cells are washed 0.5 to 6 hours after exposure to a chemotherapeutic drug. In some embodiments, the cells are washed 0.5 to 12 hours after exposure to a chemotherapeutic drug. In some embodiments, the cells are washed 0.5 to 24 hours after exposure to the microdose.

Sample Collection and Isolation of DNA and DNA-Drug Adduct

In some embodiments, a sample is collected from a patient administered with a microdose of the diagnostic formulation. In some embodiments, the sample is blood, urine, biopsy or surgically obtained tumor specimens of the patient.

In some embodiments, a sample is collected from a patient more than 4, 5, 6, 7, 8, 9, 10, 11, 12, 16, 24, 36, 48, or 72 hours after administration of a microdose of the diagnostic formulation. In some embodiments, a sample is collected 4 to 50 hours after administration of a microdose of the diagnostic formulation. In some embodiments, a sample is collected 4 to 36 hours after administration of a microdose of the diagnostic formulation. In some embodiments, a sample is collected 4 to 24 hours after administration of a microdose of the diagnostic formulation. In some embodiments, a sample is collected 6 to 18 hours after administration of a microdose of the diagnostic formulation. In some embodiments, a sample is collected 12 to 36 hours after administration of a microdose of the diagnostic formulation. In some embodiments, a sample is collected 20 to 28 hours after administration of a microdose of the diagnostic formulation. In some embodiments, a sample is collected 4 to 96 hours after administration of a microdose of the diagnostic formulation.

In some embodiments, a sample is collected from a cell culture exposed to a microdose of the diagnostic formulation.

In some embodiments, DNA and DNA-drug adducts present in cells are isolated from a sample. In some embodiments, this isolation procedure follows standard techniques for the isolation of genomic DNA. Some isolation procedures involve performing an ethanol precipitation step at a temperature around or lower than 4° C. The processing steps utilize low temperature storage and short incubations as much as possible to minimize the loss of label by conversion of monoadducts to diadducts in the case of carboplatin, and by DNA degradation during the isolation process. Once the biomarkers are isolated, this assay is insensitive to adduct and DNA degradation provided the sample is mixed well prior to transfer for radiolabel measurement by AMS.

Methods of Detection

Accelerator Mass Spectrometry

Systems for accelerator mass spectrometer (AMS) are described in U.S. Pat. Nos. 5,209,919; 5,366,721; and 5,376,355, 5,209,919; 5,366,721; and 5,376,355, which are each incorporated herein by reference.

AMS is a technique for measuring isotope ratios with high selectivity, sensitivity, and precision. In general, AMS separates a rare radioisotope from stable isotopes and molecular ions of the same mass using a variety of nuclear physics techniques. In the case of carbon, $^{14}C$ ions are separated and counted as particles relative to $^{13}C$ or $^{12}C$ that are measured as an electrical current. The key steps of AMS allowing quantitative and specific measurement of isotopes are the production of negative ions from the sample to be analyzed, a molecular disassociation step to convert the negatively charged molecular ions to positively charged nuclei and the use of high energies (MeV) which allow for the identification of ions with high selectivity.

Dual-Labeling and Tritium

In one embodiment, dual labeling is performed with tritium and radiocarbon for the microdose formulations, since AMS can sensitively measure radiocarbon and tritium. With dual labeling, in vivo disposition and resistance to two drugs can be simultaneously determined with AMS analysis. For example, labeling of the companion drug with tritium ($^3H$) and carboplatin with radiocarbon ($^{14}C$) would allow infusion of a single microdose containing both compounds. The single microdose would then enable use of a single biopsy sample, which lowers risk to the patient. In another embodiment, two different drugs, each containing the same radiolabel (e.g. radiocarbon) are formulated together as a microdose. In this case, the labels are quantitated by AMS before and after selective removal of one of the drugs from DNA. Alternatively, the DNA is digested and individual adducts separated by chromatography prior AMS analysis, Calculation of DNA-Drug Adduct Frequency In some embodiments, a DNA-drug adduct frequency is calculated from the isotope ratios measured by AMS.

AMS reports the ratio of radiocarbon to total carbon in units of Modern (1 Modern=97.7 attomole (amole) of $^{14}C$ per mg of total carbon). For example, a 1 mg sample of 1 Modern activity is about 15 milli DPM by scintillation counting. 1 microgram of DNA is sufficient for the analysis, which can be derived from approximately 50,000 cells. In order to have sufficient mass for sample handling during the graphite preparation, 1 mg of a "low $^{14}C$" carbon source is added in the form of tributyrin, which can be thought of as a carrier chemical. The specific activity of the carboplatin microdose is also required to calculate the drug-DNA adduct concentration. Below is a sample DNA adduct calculation for a 1 Modern sample (measured by AMS) of 1 microgram of DNA (measured by a Nanodrop spectrophotometer) from cells exposed to a carboplatin microdose with a specific activity of 16 mCi/mmol (0.26 $^{14}C$atoms per molecule).

$$1 \text{ Modern} \left(\frac{97.7 \text{ amol }^{14}C}{\text{mg total } C}\right) \times \left(\frac{0.6 \text{ mg } C}{\text{mg tributyrin}}\right) \times \left(\frac{1 \text{ mg trubutyrin}}{1 \text{ }\mu\text{g DNA}}\right) \times$$

$$\left(\frac{\text{amol carboplatin}}{0.26 \text{ amol }^{14}C}\right) \times \left(\frac{6.022 \times 10^5 \text{ molecules carboplatin}}{\text{amol of carboplatin}}\right) =$$

$$\frac{1.36 \times 10^8 \text{ carboplatin molecules}}{\mu\text{g DNA}}$$

A tributyrin-only control typically gives a measurement of 0.11 Modern (background), so the microdose formulation should give values of 0.3-10 Modern for clinical DNA samples. The AMS instrument can reliably measure up to 1000 Modern. Alternatively, the $^{14}C$ in the sample can be quantitated on an AMS instrument that measures $CO_2$ instead of graphite, as performed by TNO, the Netherlands Organisation for Applied Scientific Research. In the absence of a carrier, the sensitivity of the measurement is increased by about 10-fold. This has the advantage of reducing the required specific activity of the carboplatin in the microdose, and therefore radiation exposure to a patient.

After AMS analysis, the $^{14}C$/total C ratio can be converted to carboplatin-DNA monoadducts/$10^8$ nucleotides using the methods. In some embodiments, DNA-drug adduct frequency is 0.1 to 3 adducts per $10^8$ nucleotides. In some embodiments, DNA-drug adduct frequency is 0.1 to 60 adducts per $10^8$ nucleotides. In some embodiments, DNA-drug adduct frequency is 0.01 to 1000 adducts per $10^8$ nucleotides. In some embodiments, DNA-drug adduct frequency is 0.01 to 100 adducts per $10^8$ nucleotides. In some embodiments, DNA-drug adduct frequency is 0.01 to 30 adducts per $10^8$ nucleotides.

Methods for Predicting Outcome of Treatment for DNA Binding Drugs

The numerical value of drug-DNA adduct level generated from the tissue samples is put into a clinically derived algorithm or compared with a database of adduct levels of responders and non-responders at a post-dosing sample collection time to predict whether the patient is likely to respond to the chemotherapy upon full dose treatment. In one embodiment, the clinically derived algorithm is the calculation of PPV and NPV based upon the database of responders and non-responders.

In some embodiments, the database comprises a correlation between a therapeutic treatment and microdose DNA-adduct formation. In some embodiments, the database comprises microdose DNA-adduct formation/therapeutic outcome correlation data for a specific type of cancer. In some embodiments, the database comprises microdose DNA-adduct formation/therapeutic outcome correlation data for a specific type of tissue. In some embodiments, the database comprises microdose DNA-adduct formation/therapeutic outcome correlation data for a specific post-dosing sample collection time. In some embodiments, the database comprises microdose DNA-adduct formation/therapeutic outcome correlation data for a specific type of chemotherapeutic compound. In some embodiments, the chemotherapeutic compound is a platin. In some embodiments, the chemotherapeutic compound is carboplatin, cisplatin, oxaliplatin, gemcitabine, doxorubicin, daunorubicin, or idarubicin. In some embodiments, the therapeutic outcome includes toxicity.

In some embodiments, a threshold is predetermined based on data comprising a correlation between DNA-drug adduct formation and therapeutic outcomes. In some embodiments, a threshold is predetermined to be a value between the mean of DNA-drug adduct frequencies of responders to a chemotherapeutic drug and the mean of DNA-drug adduct frequencies of non-responders to the chemotherapeutic drug. In some embodiments, a threshold is predetermined as a midpoint value between the mean of DNA-drug adduct frequencies of responders to a chemotherapeutic drug and the mean of DNA-drug adduct frequencies of non-responders to the chemotherapeutic drug.

Figure 6:
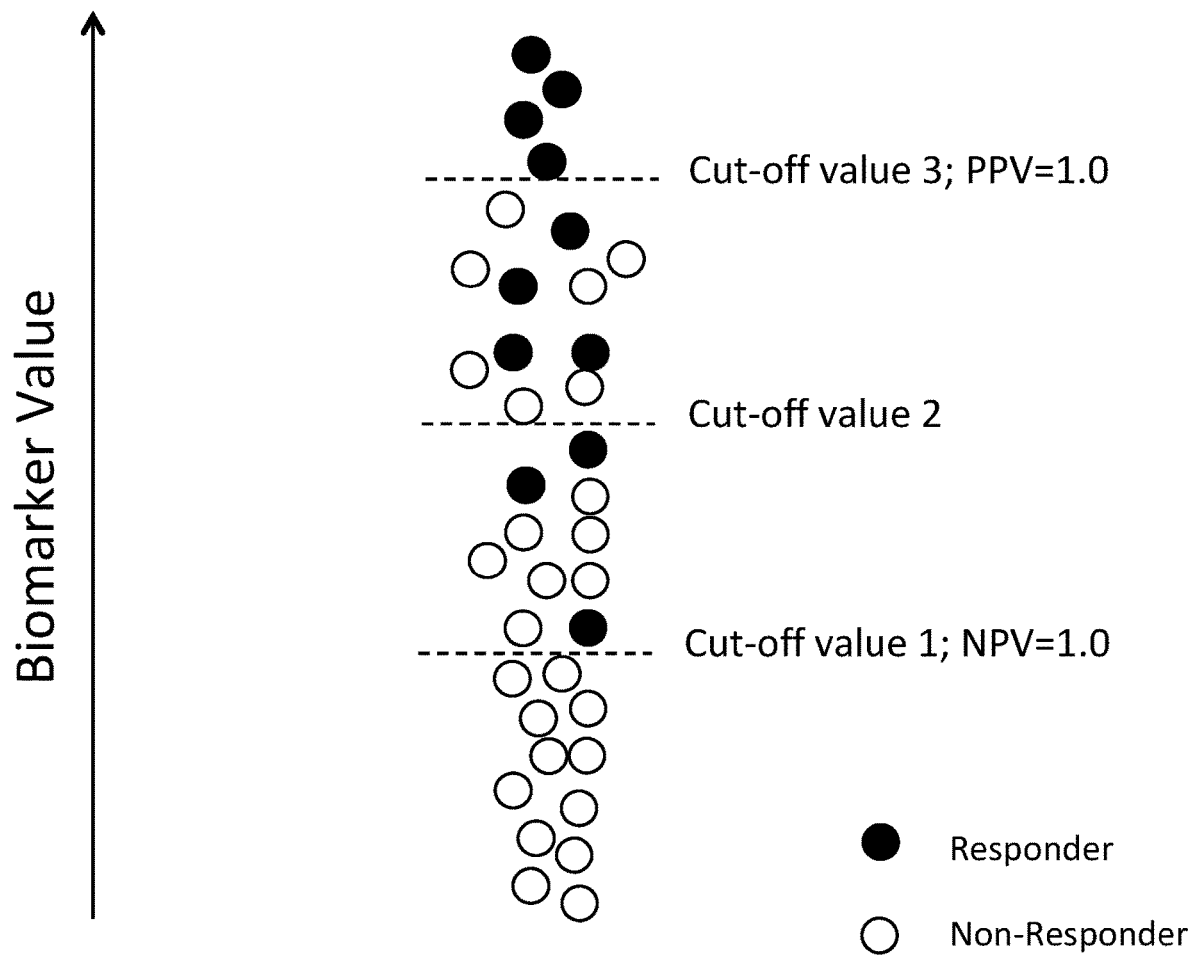
FIG. 6 is a chart of hypothetical biomarker distribution and associated response to determine probability of response based on biomarker value. The chart depicts different cut-off values having unique sensitivity and specificity. PPV=positive predictive value, NPV=negative predictive value.

In some embodiments, a DNA-drug adduct frequency is compared with a predetermined threshold to predict a patient's response to a therapeutic dose of a chemotherapeutic drug. The diagnostic assay described herein is a threshold test for predicting response to chemotherapy based upon drug-DNA adduct frequency cut-off levels. The clinical utility of diagnostic tests is well formalized (see for example Lalkhen and McClusky 2008), and relies on the following terms for the predictive diagnostic assay described here: 1. True positive: the patient is clinically responsive and the test is positive. 2. False positive: the patient is clinically non-responsive but the test is positive. 3. True negative: the patient is clinically non-responsive and the test is negative 4. False negative: the patient is clinically responsive but the test is negative In cancer applications, the gold standard for measurement of chemotherapy response is clinical evaluation for a prolonged time period after chemotherapy using the RECIST criteria. Responsive patients are those that have a complete response or a partial response. Non-responsive patients display either stable or progressive disease. Clinical tests are characterized by the terms sensitivity, specificity, positive predictive value (PPV) and negative predictive value (NPV), and are defined as in FIG. 5. Sensitivity and specificity are dependent upon the chosen cut-off levels of the assay, but independent of the population of interest subjected to the test. PPV and NPV, which are dependent on the prevalence of the response in the population of interest, are of value to a physician since they represent the likelihood of a patient responding or not responding based upon the patient's individual test result. For example, FIG. 6 is a hypothetical database for a quantitative measurement of a biomarker, such as drug-DNA adduct frequency levels, derived from 37 patients. 11 of the patients are true responders and 26 of the patients are true non-responders. In the absence of the biomarker test, the response rate for the entire population is 30%. In the cancer setting when a decision to use chemotherapy is necessary, knowing in advance whether a patient will respond (PPV=1.0) or not respond to a course of chemotherapy (NPV=1.0) is clinically valuable. If cut-off value 1 in FIG. 6 is chosen, then the assay defines a diagnostic test for which patients with a drug-DNA adduct frequency level below this cut-off would have a probability of 100% to be non-responsive (NPV=1.0), and therefore should not receive the chemotherapy. If cut-off value 3 is chosen, patients with a DNA adduct frequency level above this cut-off would have a 100% probability to be responsive (PPV=1.0), and therefore should receive chemotherapy. Today, in the absence of a predictive test for chemotherapy response, patient response rates vary from 5-10% for advanced disease, to 30-50% for most early disease, and to 70% or greater in a very limited, select set of cancers. Any incremental improvement in response likelihood is also significant in the treatment management of cancer populations. If cut-off value 2 is applied, patients with DNA adduct frequency levels above this cut-off would have a higher probability to be responsive (PPV=0.53) compared to the un-tested population, which has a 30% response rate as a whole.

In some embodiments, a DNA-drug adduct frequency is compared with a different value indicating toxicity of the chemotherapeutic drug.

Application of the Diagnostic Methods

Provided herein is a DNA binding drug-based, predictive microdosing diagnostic assay for prediction of efficacy of therapeutic drug or drug combinations and for guidance of personalized chemotherapy to predict outcome for the treatment of cancer. In certain embodiments, the assay predicts the toxicity of DNA binding drugs in a patient.

In some embodiments, this diagnostic assay will predict the capacity of cancer cells to attain that threshold level of DNA binding drug damage required for cell death upon subsequent exposure to therapeutic doses of DNA binding drugs.

In some embodiments, provided herein is a method to prescreen patients to improve the chances of observing efficacy of a DNA-binding chemotherapeutic agent, e.g., a platinum-based antineoplastic drug. Platinum-based antineoplastic drugs, or platins, are currently used for treatment of a variety of tumors, including lung, bladder, and breast cancers. According to an embodiment of the invention, patients with a variety of tumor types will be microdosed at approximately 1/100th of the therapeutic dose with a microdose formulation comprising a diagnostic reagent consisting of a radiolabeled platin, followed by measurement of drug-DNA damage prior to or during treatment with chemotherapy. The radioactive label is used for detection of the drug-DNA damage by a sensitive radiolabel detection method, e.g., AMS. The diagnostic reagent is given to allow measurement of DNA binding in the tumor or other surrogate patient tissue (e.g., peripheral blood mononuclear cells (PBMC's)) without exposing patients to toxic concentrations of platin drugs or to toxic radiation exposure.

In some embodiments, the method described herein is applied for prescreening patients in advance of therapeutic treatment. In some embodiments, the method described herein is used to monitor patients during chemotherapy. In some embodiments, the method described herein is used to measure drug-DNA adduct formation in a clinical trial for assessing efficacy of other drugs.

In one embodiment, provided herein is a method of prescreening a human subject with cancer prior to initiation of therapeutic platin treatment as a measure of intrinsic resistance to chemotherapy. Such a screening method is used to determine which patients will respond or not respond to platin based upon drug-DNA binding or repair rates for these drug-DNA adducts, either in surrogate or tumor tissues for cancer patients. Since DNA is the biological target of platins, the levels of the resulting DNA adducts are predictive of patient response (e.g., tumor shrinkage, progression-free survival, and overall survival).

In another embodiment, provided herein, is a method of screening a human subject with cancer during therapeutic platin treatment to measure acquired resistance to chemotherapy. In this embodiment, patients will be dosed with a radiolabeled platin at approximately 1/100th of the therapeutic dose followed by measurement of drug-DNA binding or repair rates for these drug-DNA adducts before initiation of the first cycle of chemotherapy and then again between one or more cycles of chemotherapy. A change in the levels of DNA adducts or repair rates for the drug-DNA adducts from the first determination to the subsequent determinations between cycles of chemotherapy are predictive of acquired resistance.

In another embodiment, this diagnostic assay is used in the development of new drugs or new combinations of drugs. Prior to initiation of treatment, patients will be given one or a few microdoses (around 1/100th the therapeutic dose) of $^{14}$C-labeled drug (e.g., [$^{14}$C]carboplatin). Biological specimens (such as blood, urine, biopsy and surgically resected specimens) will be taken and analyzed with AMS. The diagnostic assay is used to select patient populations that are likely to respond to an investigational drug used in a clinical trial, and to increase the chance for that drug to achieve a higher response rate and facilitate FDA or other regulatory agency approval. Another purpose of the diagnostic assay is to design combination drug therapy to overcome resistance to chemotherapy based on the underlying mechanisms of resistance. One example of drug design is the combination of carboplatin with a DNA repair inhibitor if increased DNA repair is the mechanism of resistance to carboplatin.

In some embodiments, a kit is used for the diagnostic assay, wherein the kit comprises a radiolabeled DNA binding compound, and instructions for administering said radiolabeled DNA binding compound as a microdose to a patient and collecting a sample from the patient.

In some embodiments, a system can be used in the implementation of the method described herein. The system comprises (1) a measuring means for measuring an isotope ratio of a sample, wherein the sample comprises DNA and DNA-drug adduct collected from the patient after administration of a microdose of a chemotherapeutic drug, wherein said chemotherapeutic drug binds to a DNA of the patient and forms DNA-drug adduct, and wherein said chemotherapeutic drug is at least in part radiolabled; (2) a first processor calculating a DNA-drug adduct frequency in the sample based on the measured isotope ratio; (3) a memory storing data comprising a correlation between DNA-drug frequencies and therapeutic outcomes; (4) a second processor predicting the patient's response to a therapeutic dose of said chemotherapeutic drug by comparing the DNA-drug adduct frequency in the sample and the data; and (5) an output means providing a report on the prediction.

In some embodiments, the method described herein can be used with other methods for prescreening patients, including RT-PCR measuring mRNA levels associated with key drug resistance genes such as ERCC1, XPF, p53, EGFR, BRCA1 and BRCA2 and many others. It can be also combined with corresponding antibody-based assays for the protein products of those genes are also available. In general, these methods are still in development for predictive medicine. These methods can be considered "genotype" assays in that the expression of DNA repair, apoptosis and other classes of genes are simplistic, since hundreds of genes interact in complex and still undefined ways to counter the exposure of tumors to oxaliplatin. These methods may be applied in combination with our microdosing diagnostic assay.

Exemplary Procedural Steps for Predicting a Patient's Reponse to Chemotherapy using the Method Disclosed Herein In some embodiments, the diagnostic assay method comprises the steps of (1) creation of the individualized biomarker in patient cells by administration of a microdose of the radiolabeled drug, (2) isolation of genomic DNA containing the biomarker, e.g., [$^{14}$C]carboplatin-DNA monoadducts, from tumor or surrogate tissue collected at an optimized time after microdosing, (3) quantification of the DNA by spectrophotometry, (4) measurement of the $^{14}$C or other radiolabel associated with the DNA by AMS analysis to determine the sample's $^{14}$C/total C ratio, (5) calculation of the drug-DNA adduct to DNA frequency ratio, and (6) comparison of the drug-DNA adduct frequency to a clinical database to predict patient response to a therapeutic dose of the therapeutic compound. In some embodiments, the method further comprises issuance of a report containing this correlation and chemotherapy response probability to the ordering physician and/or patient (FIG. 4).

Step 1. Microdosing.

The first step in this biomarker assay comprises administering an individualized drug cocktail to a patient identified as having a condition suitable for treatment with a chemotherapeutic compound, e.g., a platin compound. This diagnostic requires the patient to be exposed to a microdose of a radiolabeled compound, e.g., [$^{14}$C]carboplatin, through the same administration route as that of the chemotherapeutic dose of the compound. With time, the DNA-binding compound from the microdose is systemically distributed, taken up by cells (including tumor cells), and enters the nucleus where some of the drug molecules interact with DNA to form adducts, creating a transient biomarker. After sufficient time, free radiolabeled compound is eliminated from serum and cells. Additionally, cells have the capacity to repair drug-DNA adducts.

Step 2. Isolation of the Biomarker.

Patient tissue (a tumor specimen or surrogate tissue) is sampled at a specific time after serum clearance. The specific time is chosen such that the repair capacity of the tumor is represented in the drug-adduct frequency measurement. Tissue sampling time and processing to remove any free radiolabeled compound are used to control for optimal signal-to-noise for this assay. In an embodiment which uses [$^{14}$C]carboplatin, 24 hours post microdosing is the sampling time. In an embodiment which uses [$^{14}$C]oxaliplatin, 48 hours post microdosing is the sampling time.

DNA adducts present in cells are then isolated from the tissue. In some embodiments, this isolation procedure follows standard techniques for the isolation of genomic DNA. Some isolation procedures involve performing an ethanol precipitation step at a temperature about or less than 4° C. The processing steps utilize low temperature storage and short incubations as much as possible to minimize the loss of label by conversion of monoadducts to diadducts in the case of carboplatin, and by DNA degradation during the isolation process. Once the biomarkers are isolated, this assay is insensitive to adduct and DNA degradation provided the sample is mixed well prior to transfer for radiolabel measurement by AMS.

Step 3. DNA Measurement.

The third step of the biomarker assay is the quantification of the recovered DNA. DNA concentration may be calculated by measuring absorption at 260 nm. The absorption ratio $A_{260}/A_{280}$ can also be recorded as a quality control measurement for the purity of the DNA. Other methods of DNA quantification are known to one skilled in the art.

Step 4. Adduct Measurement.

The fourth step of the biomarker assay is detection of adduct quantity, e.g., by measurement of $^{14}$C/total C ratio by AMS. For example, $^{14}$C-containing DNA samples (about 0.1-10 μg of DNA) can be mixed with 1 mg of a low $^{14}$C carbon carrier molecule (tributyrin) to prepare the sample. This mixture is converted at high temperature in a sealed vial to graphite, the graphite is transferred into an AMS sample holder, and then the $^{14}$C/total C ratio is measured with an AMS instrument. In the samples prepared for AMS analysis, 99.9% of the carbon comes from the carrier, while the vast majority of the $^{14}$C originates from the platin-DNA adducts.

Step 5. Quantitative Biomarker Calculation.

The fifth step of the biomarker assay is the calculation of the drug-DNA adduct to DNA mass ratio. For example, the sample specific $^{14}$C/total C ratio is the $^{14}$C/total C ratio determined for a clinical sample minus the background $^{14}$C/total C ratio for the tributyrin carrier. Using the mass and carbon content of the carrier, the mass of the DNA sample, and the specific activity of the radiolabeled drug, e.g., [$^{14}$C]carboplatin, an absolute value for the number of $^{14}$C atoms per DNA base-pair can be calculated. It is important to note that with this assay, the quantified biomarker is normalized to the mass of the DNA. Consequently, this assay is not sensitive to variability in the DNA recovery step, provided there is a sufficient known quantity of DNA and $^{14}$C for precise AMS measurement. It is also important to note that the quantitative processing of DNA samples into carbon graphite, and the quantitative recovery and transfer of the graphite to an AMS sample holder are also not variables that impact the accuracy of the biomarker calculation. An AMS instrument determines only the $^{14}$C/total C ratio in the graphite and counts only a small fraction of the carbon present in the sample.

Step 6. Comparison to Clinical Data Base.

The personalized drug-DNA adduct frequency for a patient calculated above and within the useful range for a specific type of cancer is compared to a clinical database comprising a useful range of microdose-induced drug-DNA adduct frequencies (e.g., monoadduct and/or diadduct frequencies) data to predict patient response to a therapeutic dose of the therapeutic compound. This comparison provides an indicator of a likelihood of response. In some embodiments, the probability of response, anticipated response, or treatment recommendation is reported to the treating physician and/or patient so that a better-informed decision about the use of a specific chemotherapy can be made. In some embodiments, the DNA adduct frequency is used to provide a likelihood of the probability of a toxic effect or a side effect of administration of the drug to a patient.

As discussed throughout this application and illustrated in FIG. 6 above, the entire quantitative range of biomarker levels in the database is useful as a whole, since one or more cut-off levels can be applied to the data set to identify different populations with different predictive response rates. Thus, a range of adduct frequencies may be used as a threshold cut-off level in predicting a response to a therapeutic compound. In the examples to follow, we show that the clinically useful range of drug-induced DNA adduct frequency levels in a cancer patient population is dependent upon drug type and dose, the types of adducts being measured, and the time at which samples are collected. Consequently, the useful drug-DNA adduct range for a predictive diagnostic assay for chemotherapy is linked to the specific drug formulation and dose, the type of tissue being analyzed, and the time at which a tissue sample is collected.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions or methods of the invention can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein and nucleic acid chemistry, biochemistry, and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

Example 1

Microdose Induced Carboplatin-DNA Monoadducts in Breast Cancer Cell Lines are Predictive of Carboplatin Cytotoxicity at Higher Concentrations We determined if (1) microdoses of [$^{14}$C]carboplatin can induce measurable carboplatin-DNA monoadducts in cell culture and (2) that levels of DNA monoadducts induced by relevant microdose concentrations are linearly proportional to the DNA damage caused by therapeutically relevant concentrations of carboplatin in breast cancer cells. A therapeutically relevant concentration used in cell culture experiments is the average maximum plasma drug concentration observed in humans that have been administered a therapeutic dose of drug. A relevant microdose concentration used in cell culture experiments is 1% of the therapeutically relevant concentration.

Six breast cancer cell lines were tested. Carboplatin sensitive cell lines included Hs 578T ($IC_{50}$=44 µM), MDA MB 468 ($IC_{50}$=44 µM), and BT 549 ($IC_{50}$=68 µM). Carboplatin resistant cell lines included MCF-7 ($IC_{50}$=137 µM), MDA MB 231 ($IC_{50}$=250 µM), and T47D ($IC_{50}$=250 µM). The cell lines were purchased from ATCC, and cultured in the recommended media. $IC_{50}$ values were determined for each cell line using the MTT assay (Henderson et al., International Journal of Cancer 2011) after incubating cells for 72 hours with different concentrations of carboplatin. [$^{14}$C] carboplatin (53 mCi/mmol) was purchased from the GE Healthcare (Waukesha, Wis.) and further purified at Moravek Biochemical (Brea, Calif.). Unlabeled carboplatin (USP Pharmaceutical Grade) was used to minimize the usage of radiocarbon and achieve the specific activities required for microdoses and therapeutic doses.

Cells were seeded in 60-mm dishes at a density of 1×10$^6$ cells/dish and allowed to attach overnight in a 37° C. humidified atmosphere containing 5% $CO_2$. Cells were treated with 1 µM (a relevant microdose concentration) and 100 µM (a therapeutically relevant concentration) carboplatin. Both the microdose and the therapeutic cell culture treatments included 0.3 µM of [$^{14}$C]carboplatin at a final concentration 50,000 dpm/ml for 4 hours, followed by washing and incubation in culture medium free of carboplatin. This procedure mimicked in vivo carboplatin chemotherapy in which carboplatin is dosed by IV over a period of 15-60 minutes followed by a rapid decrease in plasma concentration a few hours after dosing. The number of carboplatin-DNA monoadducts was calculated based on the $^{14}$C content in genomic DNA as measured by AMS. DNA was isolated for AMS analysis of drug-DNA adduct content following a modified version of the Wizard® Genomic DNA Purification system from Promega. Cells (0.5-10 million cells) in a 1.5 ml sterile tube were lysed in the presence of 600 µl of Nuclei Lysis Solution by repeated pipetting of the solution, followed by a 15 min incubation at 4° C. with shaking. RNA was digested by adding 3 µl of RNase Solution to the nuclear lysate and mixing the sample by inverting the tube 2-5 times, followed by incubating the mixture for 15-30 minutes at 37° C. To precipitate proteins, the samples were cooled to room temperature for 5 minutes before adding 200 µl of Protein Precipitation Solution and vigorously vortexing at high speed for 20 seconds. The samples were chilled on ice for 5 minutes and then centrifuged for 4 minutes at 13,000-16,000×g. The supernatant containing the DNA was carefully removed leaving the protein pellet behind and transferred to a clean 1.5 ml sterile tube containing 600 µl of room temperature isopropanol. The solution was gently mixed by inversion and then centrifuged for 8 minutes at 13,000-16,000×g at room temperature. The supernatant was carefully removed, leaving the isolated DNA as a small white pellet. The DNA pellet was washed by the addition of 800 µl of room temperature 70% ethanol. The tube was gently inverted several times to wash the DNA, and then centrifuge for 1 minute at 13,000-16,000×g at room temperature. The ethanol was aspirated with a pipette and the DNA pellet was allowed to dry at room temperature for 10-15 minutes. 600 µl of DNase-free water was added to the isolated DNA, and the pellet was dissolved by incubating at 60° C. for 1 hour with shaking. The concentration of the DNA was determined by its absorption at 260 nm using a Nanodrop spectrophotometer, and then the samples were stored frozen at −80° C. For AMS analysis, a DNA sample was thawed, mixed well by vortexing, and 1-10 µg of DNA was then submitted for AMS analysis, which includes the addition of 1.0 mg of tributyrin as a carrier, followed by combustion to $CO_2$ and reduction to graphite according to published protocols (Ognibene, Ted J., et al. "A high-throughput method for the conversion of CO2 obtained from biochemical samples to graphite in septa-sealed vials for quantification of 14C via accelerator mass spectrometry." *Analytical chemistry* 75.9 (2003): 2192-2196). After AMS analysis, the $^{14}$C/total C ratio was converted to carboplatin-DNA monoadducts/10$^8$ nucleotides using the methods described herein.

Figure 7A:
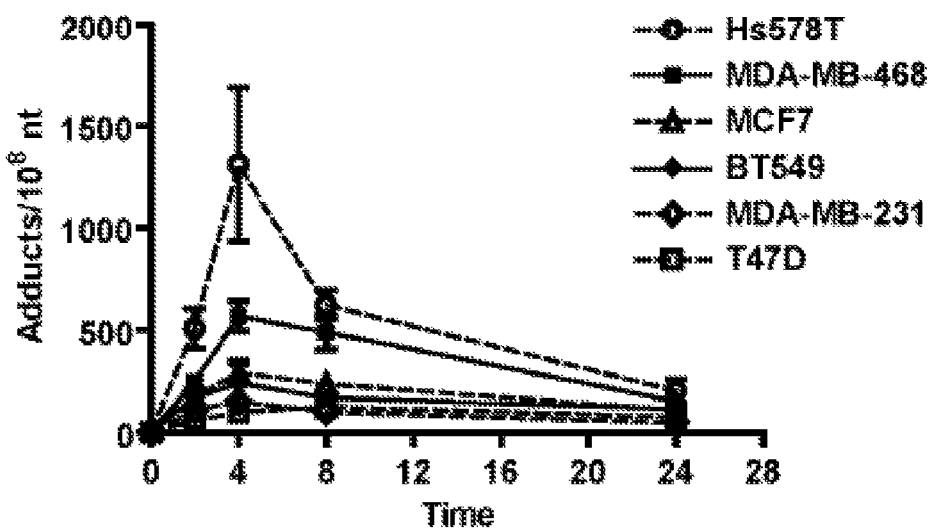
FIG. 7 provides data showing DNA adduct formation in 6 breast cancer cell lines treated with a relevant therapeutic concentration (100 µM) or a relevant microdose concentration (1 µM) of carboplatin. Carboplatin sensitive breast cancer cell lines include HS 578T, MDA-MB-468, and BT 549. Carboplatin resistant breast cancer cell lines include MCF7, MDA-MB-231, and T 47D. A) DNA adduct vs time curves in cell lines treated with microdoses of [$^{14}$C]carboplatin. B) DNA adduct level-time curves of the same cell lines treated with therapeutic [$^{14}$C]carboplatin mixed with carboplatin. C) Linear regression of carboplatin-DNA adduct levels induced by microdosing versus therapeutic carboplatin, $R^2$=0.90 p<0.001. D) Comparison of monoadduct concentration (DNA damage) in sensitive (($IC_{50}$<100 µM) and resistant ($IC_{50}$>100 µM) breast cancer cell lines after exposure to a relevant microdose or therapeutic concentration.
Figure 7B:
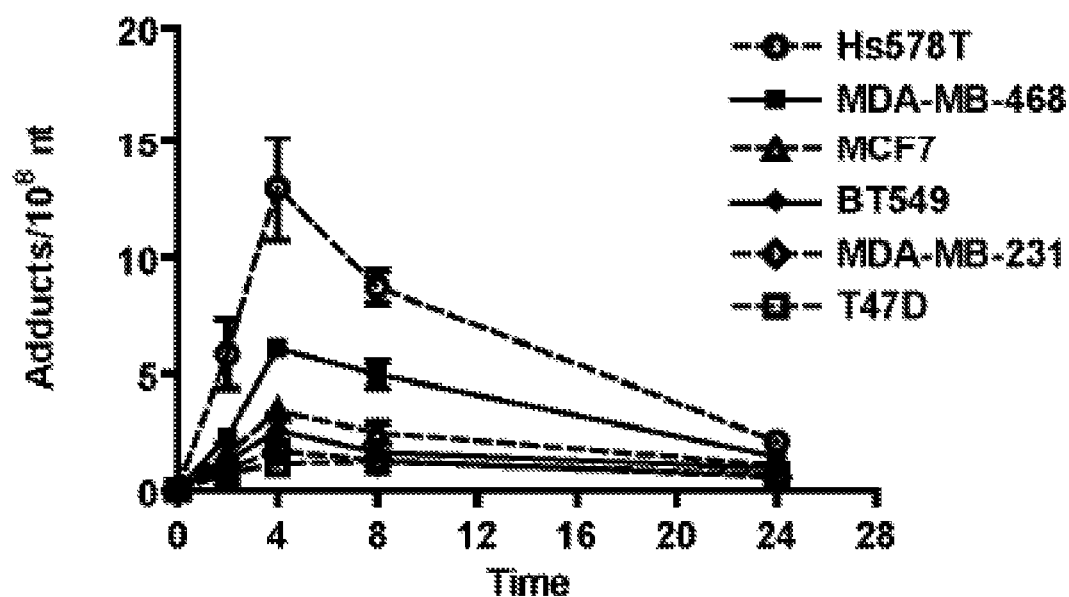

FIG. 7A shows the levels of radiolabeled carboplatin-DNA monoadducts induced by microdoses. FIG. 7B shows the levels of radiolabeled carboplatin-DNA monoadducts induced by therapeutic carboplatin. Carboplatin-DNA monoadducts could be detected in all cell lines at all time points. The ability to detect radiocarbon in all of the samples represents a point of discrimination compared to other DNA adduct measurement technologies, which generally have a substantial number of non-detection events due to the technical demands of measuring an analyte bound to DNA in the presence of a 100 million-fold excess of unmodified DNA bases.

Figure 7C:
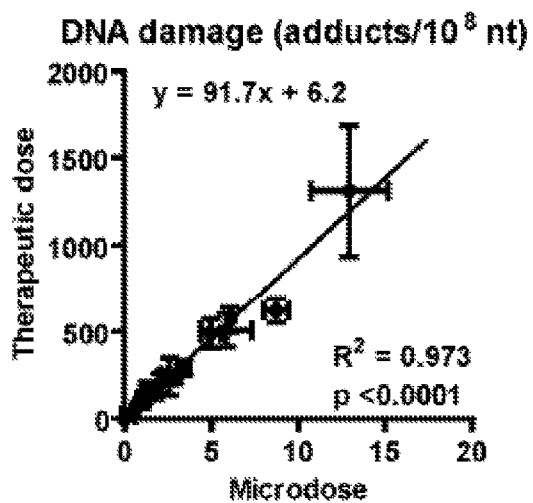

A linear regression analysis comparing carboplatin-DNA monoadduct formation in all 6 cell lines was performed. The dose-response of carboplatin-DNA monoadduct formation was significantly linear between microdose and therapeutic doses at all time points for all cell lines (FIG. 7C, p<0.001, $R^2$=0.90). The DNA damage concentrations ranged from ~1-15 monoadducts per 10$^8$ nt for the microdose, and ~100-1500 monoadducts per 10$^8$ nt for the therapeutic dose, demonstrating an approximate 100-fold difference in the DNA damage with a 100-fold difference in drug concentration. Both microdosing and therapeutic dosing with $^{14}$C- carboplatin in cell culture resulted in drug-DNA adduct levels that correlate with the carboplatin $IC_{50}$ of the cells to carboplatin.

Figure 7D:
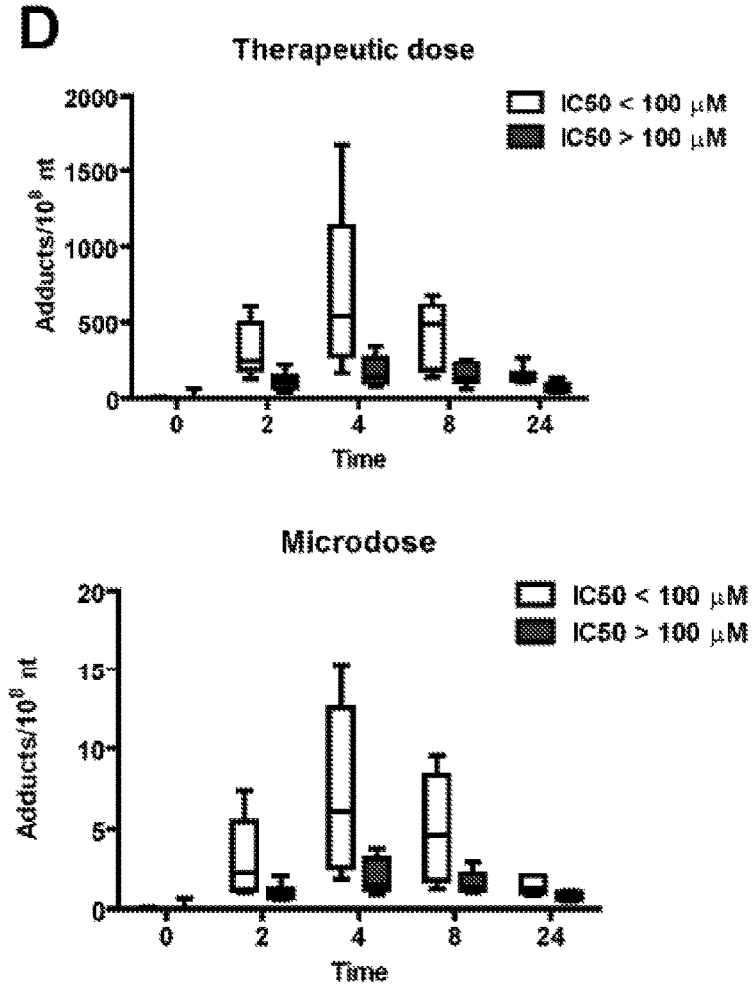

Monoadduct concentrations in sensitive (($IC_{50}$<100 µM) and resistant ($IC_{50}$>100 µM) cell lines were compared using a box and whiskers plot in FIG. 7D. The $IC_{50}$ data used here to segregate sensitive and resistant breast cancer cell lines were previously reported ("The NCI60 human tumour cell line anticancer drug screen" Robert H. Shoemaker, Nature was performed as previously reported to determine the drug concentration required to inhibit cell growth by 50% ($IC_{50}$) of cisplatin and carboplatin. [$^{14}$C]Carboplatin (at 53 mCi/mmol) was mixed with unlabeled carboplatin to achieve the specific activities required for microdoses and therapeutic doses. Table 1 lists the six NSCLC cell lines and summarizes their $IC_{50}$ characteristics, induced carboplatin-DNA monoadducts when treated with [$^{14}$C]carboplatin, and p and $r^2$ values for correlation analysis to the $IC_{50}$ concentrations.

TABLE 1

NSCLC cell line IC50 and adduct formation

| Cell Line | IC50 Cisplatin (µM) | IC50 Carboplatin (µM) | AUC of adducts-microdose (hr-adducts/$10^8$ nt) | AUC of adduct-therapeutic (hr-adducts/$10^8$ nt) | Adduct level-4 hr-microdose (/$10^8$ nt) | Adduct level-4 hr-therapeutic (/$10^8$ nt) | Adduct level-24 hr Microdose (/$10^8$ nt) | Adduct level-24 hr-therapeutic (/$10^8$ nt) |
|---|---|---|---|---|---|---|---|---|
| H23 | 4.23 ± 0.51 | 19.4 ± 8.65 | 136.6 ± 9.0 | 13255 ± 835 | 7.4 ± 1.4 | 825 ± 5.8 | 5.4 ± 0.1 | 414 ± 27.1 |
| H460 | 3.53 ± 0.76 | 22.0 ± 5.23 | 85.6 ± 8.4 | 9488 ± 902 | 6.8 ± 0.2 | 885 ± 36.3 | 1.0 ± 0.4 | 177 ± 11.5 |
| H727 | 20.0 ± 8.44 | 53.5 ± 3.65 | 61.7 ± 9.0 | 6111 ± 661 | 6.23 ± 2.73 | 684 ± 223.5 | 1.3 ± 0.1 | 174 ± 5.6 |
| HCC827 | 18.2 ± 7.44 | 86.2 ± 10.9 | 51.7 ± 2.4 | 4941 ± 739 | 2.5 ± 0.0 | 295 ± 58.8 | 1.8 ± 0.3 | 162 ± 15.4 |
| H1975 | 14.5 ± 3.80 | 88.5 ± 30.8 | 47.0 ± 4.8 | 4478 ± 353 | 3.3 ± 0.5 | 322 ± 24.1 | 1.1 ± 0.6 | 108 ± 33.3 |
| A549 | 26.3 ± 9.26 | 196.0 ± 37.9 | 31.5 ± 1.6 | 2331 ± 257 | 2.0 ± 0.4 | 163 ± 74.4 | 0.9 ± 0.0 | 74 ± 10.4 |
| P value for correlation to Cisplatin $IC_{50}$ | | | 0.04 | 0.02 | 0.07 | 0.05 | 0.28 | 0.13 |
| $r^2$ value for correlation to Cisplatin $IC_{50}$ | | | 0.70 | 0.79 | 0.59 | 0.66 | 0.28 | 0.47 |
| P value for correlation to Carboplatin $IC_{50}$ | | | 0.07 | 0.04 | 0.03 | 0.02 | 0.34 | 0.13 |
| $r^2$ value for correlation to Carboplatin $IC_{50}$ | | | 0.60 | 0.70 | 0.74 | 0.78 | 0.22 | 0.47 |

Reviews Cancer 6, 813-823, October 2006). The box represents the middle quartiles of the DNA damage for each grouping and the whiskers represent the extent of the remaining data. The black bars represent the mean monoadduct concentration for each grouping and time point. FIG. 7D shows that there are significant (P<0.001) differences in carboplatin-DNA monoadduct frequency between sensitive ($IC_{50}$<100 µM) and resistant ($IC_{50}$>100 µM) cell populations, which persist at all time points after both microdosing or therapeutic dosing. These findings show that the levels of microdose-induced DNA damage can be correlated with therapeutic dose-induced DNA damage.

Example 2

Comparison of Carboplatin-DNA Monoadducts Induced by Microdose and Therapeutic Carboplatin Concentrations in Sensitive and Resistant Human NSCLC Cell Lines Six non-small cell lung cancer (NSCLC) cell lines were treated in culture with [$^{14}$C]carboplatin. Carboplatin-DNA monoadduct levels over time were determined by measuring $^{14}$C content in genomic DNA with accelerator mass spectrometry (AMS). Cellular sensitivity to carboplatin and cisplatin was analyzed by the MTT assay (Henderson et al., International Journal of Cancer 2011).

Human NSCLC cell lines H23, H460, H727, HCC827, H1975, and A549 were purchased from ATCC and were cultured with the recommended medium. The MTT assay Carboplatin-DNA monoadducts levels at time points up to 24 hours, area under curve (AUC) for carboplatin-DNA monoadduct levels, and $IC_{50}$ values were compared for each cell line. Mean, standard deviation, range and tests for normality were used as appropriate for each experiment. Differences between sensitive and resistant cell lines across the follow-up times were estimated and tested for each cell line and AMS experiment (microdoses, therapeutic doses) using analysis of variance (ANOVA) to test for overall presence of differences between treatments and across time. Statistics were calculated with n=3 for each cell line. ANOVA analysis of $IC_{50}$ and AUC data were based on a one-sided t-test. All tests were at an experiment-wise error rate of 0.05 and all analyses used SAS/STAT software.

Figures 8A, 8B, 8C:
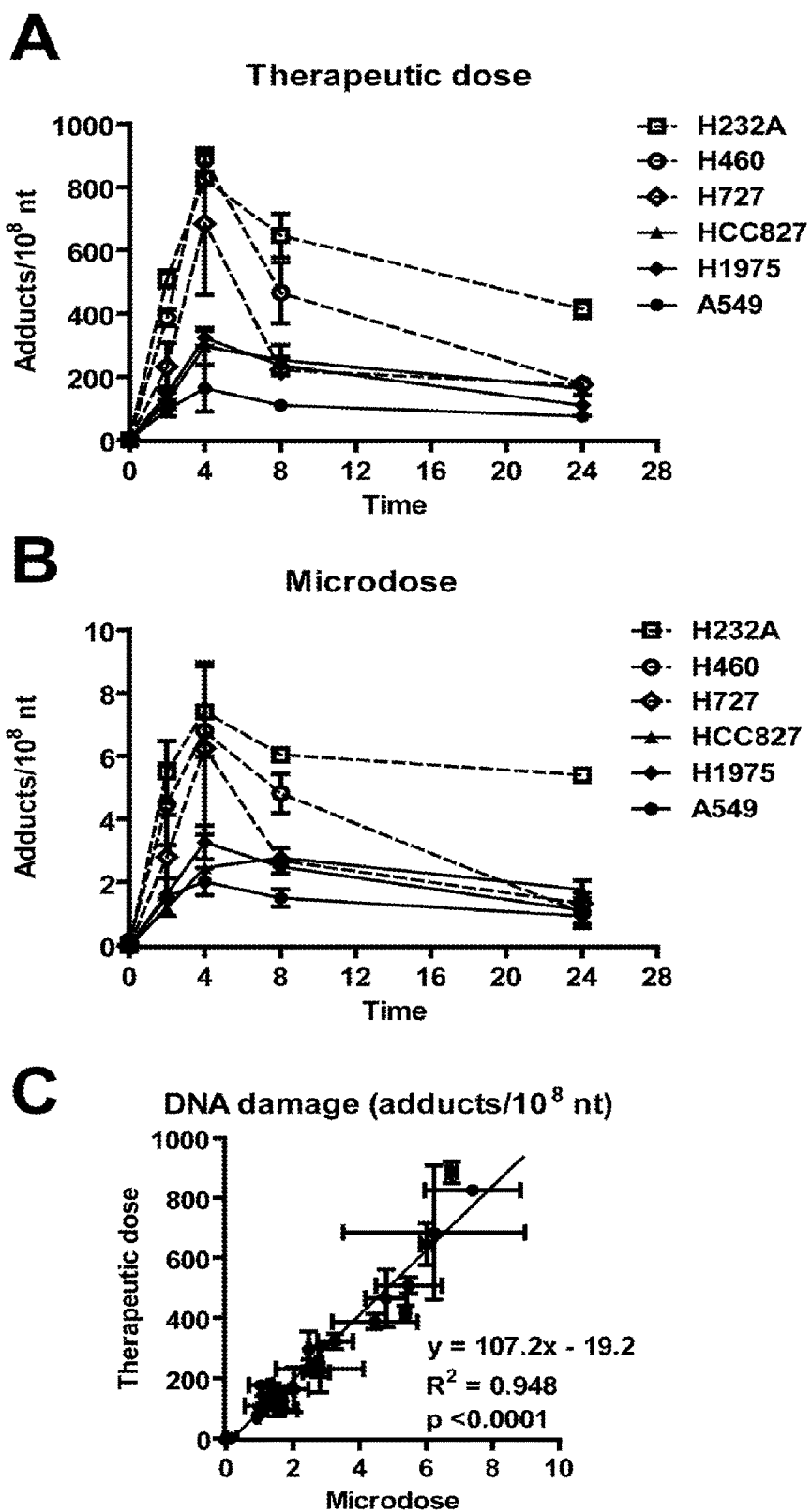
FIG. 8 shows a comparison of carboplatin-induced DNA monoadduct formation in 6 NSCLC cells after exposure to a relevant microdose concentration (1 µM) or a therapeutically relevant concentration (100 µM). (A) Monoadduct formation over time in the 6 NSCLC cell lines induced by a microdose (1 µM) of carboplatin. B) Monoadduct formation over time in the 6 NSCLC cell lines induced by a therapeutic dose (100 µM) of carboplatin. C) Linear regression of carboplatin-DNA monoadduct formation induced by microdosing and therapeutic carboplatin. Three replicates were performed for each cell line at each time point. Mean and standard error are shown.

NSCLC cell lines were cultured to >90% confluence, dosed with [$^{14}$C]carboplatin, and subjected to DNA isolation and AMS analysis. 60 mm dishes were seeded at a density of 1×10$^6$ cells/dish and allowed to attach overnight in a 37° C. humidified atmosphere containing 5% $CO_2$. At hour 0, cells were dosed with 1 µM (relevant microdose concentration) or 100 µM carboplatin (therapeutically relevant concentration), each comprising 0.3 µM [$^{14}$C]carboplatin (50,000 dpm/ml). Cells were incubated with [$^{14}$C]carboplatin for 4 h before washing and cultured with carboplatin-free medium to mimic the in vivo carboplatin half-life (1.3-6 hours) in patients. DNA was harvested from the cell lines at hours 0, 2, 4, 8 and 24 hours after initial dosing. Ten micrograms of DNA per sample was converted to graphite and measured by AMS for $^{14}$C/total C quantification. Triplicate sets of AMS experiments were performed for each cell line and time point. The 14C/total C ratio was converted to 14C atoms per DNA base-pair according to the algorithm described herein to provide values of carboplatin-DNA monoadducts per $10^8$ nucleotides. The data was plotted as carboplatin-DNA monoadducts per $10^8$ nucleotide (nt) vs time (FIGS. 8A and B).There was a time-dependent increase in the carboplatin-DNA monoadduct concentration during the first 4 hours of incubation with therapeutic or microdosing carboplatin (FIGS. 8A and B). After the cells were washed and incubated with carboplatin-free media, the monoadduct levels decreased over a period of several hours. This indicates that intracellular carboplatin is rapidly removed or inactivated in cell culture, and that DNA repair and monoadduct to diadduct conversion are predominating in the absence of extracellular carboplatin in cell cultures. Carboplatin-DNA monoadduct levels in the microdosing group had essentially the same kinetics as the therapeutic group, but with 100-fold lower adduct levels at each time point (FIGS. 8A and B). Linear regression analysis showed the monoadduct levels induced by the two carboplatin doses were highly linear and statistically significantly correlated (FIG. 8C, $R^2$=0.95, p<0.0001).

We correlated the levels of carboplatin-DNA monoadducts formed from both a microdose and a therapeutic dose over 24 hours to the $IC_{50}$ data for each cell line. The three most resistant cell lines A549, H1975 and HCC827 had the lowest carboplatin-DNA monoadduct levels. The average area under curve (AUC) of the three resistant cell lines were 43.36±9.55 hr-monoadducts per $10^8$ nt and 3916.7±1280.0 hr-monoadducts per $10^8$ nt for microdosing and therapeutic dosing, respectively. In contrast, the three most sensitive cell lines, H23, H460, and H727 had much higher and statistically different DNA monoadduct levels (FIGS. 8A and B), with values of 94.61±33.99 hr-monoadducts per $10^8$ nt (p=0.0005) and 9617.8±3172.7 hr-monoadducts per $10^8$ nt (p<0.0001), respectively. Correlation analysis was performed to determine the relation of individual carboplatin DNA-monoadduct measurements and $IC_{50}$ values of the six cell lines. Several drug-DNA adduct level endpoints inversely correlated to carboplatin cytotoxicity ($IC_{50}$), including the 4 hour adduct levels for both the microdose- and therapeutic-induced DNA monoadducts. This observation is relevant to the clinical usefulness of the invention since patients can only be sampled at one or a few time points. Similar correlations were also observed regarding cellular sensitivity to cisplatin (see p values in Table 1) indicating that microdose induced carboplatin monoadducts can predict resistance to cisplatin in cell culture.

With these NSCLC cell lines, we extended our previous findings in other cancer cell lines (1) that relevant microdose concentrations of [$^{14}$C]carboplatin in cell culture can induce measurable carboplatin-DNA monoadducts, (2) that levels of DNA monoadducts induced by relevant microdose concentrations are linearly proportional to the DNA damage caused by therapeutically relevant concentrations of carboplatin, (3) that carboplatin monoadduct levels induced by either a relevant microdose concentration or a therapeutically relevant concentration correlated to the carboplatin $IC_{50}$ of the cell lines in culture. We also showed that the carboplatin $IC_{50}$ and cisplatin $IC_{50}$ for these cell lines are linearly related to each other and that carboplatin monoadduct levels induced by either microdose or therapeutic doses correlate to the cisplatin $IC_{50}$ of these same cell lines in culture.

Example 3

Figure 1:
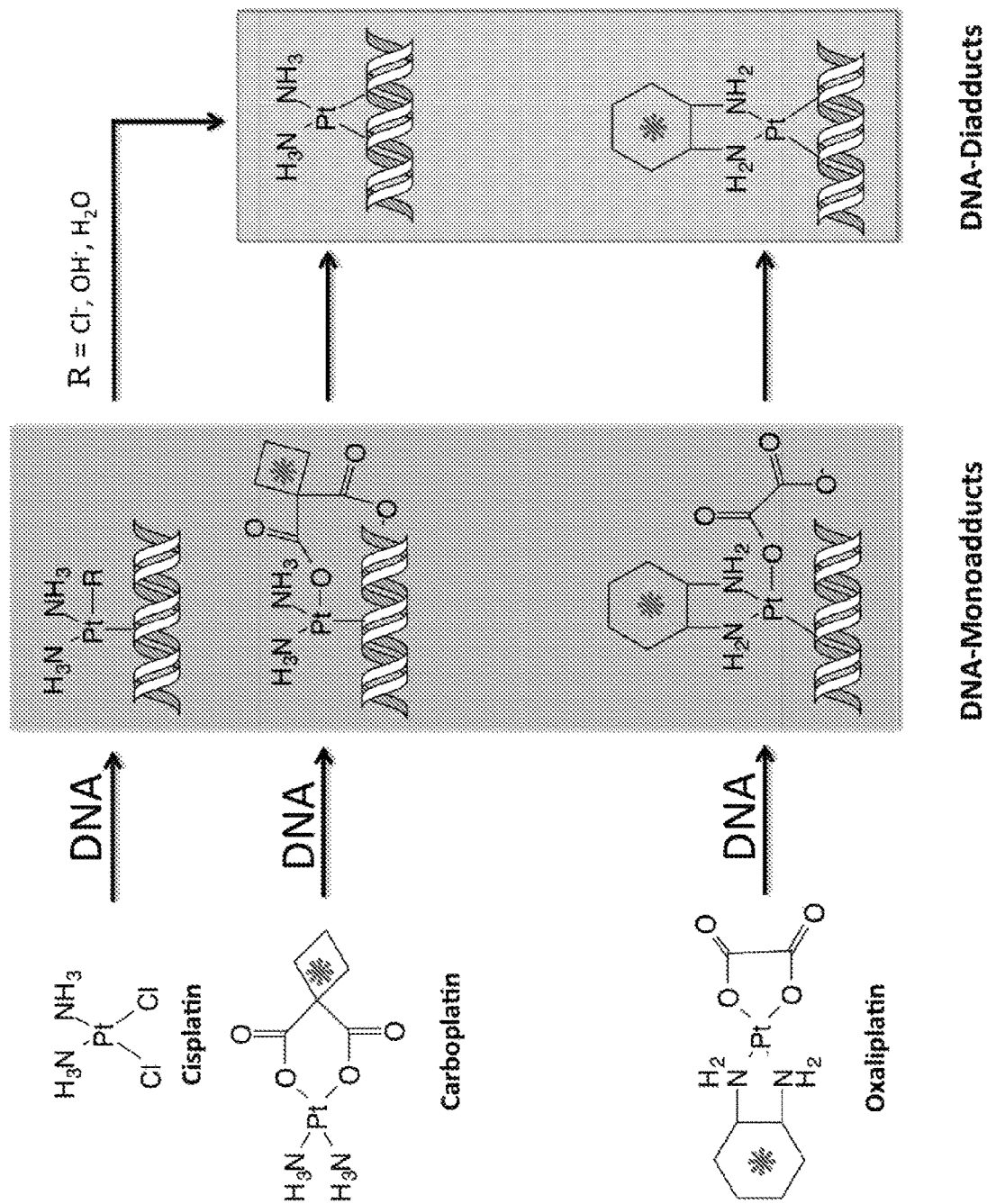
FIG. 1 shows the structures of cisplatin, carboplatin and oxaliplatin and their reaction products (drug-DNA adducts) formed upon reaction with DNA. The asterisk denotes the approximate position of $^{14}C$ labels that enable radiotracer analysis.
Figure 2:
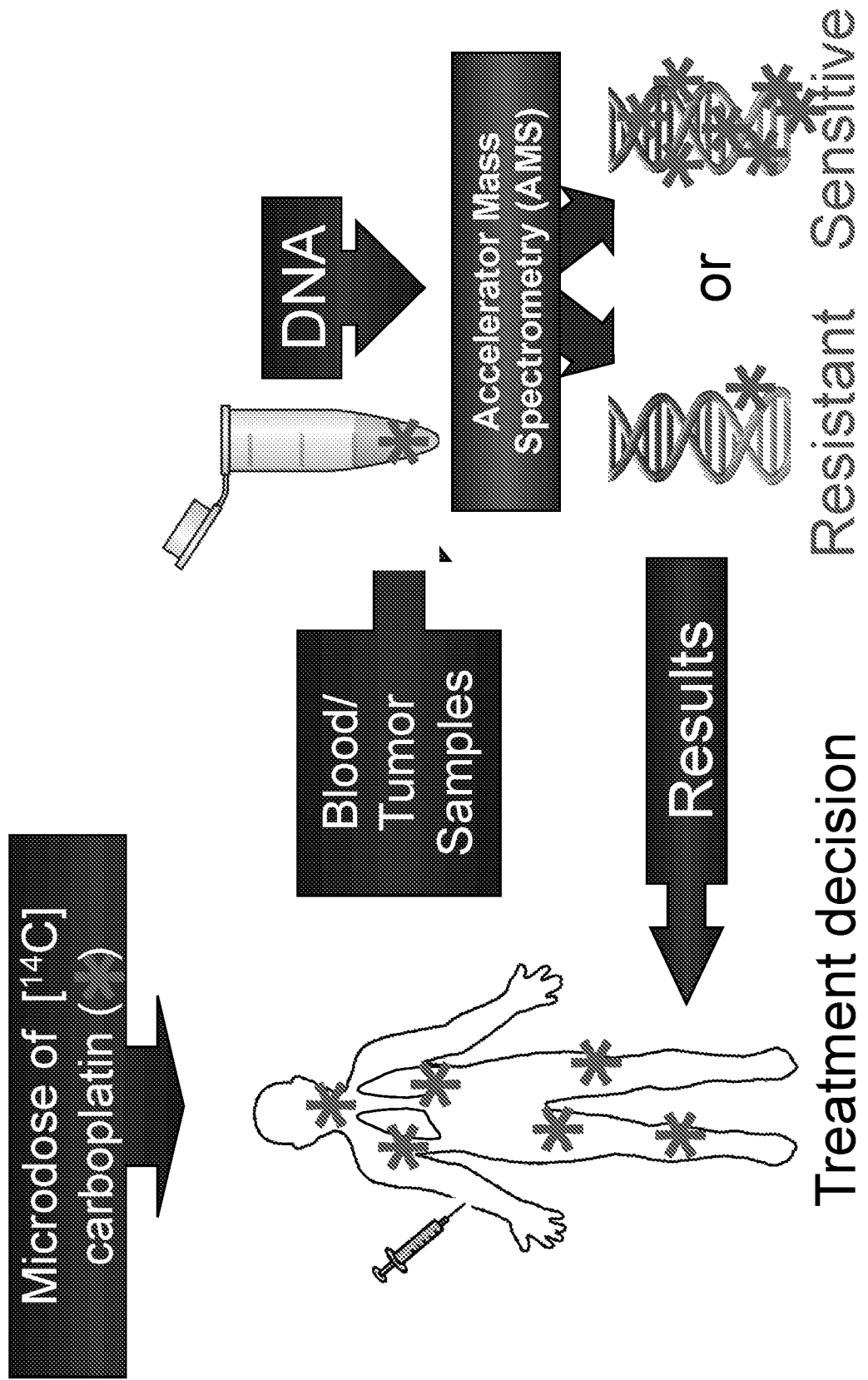
FIG. 2 is a schematic diagram of one embodiment of a predictive diagnostic test enabled by microdosing patients using [$^{14}C$]carboplatin. The test begins with administration of a microdose (~1% of the therapeutic dose) of [$^{14}C$] carboplatin, followed by blood and tumor biopsy sampling. Isolation of DNA from the samples enabled quantitation of the carboplatin-DNA adducts by AMS, whose levels in individual patients are predictive of response to subsequent full dose cisplatin- or carboplatin-based chemotherapy.
Figure 3:
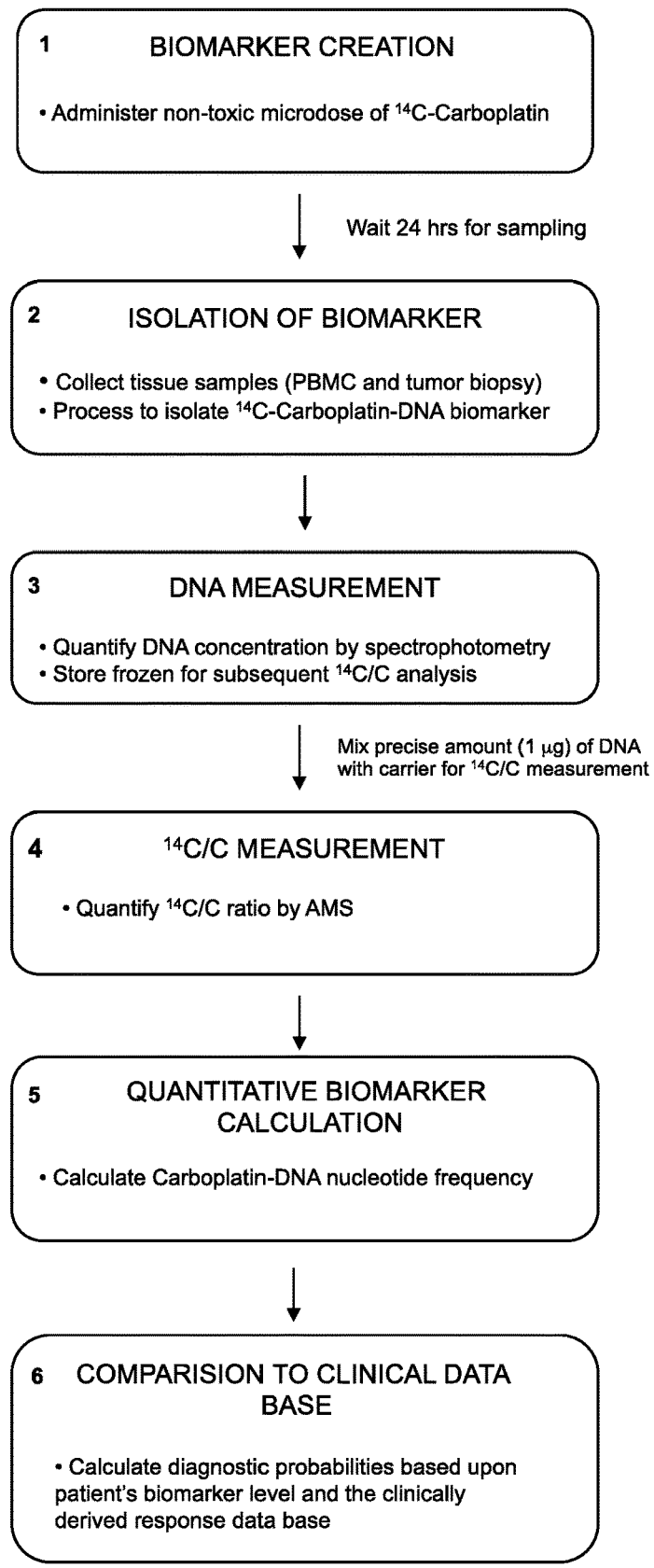
FIG. 3 is a flow-chart depicting a six step sequence for a predictive diagnostic assay based on microdose-induced drug-DNA frequencies.
Figure 9A:
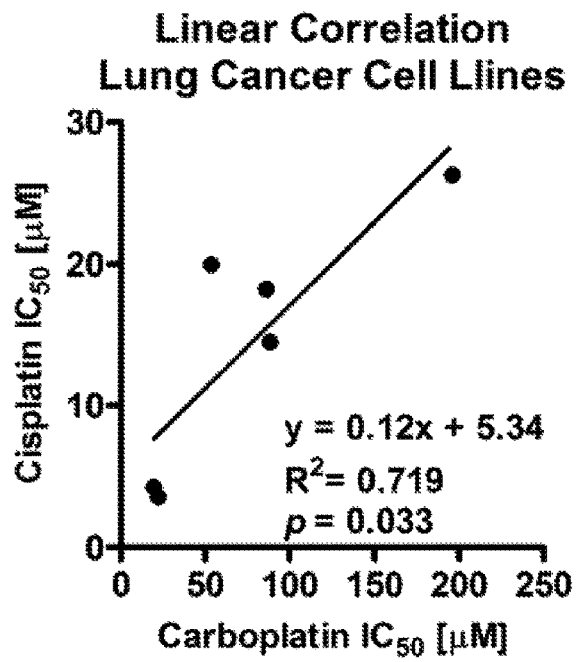
FIG. 9 shows the linear correlation of carboplatin and cisplatin $IC_{50}$ in A) six NSCLC cell lines and B) six bladder cancer cell lines.
Figure 9B:
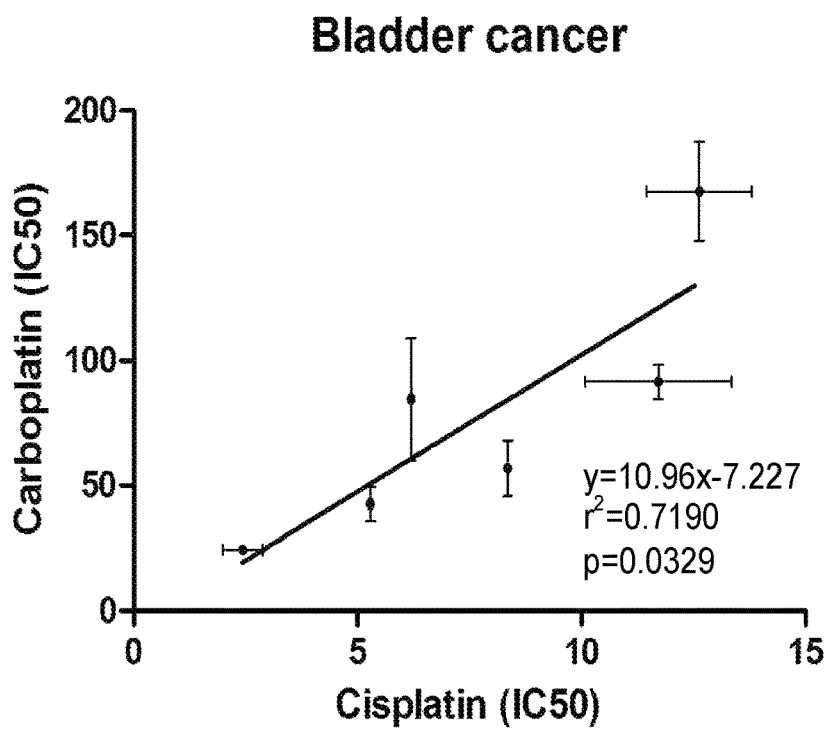

Correlation of Carboplatin-DNA Monoadduct Levels and Resistance to Both Carboplatin and Cisplatin Treatment As shown in FIG. 1, cisplatin and carboplatin form the identical DNA diadduct structure. If these diadducts are the predominant DNA lesion responsible for cell death, then the $IC_{50}$ of the two drugs should be linearly related. Thus, we measured the $IC_{50}$ of the six NSCLC cell lines from Example 2 to both cisplatin and carboplatin to determine if the sensitivity of these six NSCLC cell lines to the two drugs are correlated. We observed a statistically significant linear correlation of the cytotoxicity of these two drugs in the 6 cell lines used in this study ($R^2$=0.72, p=0.033, FIG. 9A) and also to six additional ATCC bladder cancer cell lines. ($R^2$=0.72, p=0.033), FIG. 9B). The bladder cancer cell lines and their corresponding IC50 to cisplatin and carboplatin are shown in Table 2. This data further supports the notion that a [$^{14}$C] carboplatin microdose diagnostic assay as described herein can be used to predict outcome of treatment with cisplatin.

TABLE 2

Bladder cancer cell line IC50 values for cisplatin and carboplatin

| | $IC_{50}$ (µM) | |
|---|---|---|
| Cell line | Cisplatin | Carboplatin |
| 5637 | 2.43 ± 0.45 | 24.35 ± 0.12 |
| T24 | 5.28 ± 0.04 | 42.51 ± 6.99 |
| TCCSUP | 11.72 ± 1.63 | 91.52 ± 6.81 |
| J82 | 12.64 ± 1.17 | 167.55 ± 19.87 |
| HT1197 | 6.20 ± 0.03 | 84.50 ± 24.61 |
| RT4 | 8.35 ± 0.01 | 56.94 ± 11.23 |

Example 4

Prediction of Carboplatin Chemotherapy Response in a Mouse Model Using a Microdose-Based Diagnostic Assay Carboplatin Pharmacokinetics in Mice-Validation of the Mouse Model We evaluated the plasma pharmacokinetics of carboplatin administered at both a microdose and a therapeutic dose in mice to demonstrate that cellular exposure to carboplatin ($C_{max}$ and plasma AUC over 24 hours) scales with the IV dose of carboplatin.

Figure 10A:
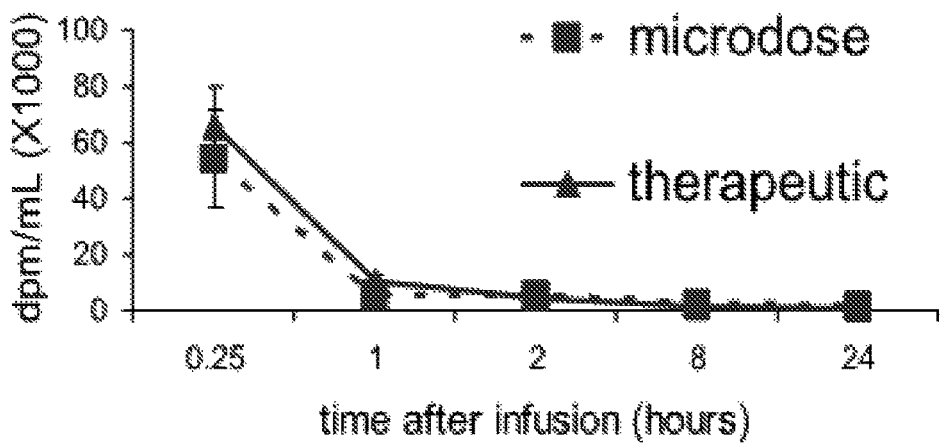
FIG. 10 shows carboplatin plasma pharmacokinetics and carboplatin-induced DNA adduct levels over time after IV administration of [$^{14}$C]carboplatin as either a microdose (0.373 mg/kg) or therapeutic dose (37.3 mg/kg) to mice with a lung cancer xenograft. A) Carboplatin PK of plasma ultrafiltrate balb/c mice given microdoses or therapeutic doses of carboplatin. B) Comparison of carboplatin DNA damage induced by therapeutic doses or microdoses in nude mice with human A549 lung adenocarcinoma tumors. C) Comparison of tumor response to carboplatin therapeutic dose for A549 and H23 2A lung tumor xenografts in nude mice. D) Relative percent of carboplatin-DNA monoadducts remaining in sensitive and resistant tumors 8 hours after excision of the tumor cells from microdosed mice.

Balb/c mice received a bolus [$^{14}$C]carboplatin tail vein injection at microdose (0.373 mg/kg; 50,000 dpm/gm) or therapeutic dose (37.3 mg/kg; 50,000 dpm/gm). Mice were sacrificed in triplicate at 15 min, 1 h, 2 h, 8 h and 24 h. Concentrations of carboplatin in plasma were measured by liquid scintillation counting at each time point. Identical elimination kinetics were observed (FIG. 10A) even though the carboplatin doses were 100-fold different in concentration (initial $T_{1/2}$=50 minutes for both doses, $C_{max}$=127±30 µM and 1.0+/−0.1 µM for the therapeutic and microdoses, respectively). These data validated the mouse model for subsequent use in xenograft studies.

Tumor Xenograft Experiments

Xenograft mouse tumors consisting of one carboplatin resistant and one sensitive tumor type were established for in vivo evaluation of carboplatin-DNA monoadduct formation and repair in tumor tissue and for in vivo evaluation of tumor response to therapeutic dosing with carboplatin. Tumor xenografts were established in 1-2 month old nude mice by injecting approximately one million cells into the left and right flanks, and allowed to develop tumors of less than 1 cm$^3$ over approximately 4 weeks prior to DNA adduct studies. Mice bearing resistant and sensitive tumors were exposed to either a microdose or therapeutic dose of carboplatin by tail vein injection. DNA isolated from tumor tissue was evaluated for carboplatin-DNA monoadduct frequency levels as a function of time. For tumor response, mice bearing resistant and sensitive tumors were therapeutically treated with a single IV injection of 37.3 mg/kg of carboplatin and then examined for tumor growth as assessed by measuring palpable tumors with a caliper and calculating tumor volume.

A549 cells from a chemoresistant lung cancer cell line, which exhibits extremely low levels of DNA modification when exposed to carboplatin, were injected subcutaneously in mice. Tumor xenografts were resected at different time points post carboplatin treatment, and DNA was extracted and analyzed with AMS to determine the carboplatin-DNA monoadduct frequency. In the first experiment, a titration study was performed to determine how much [$^{14}$C]carboplatin was needed in the mouse model to obtain a sufficiently high signal to noise AMS measurement of [$^{14}$C]carboplatin-DNA monoadducts in extracted mouse tumor DNA. We injected different ratios of [$^{14}$C]carboplatin to unlabeled carboplatin, but with a final concentration of carboplatin either at 2 mg/m$^2$ (microdose) or 200 mg/m$^2$ (Table 3). The tumor xenografts were resected 4 hours after administration of carboplatin. The mice dosed with [$^{14}$C]carboplatin at 50,000 dpm/gram of body mass resulted in a minimal $^{14}$C signal-to-noise (3× background) for quantitative AMS analysis of carboplatin-DNA monoadducts. This radiochemical dose therefore represents the lowest possible animal dose for radiation exposure, since lower doses are insufficient for quantitative AMS analysis of $^{14}$C adducts in DNA.

TABLE 3

Titration of 14C-carboplatin radioactive dose in mice.

| $^{14}$C radioactivity (dpm/gm of body weight) | Signal to Noise (total carboplatin at 2 mg/m$^2$) | | | Signal to Noise (total carboplatin at 200 mg/m$^2$) | | |
|---|---|---|---|---|---|---|
| | Sample #1 | Sample #2 | Mean | Sample #1 | Sample #2 | Mean |
| 50,000 | 3.37 | 3.22 | 3.30 | 787 | 392 | 589 |
| 10,000 | 1.27 | 1.19 | 1.23 | 37.6 | 42.2 | 40 |
| 5,000 | 0.24 | 0.14 | 0.19 | 161 | 54.5 | 108 |

Figure 10B:
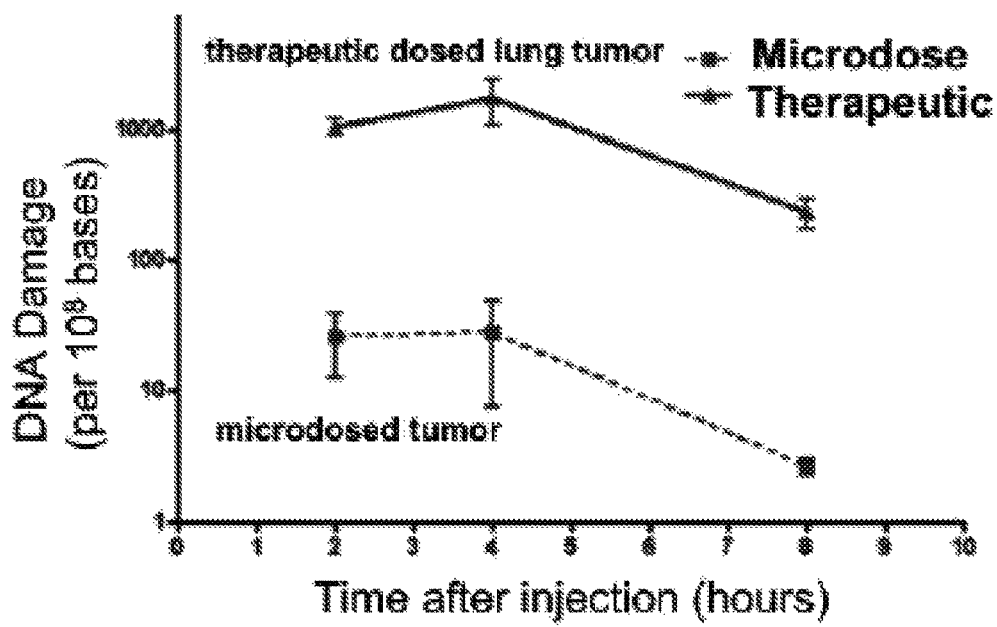

Carboplatin-DNA monoadduct formation in tumor tissue was assessed in vivo using the mouse model. When tumor xenografts were approximately 1 cm in diameter, the mice were given either one microdose of [$^{14}$C]carboplatin (2 mg/m$^2$ of body surface area (BSA)) or a therapeutic dose (200 mg/m$^2$ of BSA). Mice were sacrificed at 2, 4 and 8 hour time points (n=5 for each experimental group). Approximately 10 mg of tissue from each tumor was harvested and DNA was isolated for AMS analysis. The mouse tumor DNA adduct frequencies are plotted vs time after injection (FIG. 10B). As with the cell culture data, the kinetics of carboplatin-DNA adduct formation and repair in tumor tissue are nearly identical for both the microdose and the therapeutic dose in this mouse model. Carboplatin-DNA monoadduct levels in xenograft tumor DNA are proportional to IV dose of carboplatin in the mouse model.

Figures 10C, 10D:
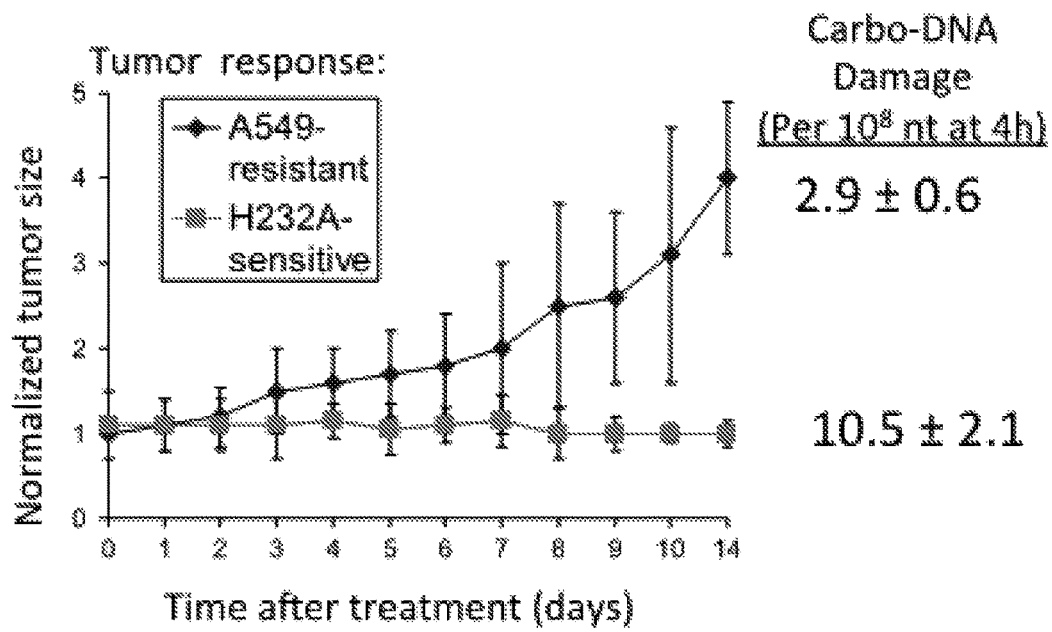

Mice xenografted with sensitive (H232A) and resistant (A549) lung cancer cell lines were infused with a therapeutic dose of carboplatin to assess tumor response. The tumors were measured daily over 14 days post infusion (FIG. 10C). Tumor size was normalized as the ratio of tumor diameter to the tumor diameter measured on day 0 (no change=1.0). All experiments were performed at least in triplicate. Area under the curve for microdose-induced carboplatin-DNA adducts for each tumor type was determined 4 hours post microdosing. The resistant A549 tumor xenograph continued to grow after chemotherapy, while the sensitive H23 2A tumor xenograph did not display any growth. In a separate group of mice, the levels of microdose-induced carboplatin-DNA monoadducts at 4 h post microdosing were measured and found to correlated with the above tumor response, as expected. This data demonstrates that in vivo, microdose-induced carboplatin-DNA monoadduct levels correlate with tumor response for carboplatin treatment in the mouse model.

DNA repair rates in the xenograft tumor cells were also observed to correlate with carboplatin resistance. This is exemplified by the measurement of DNA repair in the A549 and H232A tumor xenografts (FIG. 10D). Four hours after a microdose was administered to three mice each with A549 and H232A tumor xenografts, the animals were sacrificed and tumors were excised. Tissue from each tumor was minced with a scalpel and washed with PBS. Half of the sample was frozen immediately (control) and half was incubated in cell culture medium (no carboplatin) for 8 hours prior to storage. DNA was extracted from the two sets of experiments and analyzed for carboplatin-DNA monoadducts. The resistant A549 cell line had 4±3% of the carboplatin-DNA monoadducts remaining compared to the control, whereas 56±8% of the monoadducts persisted for the drug sensitive H23 cells. These data indicate that a significant amount of repair can occur within the first 24 hrs after monoadducts are formed in selective tumors, and that DNA repair rates can be useful indicators of chemoresistance.

Example 5

Human Studies with a [$^{14}$C]Carboplatin Diagnostic Reagent

Radiolabeled carboplatin containing C$^{14}$ carbon atoms in the cyclobutane dicarboxylic acid group was formulated for human use as a sterile, pyrogen free solution at 5 mg/mL in water. This reagent was found to be stable upon storage at −20° C. (<2% loss of radiopurity per year) and stable to free/thaw with no observed precipitation of the drug upon freezing. Microdoses of the [$^{14}$C]Carboplatin were administered to human cancer patients as a diagnostic reagent, followed by full dose platinum-based chemotherapy and evaluation of response. Within four weeks of the [$^{14}$C]carboplatin microdose, these patients received standard of care chemotherapy for their disease, which included either carboplatin or cisplatin. The patient population consisted of non-small cell lung cancer patients (NSCLC), stage IV with measurable lesions, and bladder transitional cell carcinoma (TCC) patients, stage II disease and above for neoadjuvant treatment, or stage III and IV metastatic disease with measurable lesions for palliative chemotherapy. Patients were identified for this study as having measurable lesions using the Response Evaluation Criteria in Solid Tumor (RECIST), an Eastern Cooperative Oncology Group performance status of ≤2, and adequate bone marrow and vital organ function. PBMC and tumor tissue were collected from the patients for analysis of carboplatin-DNA monoadduct frequencies. Toxicity of the [$^{14}$C]carboplatin diagnostic reagent administered as a microdose was assessed using Common Terminology Criteria for Adverse Events (CTCAE). Toxicities of grade 3 and above were also collected for patient specific toxic response to full dose chemotherapy for correlation analysis to carboplatin-DNA monoadduct frequency. Patient response to chemotherapy was evaluated using the RECIST for correlation to carboplatin-DNA monoadduct frequency.

Based upon the previous mouse studies that identified a minimal microdose for accurate AMS analysis of carboplatin monoadducts (1% of therapeutic carboplatin containing 50,000 DPM/gm of mouse body weight), the first in-human evaluation of microdose [$^{14}$C]carboplatin was conducted at this same equivalent formulation. The mouse radioactive dose (50,000 DPM/gm), adjusted for body surface area differences between mouse and humans, is equivalent to a dose of $1.0 \times 10^7$ DPM/kg of human body weight. The carboplatin dose for human chemotherapy is personalized to a patient's size and kidney function and is calculated using the Calvert formula with an AUC of 6 (Calvert, A. H., et al. "Carboplatin dosage: prospective evaluation of a simple formula based on renal function." *Journal of Clinical Oncology* 7.11 (1989): 1748-1756). Therefore, individual patients were given a microdose of [$^{14}$C]carboplatin containing a total carboplatin dose at 1% of their therapeutic dose and containing $1.0 \times 10^7$ DPM/kg of body weight of [$^{14}$C]carboplatin. Unlabeled carboplatin and [14C]carboplatin were mixed just before dosing to achieve the required microdose, and injected through the peripheral vein at one arm. Peripheral blood specimens (3 mL or 6 mL) were drawn into BD Vacutainer CPT™ tubes with sodium heparin (Becton Dickinson products #362753) from the other arm at specific time points before and after the administration of the microdose to determine the appropriate collection times for accurate correlation of the microdose to a therapeutic dose outcome in a human patient. After blood collection, the BD Vacutainer CPT™ tubes were gently inverted several times to ensure mixing with heparin anticoagulant. The tubes were immediately placed on ice or stored at 4° C. and then processed within 2 hours of collection to separate plasma and PBMC. For processing, the blood filled BD Vacutainer CPT™ tubes were centrifuged at room temperature in a horizontal rotor for 25 minutes at 1600×g. The top plasma layer was transferred to separate tubes and stored at or below −70° C. After most of the plasma was removed from the CPT tube, PBMC were transferred to another tube and washed three times with ice-cold phosphate-buffered solution (PBS). After pelleting the cells and removing the supernatant, the PBMC's were stored frozen at −80° C. until being processed to isolate DNA for determination of the carboplatin-DNA monoadduct frequency. Tumor samples were collected by biopsy or resection approximately 24 hours after administration of the [$^{14}$C]carboplatin microdose. These tumor specimens were placed in ice immediately after being obtained, washed three times with ice-cold PBS, and stored at or below −20° C. within 2 hours of collection. These frozen tumor samples were then processed at a later time to isolate DNA for determination of the carboplatin-DNA monoadduct frequency. To isolate DNA, tumor tissue was placed on ice in a sterile petri dish and minced with a sterile scalpel for approximately 30-90 sec per sample. Approximately 20-100 mg of tissue was then processed using the modified Wizard DNA isolation protocol as described previously.

The dose of carboplatin in the human diagnostic microdose study was targeted to be to minimize patient exposure to the drug and to result in AMS measurable carboplatin-DNA monoadducts in patient samples. Preclinical cell culture and animal studies identified a minimum concentration and radiochemical specific activity that allows for detection of [$^{14}$C]carboplatin-DNA monoadducts in microgram quantities of DNA. When this microdose formulation (1% of the therapeutic dose based upon the Calvert formula containing [$^{14}$C]carboplatin at $1.0 \times 10^7$ DPM/kg of body weight) was given to the first nineteen patients, the lowest DNA monoadduct level observed was 0.05 adducts per $10^8$ nucleotides (~3.2 monoadducts per cell), with a $^{14}$C signal of less than 1.5 times the background, which is at the limit of quantitation for the AMS detection method.

Example 6

Human Pharmacokinetics of a Microdose of [$^{14}$C]carboplatin and kinetics of microdose induced carboplatin-DNA monoadduct formation in PBMC Although the pharmacokinetics of carboplatin are well known for therapeutic doses, it is not known if human pharmacokinetic parameters obtained using a microdose of carboplatin will track those obtained with therapeutic carboplatin dosing. Here we preformed pharmacokinetic studies after administration of a microdose of [$^{14}$C]carboplatin and also after administration of a therapeutic dose (also containing the same $1.0 \times 10^7$ DPM/kg of body weight of [$^{14}$C]carboplatin) in the same patients to establish that a patient's plasma exposure with a microdose of carboplatin will predict a patient's plasma exposure to a therapeutic dose of carboplatin. This is a requirement for this diagnostic assay to be predictive of response to a therapeutic dose. The pharmacokinetics of microdose carboplatin were also measured in several different patients along with the kinetics of carboplatin-DNA monoadduct formation and repair in PBMC to establish that 24 hours post administration of a microdose of carboplatin is an appropriate time for sampling a patient for this predictive diagnostic assay.

Figures 11A, 11B:
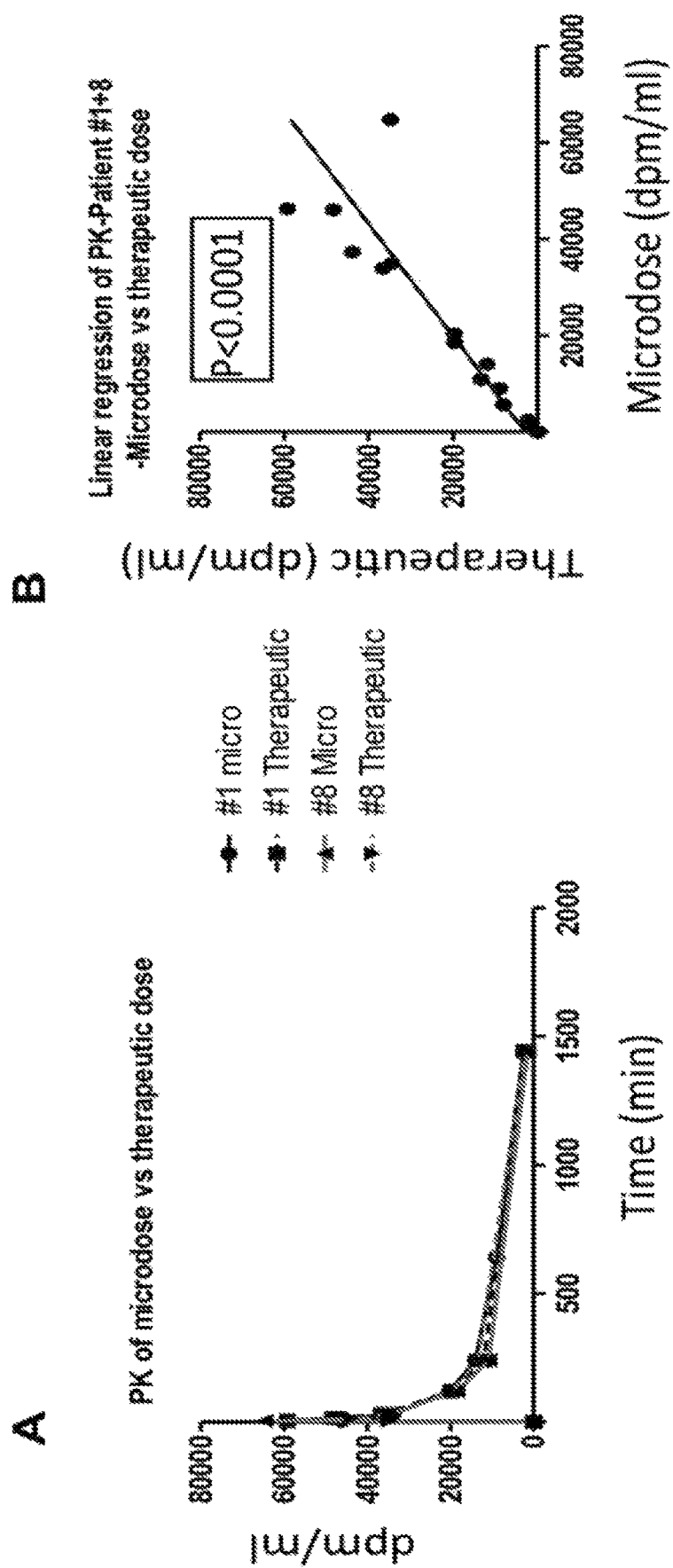
FIG. 11 shows carboplatin DNA-adduct frequency at microdoses and therapeutic doses from two patients (patient #1 and patient #8). The therapeutic dose and the microdose both had equivalent amounts of $^{14}$C label, but varied total drug concentration. a) Plasma elimination kinetics for each patient and dose type b) Linear regression analysis of plasma carboplatin as measured by liquid scintillation counting.

Two of the bladder cancer patients received two doses of [$^{14}$C]carboplatin, including the initial diagnostic microdose and a second microdose at the time of full therapeutic dose. This allowed us to compare the pharmacokinetics of carboplatin in plasma after both microdosing and therapeutic dosing (FIG. 11A). Blood samples were collected at −5 min, 5 min, 15 min, 30 min, 2 h, 4 h, 8 h and 24 h post injection, and immediately processed to obtain the plasma fraction. The resulting PK data, as measured by liquid scintillation counting, showed nearly identical elimination kinetics in plasma (less than 2-fold difference between therapeutic and microdoses). A linear regression analysis of this data shows that the plasma concentrations between the two doses are statistically correlated (p<0.0001) over the 24 hour collection period (FIG. 11B). Therefore, microdosing and therapeutic dosing yield similar carboplatin pharmacokinetics in human patients. The equivalence in plasma PK data suggests that diagnostic microdosing may therefore be useful as a tool to predict PK of therapeutic carboplatin for personalized dosing.

Optimal Sample Collection Time Post Microdose Administration

Figure 12A:
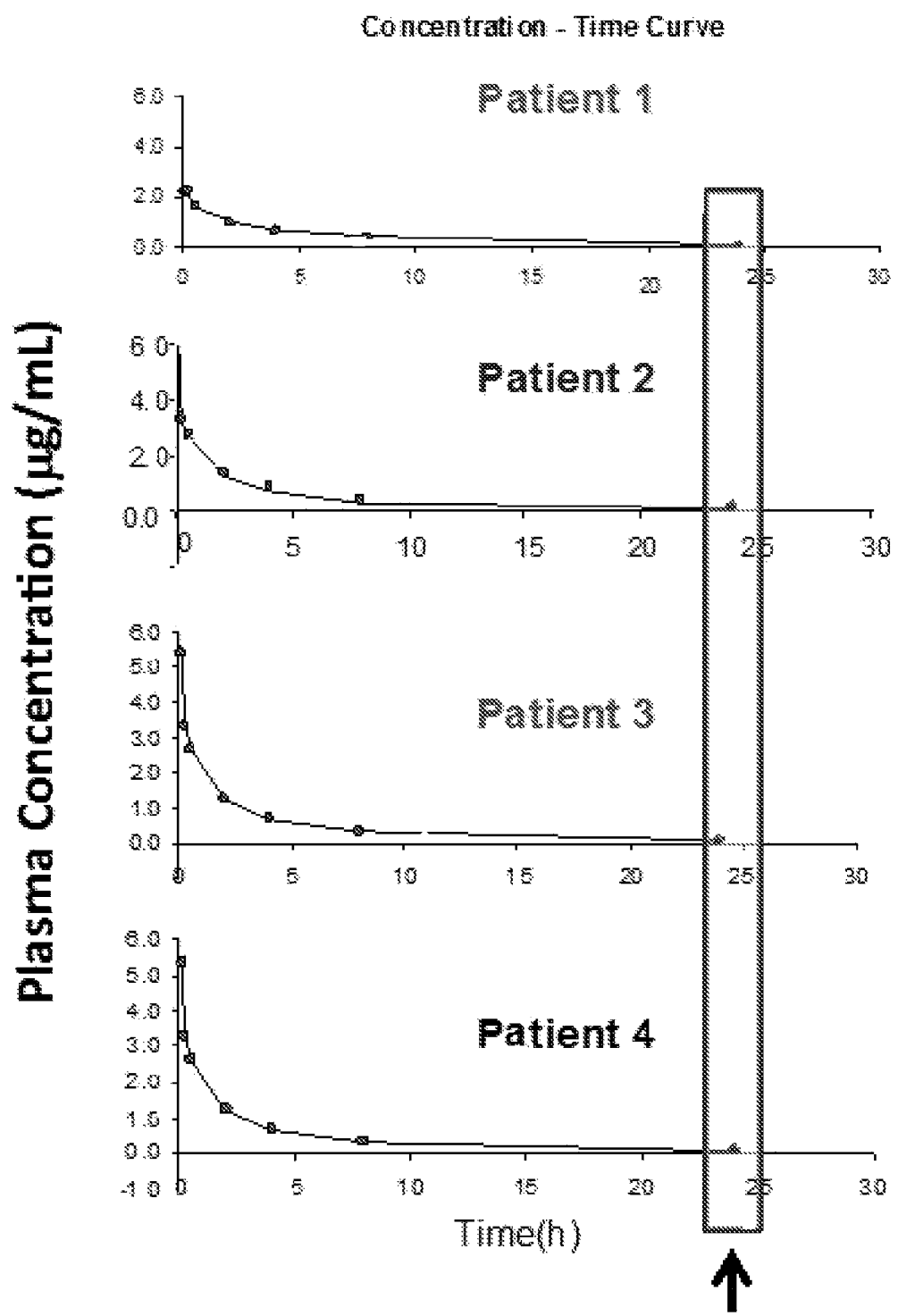
FIG. 12 shows $^{14}$C-labeled carboplatin in blood serum over 24 hours in four human cancer patients. A) PK of carboplatin in four patients from 0-24 hours after receiving a microdose of [$^{14}$C]carboplatin and B) time course for monoadduct formation and loss in PBMC of human cancer patients receiving a microdose of [$^{14}$C]carboplatin.
Figure 12B:
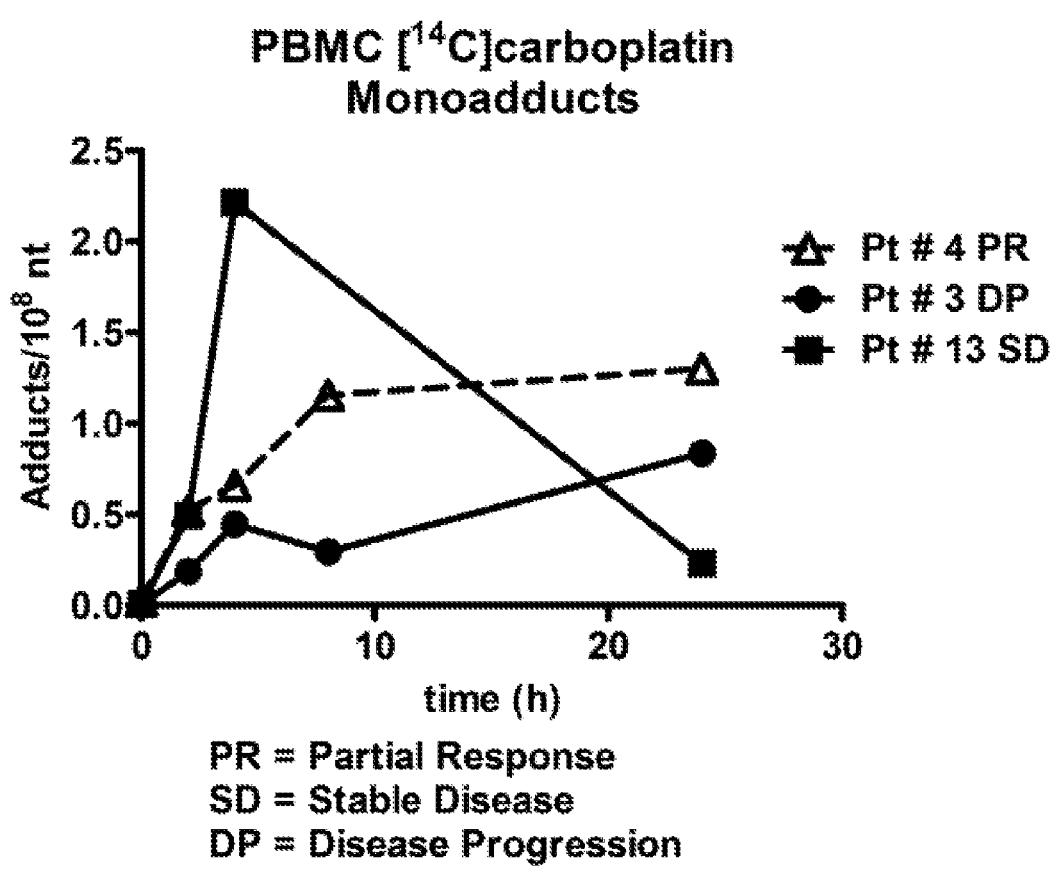

The pharmacokinetics of carboplatin administered as a microdose was assessed in four patients (two with bladder cancer and two with NSLC) for the purpose of comparing interpatient variability and establishing the optimum time point for tumor biopsy sample acquisition. Plasma samples collected at −5 min, 5 min, 15 min, 30 min, 2 h, 4 h, 8 h and 24 h post microdose injection were analyzed by liquid scintillation counting (FIG. 12A) The disintegrations per minute in the sample and specific activity of the microdose formulation were used to calculate the concentration of drug in each plasma sample in μg carboplatin (equivalent) per mL of plasma. The plasma concentration of drug decreased with a half-life of a few hours, and was essentially cleared from the blood within 24 h. FIG. 12B shows that carboplatin-DNA monoadducts in PBMCs continued to accumulate to at least 24 hr in some patients even though the plasma was cleared of carboplatin, suggesting that intracellular carboplatin was still present and active.

This result is in contrast to the cell culture where carboplatin monoadducts are observed to decrease in cell cultures immediately after removal of extracellular carboplatin or a few hours after exposure to a microdose. This shows that the cell culture data, while useful for development, do not necessarily predict the extent of DNA modification by carboplatin in human cancer patients.

Also shown in FIG. 12B is that in one patient with an initial high level of carboplatin-DNA monoadducts, a substantial portion of this damage was repaired by 24 hrs, which is likely a contributing factor to resistance. Overall, the plasma PK and time course of carboplatin-DNA monoadduct formation in PBMC allowed determination of the best time to dose patients prior to biopsy in order to maximize the carboplatin-DNA monoadduct formation, allow for repair in those patients with high repair capacity, minimize the risk of radioactive contamination of PBMC and tumor samples, and also minimize the risk of radioactive contamination of the operating room by blood-borne radiocarbon. Thus, we identified 24 h after administration of the microdose as an optimal time point for collection of tumor tissue for analysis of carboplatin-DNA monoadducts.

PBMC Carboplatin-DNA Monoadduct Levels and Correlation with Therapeutic Outcome

Figure 13:
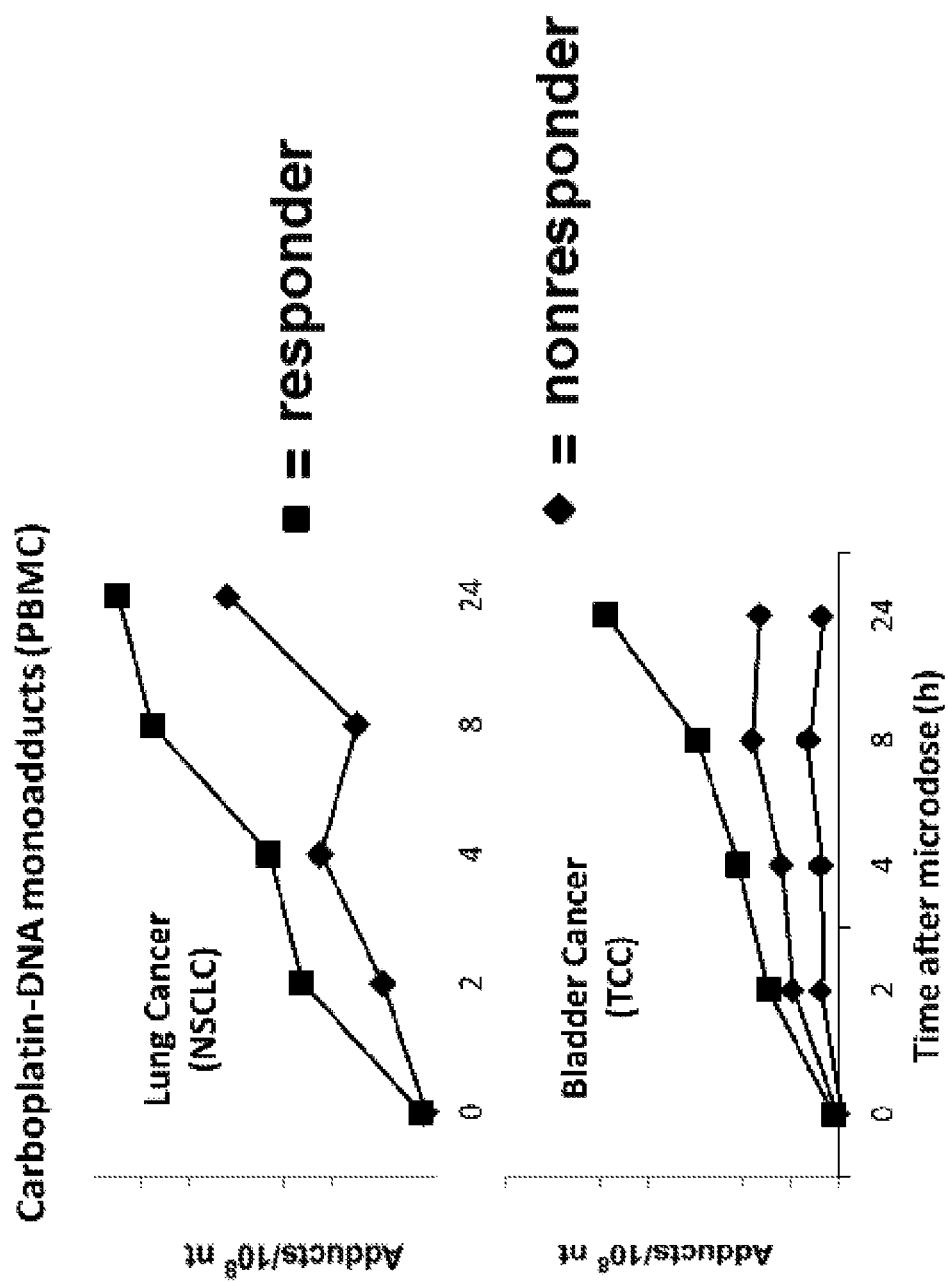
FIG. 13 shows microdose-induced carboplatin-DNA monoadduct data from PBMC of lung and bladder cancer patients compared to response after subsequent platinum-based chemotherapy.

Two lung and three bladder cancer patients were monitored post carboplatin therapeutic treatment to determine therapeutic outcome. Each patient was given a microdose of [$^{14}$C]carboplatin by IV injection. The microdose was 1% of therapeutic based upon Calvert calculation and formulated with [$^{14}$C]carboplatin at $1.0 \times 10^7$ DPM/kg of body weight. At time points of 2, 4, 8 and 24 hours, blood samples were taken from which PBMCs were isolated determination of carboplatin-DNA monoadduct frequency, and expressed as carboplatin-DNA monoadducts per $10^8$ nucleotides (FIG. 13).

Within four weeks after the microdosing procedure, the patients began platinum-based chemotherapy and were followed for response over approximately two months. Of the two NSCLC patients, the one with higher 24-hr monoadduct level had partial response and the lower one had disease progression. Of the three bladder cancer patients, the one with the highest monoadduct level had complete remission, the one in the middle had partial response and the one with the lowest monoadduct level had disease progression. As shown in FIG. 13, there was an overall trend for an increase in microdose-induced monoadduct formation in PBMCs for responders over 24 hours. Thus, the range of carboplatin-DNA monoadduct frequency measured is clinically useful for predicting therapeutic response to carboplatin.

Example 7

Range of Carboplatin-DNA Monoadduct Frequency in Patients Tissues at Specific Time Points after Microdose As we have shown in cell culture and mouse tumor xenograph experiments, the carboplatin-DNA monoadduct frequency is proportional to the dose and time integrated exposure to carboplatin. In this example we establish the useful range of carboplatin-DNA monoadduct frequencies in cancer patients receiving 1% of their therapeutic dose of carboplatin at a fixed time after microdose exposure. Nineteen lung and bladder patients were given a microdose of [$^{14}$C]carboplatin (1% of therapeutic dose containing $1.0 \times 10^7$ DPM/kg of body weight of [$^{14}$C]carboplatin). DNA from PBMC and tumor tissue was extracted and analyzed by AMS for carboplatin-DNA monoadduct frequency. The results of this analysis shown in Table 4. Carboplatin-DNA monoadducts in the range of 0.08 to 1.3 adducts per $10^8$ nucleotides (5 to 83 adducts per human genome) were observed in PBMCs after microdosing (2 to 24 hr time period). Tumor carboplatin-DNA monoadduct frequencies ranged from 0.3 and 42.5 adducts per $10^8$ nucleotides.

TABLE 4

Carboplatin-DNA monoadduct frequencies in PBMC and Tumor Tissue in patients at fixed times

| # | Cancer | 4 h adducts PBMC (per $10^8$ nt) | 24 h adducts PBMC (per $10^8$ nt) | 24 h adducts Tumor (per $10^8$ nt) | Treatment | Response |
|---|---|---|---|---|---|---|
| 1 | Bladder | 0.239 | 0.329 | — | Gemzar/Carboplatin | PR |
| 2 | Bladder | 0.421 | 0.978 | — | Gemzar/Cisplatin | CR |
| 3 | NSCLC | 0.447 | 0.837 | — | Paclitaxel/Carb | DP |
| 4 | NSCLC | 0.662 | 1.3 | — | Paclitaxel/Carb | PR |
| 5 | Bladder | 1.113 | 0.443 | 20.2 | No chemo, NMIBC | — |
| 6 | NSCLC | 0.386 | 0.454 | 0.87 | No | — |
| 7 | NSCLC | 0.587 | 0.942 | 0.66 | No | — |
| 8 | Bladder | 0.265 | 0.081 | 14.8 | Gemzar/Carboplatin | DP |
| 9 | Hodgkin* | 0.861 | 0.472 | 4.58 | No | Not lung cancer |
| 10 | Bladder | 0.545 | 0.930 | 5.37 | Gemzar/Carboplatin | CR |
| 11 | Bladder | 0.184 | 0.154 | 3.13 | MVAC | CR |
| 12 | NSCLC | 0.234 | 0.342 | 1.3 | No | — |
| 13 | NSCLC | 2.214 | 0.232 | — | Carbo/Alitma | SD |
| 14 | Bladder | 0.193 | 0.283 | 0.31 | DD MAVC | DP |
| 15 | Bladder | 1.004 | 0.968 | 42.5 | Gemzar/Carboplatin | CR |

TABLE 4-continued

Carboplatin-DNA monoadduct frequencies in PBMC and Tumor Tissue in patients at fixed times

| # | Cancer | 4 h adducts PBMC (per $10^8$ nt) | 24 h adducts PBMC (per $10^8$ nt) | 24 h adducts Tumor (per $10^8$ nt) | Treatment | Response |
|---|--------|---------------------------------|-----------------------------------|------------------------------------|-----------|----------|
| 16 | Bladder | 0.600 | 0.499 | 8.79 | no chemo, NMIBC | — |
| 17 | Bladder | 1.399 | 0.485 | — | MVAC | DP |
| 18 | Bladder | 0.599 | — | — | no chemo, kidney failure | |
| 19 | Bladder | | | 0.923 | MVAC | PR |

MVAC = Methotrexate, vinblastine, Adriamycin and cisplatin combination treatment
Gemzar/Carb = gemcitabine and carboplatin treatment
Paclitaxel/Carb = paclitaxel/carboplatin
Alitma = pemetrexed treatment
PR = partial response;
CR = complete response;
DP = disease progression
*This was initially misdiagnosed prior to biopsy.

Based on our findings, AMS measurements provide quantitative data assessing carboplatin-DNA monoadducts in humans given microdoses of a chemotherapeutic agent. AMS was sensitive enough to measure the very low level of monoadducts (a few adducts per cell) expected in human tissue after microdosing with a radiolabeled DNA chemotherapeutic agent. Furthermore, the data shows that the carboplatin-DNA monoadduct frequency range that occurs in human tissue after carboplatin microdosing is about 5 to 2550 carboplatin-DNA monoadducts per human genome.

Example 8

Safety of 1 $^{14}$C]carboplatin administered as a microdose

The dose of carboplatin in the diagnostic microdose was chosen to be sub-toxic and non-therapeutic, to minimize patient chemical and radiation exposure, and to result in AMS measurable carboplatin-DNA monoadducts. Nineteen patients have been administered at least one microdose of [$^{14}$C]carboplatin via IV infusion as a diagnostic reagent. Patient toxicity related to the microdose was monitored from the time of IV microdose until the patients received their first chemotherapy. The radiolabeled microdose was well tolerated. None of the clinical side effects associated with standard therapeutic doses of carboplatin were observed. Three of these patients received an additional microdose of [$^{14}$C]carboplatin during administration of therapeutic carboplatin for the purpose of obtaining pharmacokinetics data. In these three cases, [$^{14}$C]carboplatin was administered immediately after, but was separated from, the infusion of a therapeutic dose of carboplatin. In these three cases for which [$^{14}$C]carboplatin was given after therapeutic carboplatin, the toxicity was not different from other cycles of chemotherapy when therapeutic carboplatin was given without [$^{14}$C]carboplatin. Therefore, the microdosing concentration of [$^{14}$C]carboplatin (1% of the therapeutic dose) appears to be clinically non-toxic with respect to chemical exposure. In addition, no patient toxicities associated with radiation exposure were observed. The radiation exposure due the IV administration of $1.0 \times 10^7$ DPM/kg of body weight of [$^{14}$C]carboplatin is comparable to other diagnostic procedures that are considered safe. The total radioactive dose given to a 75 kg patient after an IV microdose of [$^{14}$C]carboplatin is calculated to be 338 µCi. Using an exposure of 20 hours (5 half-lives of 4 hours=20 hours of exposure), this conservatively calculates to a total patient radiation exposure of $9.5 \times 10^{-5}$ joules/kg, which is approximately 0.1 mSv. The annual effective radiation dose equivalent from natural internal sources is 1.6 mSv per person. The radiation exposure for an abdominal CT scan is 10 mSv. The radiation exposure to 14C from administration of this microdose diagnostic reagent is 0.1 mSv±10 mSv=1% of an abdominal CT scan, which is generally considered as a safe radiation dose for diagnostic procedures.

Example 9

Carboplatin Microdose Administration to Cancer Patients and Database Creation

Cancer patients will be administered a microdose of [$^{14}$C] carboplatin by IV injection. The microdose will comprise a dose of [$^{14}$C] carboplatin that is 1% of the therapeutic dose for the patient as determined by Calvert's formula. The microdose will comprise around $1.0 \times 10^7$ DPM/kg of patient bodyweight, corresponding to a specific activity of about 17.7 mCi/mM in the microdose formulation. A 6 mL blood sample will be obtained immediately prior to IV administration of a carboplatin microdose. A second 6 mL blood sample will be taken 24 h after microdose administration, followed by a single biopsy sample. DNA will be isolated from the blood and tumor samples. DNA analysis will be performed by UV spectrophotometry and AMS to determine the frequency of $^{14}$Ccarboplatin-DNA monoadducts in each sample as described herein.

As early as two days after the microdose procedure, but no more than four to twelve weeks after, patients will begin carboplatin or cisplatin chemotherapy in order to collect patient response and toxicity data. For this study, tumor response and radiographic disease progression is defined as progressive disease using RECIST 1.1 for soft tissue disease or by appearance of two or more new lesions. From this, we will determine if carboplatin-DNA monoadducts induced by carboplatin microdosing in tumor tissue and peripheral blood mononuclear cells (PBMCs) correlate with an objective response to platinum-based chemotherapy.

Statistically, differences between responders and non-responders with respect to carboplatin-DNA monoadduct formation will be demonstrated by disproving the null hypothesis that the difference of means of adduct levels between responders and nonresponders do not differ. We will compare the mean level of monoadducts in responders to chemotherapy to that of non-responders using a 2-sample t-test at the 0.05 level (2-sided). If the result is statistically significant, we will consider the use of monoadducts levels in PBMC or tumor tissue feasible for treatment stratification. This will statistically demonstrate a range of clinically useful carboplatin monoadduct frequencies that may be used to determine a correlation between adduct frequency and likelihood of response to therapeutic administration of carboplatin or cisplatin. The clinically useful adduct frequency range will be between 0.1 and 60 adducts per $10^8$ nucleotides.

The Youden index will be used to estimate the optimal cut-point differentiating responders from non-responders. This cut-point is the midpoint between the mean level of responders and the mean level of non-responders for normally distributed data with equal variance (Perkins & Schisterman, "The Youden Index and the optimal cut-point corrected for measurement error", Biom J. 2005 47(4):428-41). This may be used as a threshold adduct frequency above which patients are expected to respond to therapy. The threshold will be in the range of 0.1 and 3 adducts per $10^8$ nucleotides for PBMC and 0.1 and 60 adducts per $10^8$ nucleotides for tumor.

Figure 14:
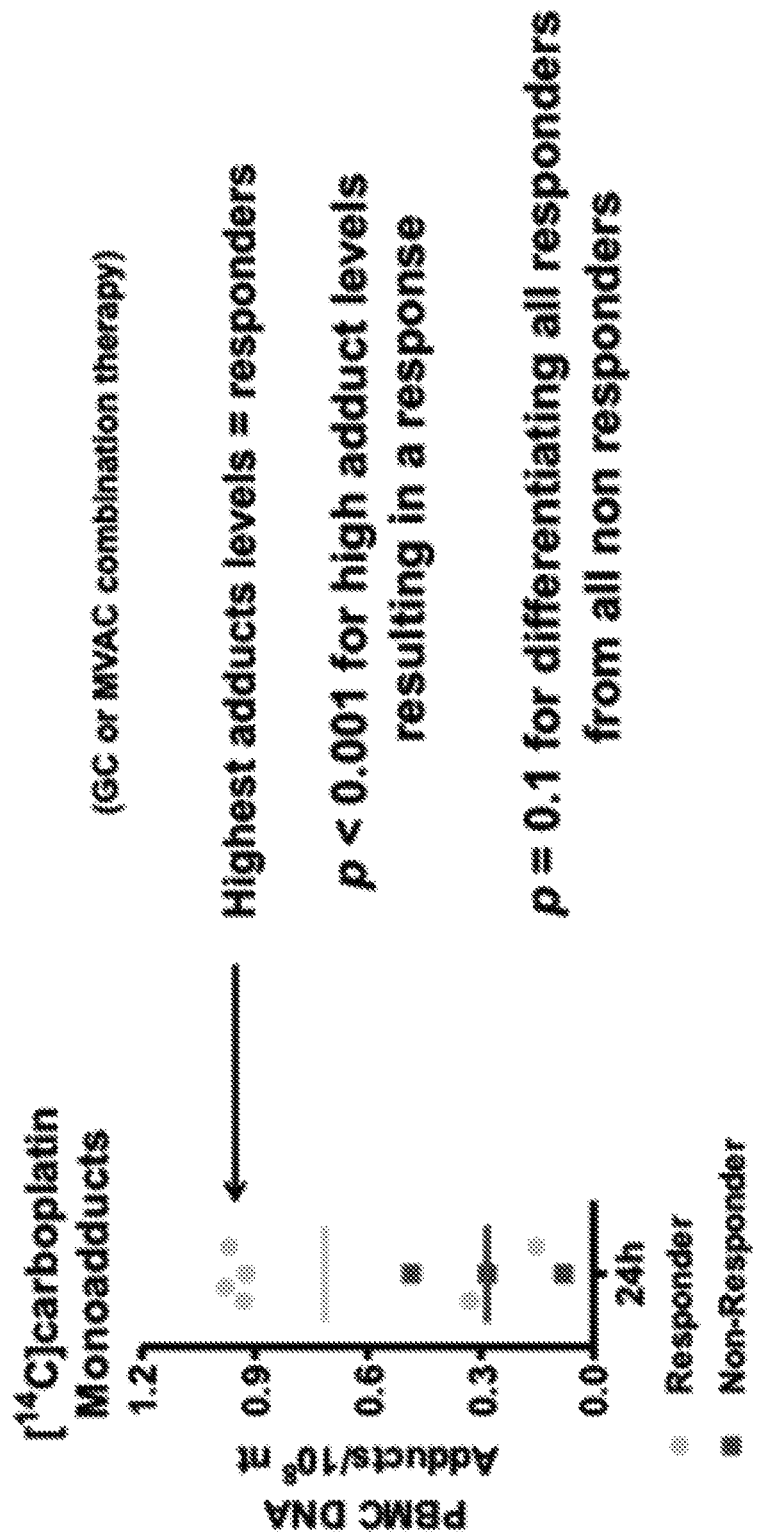
FIG. 14 shows a database of microdose induced carboplatin-DNA monoadduct frequencies vs. patient response to carboplatin- or cisplatin-based standard chemotherapy for nine bladder cancer patients. Responders (circles) and non-responders (squares) are shown along with the means (lines) for their respective distributions.

FIG. 14 is a database of microdose induced carboplatin DNA adduct frequencies vs. patient response to carboplatin- or cisplatin-based standard chemotherapy for bladder cancer patients. Data obtained with PBMC's from nine bladder cancer patients for which response data is known show a trend for responders to have higher drug-DNA adduct frequencies. Specifically, all of the patients whose PBMC had 24 hour adducts levels greater than 0.6 per $10^8$ nucleotides were responders (p<0.001) compared to all patients with lower adduct levels. With respect to overall differentiation of responders and nonresponders, there was a difference in the mean adduct level values between the two groups with approximately a 90% probablility of statistical significance (p=0.1). This data validates the use of PBMC as surrogates for tumor tissue in bladder cancer patients.

For this study, toxic response to full dose chemotherapy will also be assessed using criteria such as Common Terminology Criteria for Adverse Events (CTCAE). From this, we will determine if carboplatin-DNA monoadducts induced by carboplatin microdosing in tumor tissue and peripheral blood mononuclear cells (PBMCs) correlate with toxic response to platinum-based chemotherapy.

Although we have previously determined an optimal time point of tissue or blood collection at 24 hours after microdose administration, the method described herein may also be performed at alternative time points of tissue or blood collection after administration of a microdose, e.g., at a time point from 4-48 hours. The correlation of monoadduct frequency to treatment outcome probability is dependent upon this timepoint.

The dose of the radiolabeled carboplatin administered from the microdose formulation may also be adjusted within a range that is non-toxic to the patient, e.g., from 0.1-10% of a therapeutic dose. The correlation of monoadduct frequency to treatment outcome probability is dependent upon the initial dose of the radiolabeled carboplatin administered to the patient.

The correlation of adduct frequency with treatment outcome may also depend upon the type of tumor the patient has. The database will distinguish adduct frequency correlations to treatment outcome based on cancer type.

Example 10

Prediction of Therapeutic Outcome in a Patient Administered $^{14}$C Carboplatin Once the adduct frequency correlation with therapeutic outcome is established for the preferred microdose formulation at a preferred time of sample collection after administration for a given tumor type, a non-toxic, in vivo diagnostic assay that predicts patient response to subsequent chemotherapy, and possible toxic response will be performed.

Cancer patients will be administered a microdose of [$^{14}$C] carboplatin by IV injection. The microdose will comprise a dose of [$^{14}$C] carboplatin that is 1% of the therapeutic dose for the patient as determined by Calvert's formula. The microdose will comprise around $1.0 \times 10^7$ DPM/kg of patient bodyweight, corresponding to a specific activity of about 17.7 mCi/mM in the microdose formulation. A 6 mL blood sample will be obtained immediately prior to IV administration of a carboplatin microdose. A second 6 mL blood sample will be taken 24 h after microdose administration, followed by a single biopsy sample. DNA will be isolated from the blood and tumor samples. DNA analysis will be performed by UV spectrophotometry and AMS to determine the frequency of $^{14}$Ccarboplatin-DNA monoadducts in each sample as described herein.

The probability that a cancer will respond to subsequent chemotherapy using the patient's personalized drug-DNA adduct frequency measurement will be determined by comparing the adduct frequency with a clinically derived database specific to the preferred microdose formulation, tissue collection time after administration of the preferred microdose formulation, and cancer and/or tissue type analyzed. A report will be issued to a physician and/or patient about the probability for response to the specific chemotherapy so that a decision to use the specific chemotherapy on the patient can be made.

Example 11

Oxaliplatin Microdosing in Bladder Cancer Cell Lines

Correlation of Total Oxaliplatin-DNA Adducts with Oxaliplatin $IC_{50}$ in Cell Culture As shown in FIG. 1, a $^{14}$C label in the cyclohexane ring of oxaliplatin is present in both oxaliplatin-DNA monoadducts and oxaliplatin-DNA diadducts. In this example, five bladder cancer cell lines were treated in cell culture with [$^{14}$C]oxaliplatin. Oxaliplatin-DNA adducts, both monoadducts and diadducts combined, were determined over time by measuring the $^{14}$C content in genomic DNA using AMS. Cellular sensitivity to oxaliplatin was analyzed by the MTT assay. We found (1) that microdoses of [$^{14}$C]oxaliplatin can induce measurable oxaliplatin-DNA adducts, (2) that levels of DNA adducts induced by microdoses are linearly proportional to the DNA damage caused by therapeutic concentrations of oxaliplatin, and (3) that the combined, total oxaliplatin-DNA adduct levels induced by either a microdose or a therapeutic dose correlate to the oxaliplatin $IC_{50}$ of these cell lines in culture.

Five bladder cancer cell lines (5637, T24, TCCSUP, HT1197, and J82) having a wide range of sensitivity to oxaliplatin were tested. The cell lines were purchased from the American Type Culture Collection (ATCC, Manassas, Va.) and cultured in the recommended media. $IC_{50}$ values were determined for each cell line using the MTT assay after incubating cells for 72 hours with different concentrations of oxaliplatin. Oxaliplatin (5 mg/ml) was purchased from Sanofi-Aventis (Bridgewater, N.J., USA). [$^{14}$C]Labeled oxaliplatin ([$^{14}$C]oxaliplatin containing $^{14}$C atoms in the cyclohexane ring (specific activity of 58 mCi/mmol) was purchased from Moravek Biochemicals. Mixtures of [$^{14}$C] oxaliplatin and non-labeled oxaliplatin were used in order to minimize the usage of radiocarbon, and achieve the different specific activities required for this study. Oxaliplatin solutions were prepared immediately prior to use.

Figure 15A:
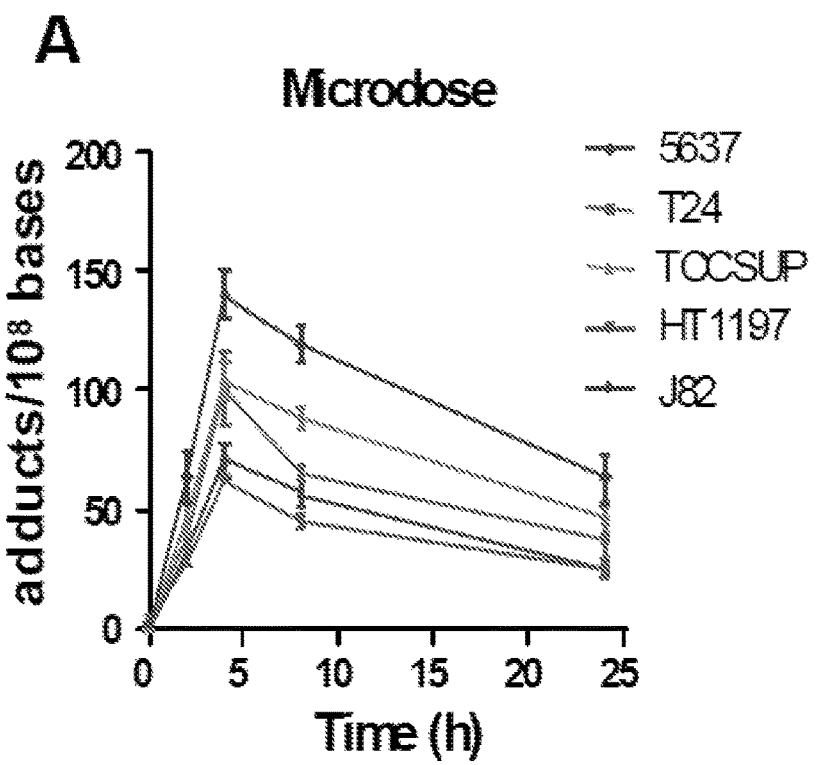
FIG. 15 shows DNA adducts formed after exposure in culture to a relevant microdose concentration or a relevant therapeutic concentration in bladder cancer cells as measured by AMS. A. Oxaliplatin-DNA damage over time in five bladder cancer cell lines exposed to a microdose relevant concentration of [$^{14}$C]oxaliplatin (0.1 µM) for 4 h. B. Oxaliplatin-DNA damage over time in five bladder cancer cell lines exposed to a therapeutically relevant concentration of [$^{14}$C]oxaliplatin (10 µM) for 4 hours. C. Linear regression analysis of the data from A and B. D. Correlation of oxaliplatin chemoresistance ($IC_{50}$) to microdose-induced total oxaliplatin-DNA adducts (both monoadducts and diadducts combined).
Figure 15B:
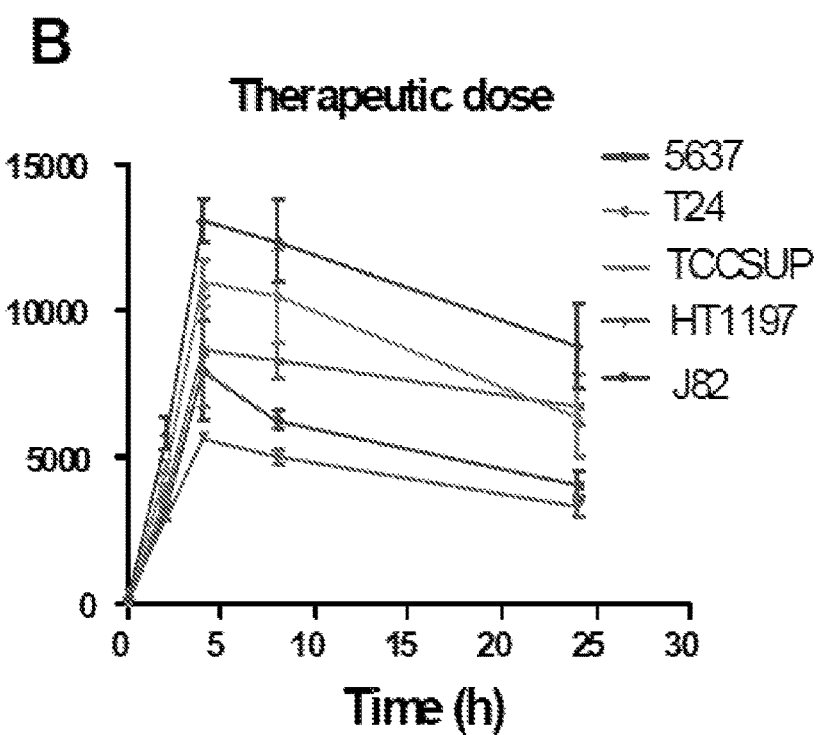
Figure 15C:
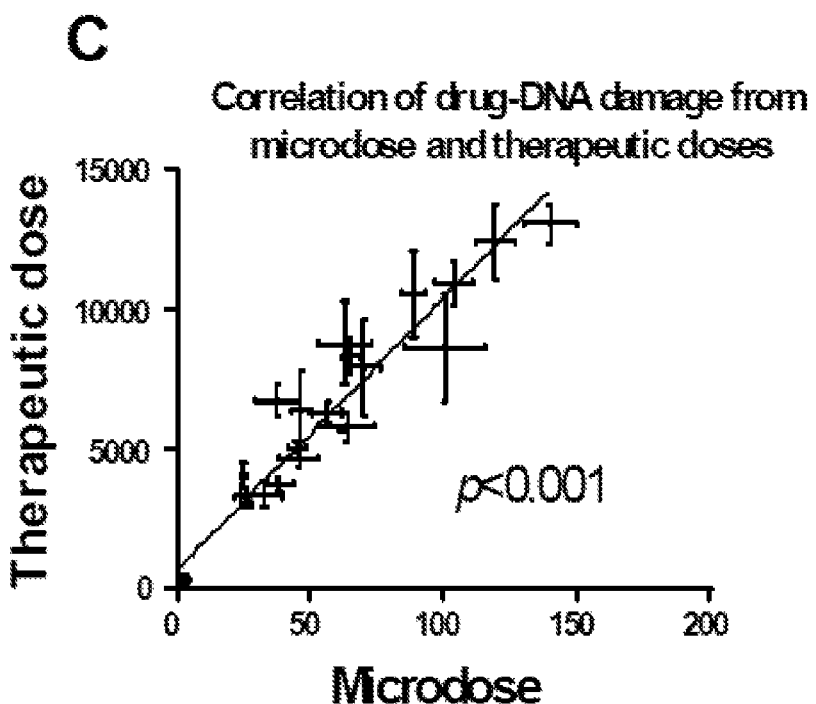
Figure 15D:
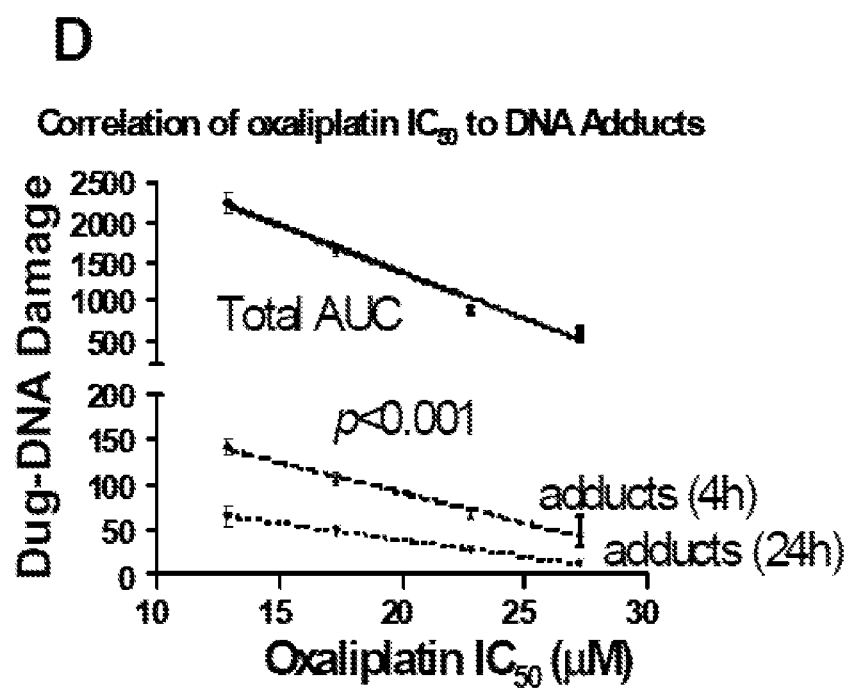

Cells were seeded in 60-mm dishes at a density of $1 \times 10^6$ cells/dish and allowed to attach overnight in a 37° C. humidified atmosphere containing 5% $CO_2$. The plasma $C_{max}$ for oxaliplatin in therapeutically treated patients is about 10 µM. At hour 0, cells were dosed and incubated with 0.1 µM oxaliplatin (a relevant microdose concentration) or 10 µM oxaliplatin (a therapeutically relevant concentration), each supplemented with 0.1 µM [$^{14}$C]oxaliplatin at a final concentration 5,000 dpm/mL. Although the in vivo oxaliplatin half-life is about 16.8 hours, for this example the cells were incubated for 4 hours in the presence of oxaliplatin for direct comparison to the carboplatin data of examples 1 and 2. The cells were then washed twice with phosphate-buffered solution (PBS) and maintained thereafter with oxaliplatin-free culture media. DNA was harvested at hours 0, 2, 4, 8, 24 hours using the modified Wizard procedure described previously. Ten micrograms of DNA per sample was converted to graphite and measured by AMS for $^{14}$C quantification. Triplicate sets of AMS experiments were performed and the data was plotted as time vs oxaliplatin-DNA adducts per $10^8$ nt. FIG. 15A shows the levels of oxaliplatin-DNA adducts induced by incubation with a relevant microdose concentration of oxaliplatin. FIG. 15B shows the levels of oxaliplatin-DNA adducts induced by incubation with a therapeutically relevant concentration of oxaliplatin. Oxaliplatin-DNA monoadducts could be detected in all cell lines at all time points. The dose-response of oxaliplatin-DNA adduct formation was significantly linear at all time points for all cell lines at both microdose and therapeutic doses (FIG. 15C, p<0.001). Therefore, drug-DNA damage from microdoses of oxaliplatin are predictive of the extent of DNA modification caused by the therapeutic dose in cell culture. The DNA damage concentrations ranged from ~50-100 oxaliplatin-DNA adducts per $10^8$ nt for the microdose, and ~5,000-10,000 oxaliplatin-DNA adducts per $10^8$ nt for the therapeutic dose, demonstrating an approximate 100-fold difference in the DNA damage with a 100-fold difference in drug concentration. Both microdosing and therapeutic dosing with [$^{14}$C]oxaliplatin in cell culture resulted in drug-DNA adduct levels that statistically correlate (p<0.001) with the oxaliplatin $IC_{50}$ of the cells to oxaliplatin (FIG. 15D). These data indicate that microdose-induced oxaliplatin adducts are predictive of oxaliplatin chemoresistance. The linear correlation is highly significant for total oxaliplatin-DNA adducts integrated over 24 h (AUC; units are adducts per $10^8$ nucleotides-hr), and for total oxaliplatin-DNA adducts at 4 h and 24 h after dosing (units are adducts per $10^8$ nucleotides).

Compared to the data in examples 1 and 2 using carboplatin, total oxaliplatin-DNA adducts were detectable by AMS with 1/10$^{th}$ of the radioactive dose required for detection of carboplatin-DNA monoadducts (5,000 DPM/mL vs 50,000 DPM/mL). In addition, the observed range of total oxaliplatin-DNA adducts is significantly larger compared to carboplatin-DNA monoadducts with both microdosed induced adducts (~1-15 per$10^8$ nt with carboplatin vs. ~50-100 per$10^8$ nt with oxaliplatin) or therapeutically induced adducts (~100-1500 per$10^8$ nt with carboplatin vs. —5,000-10,000 per$10^8$ nt with oxaliplatin). These differences are not surprising since these two drugs are used at different doses, have different reaction rates with DNA, and an AMS measurement of $^{14}$C in genomic DNA only quantitates monoadducts with carboplatin and both monoadducts and diadducts with oxaliplatin. This data collectively shows that the useful diagnostic range of DNA adducts formed after exposure to a microdose of a chemotherapy agent is dependent on both the drug type and dose, and also dependent upon the types of adducts being measured.

DNA Adduct Formation in Sensitive and Resistant Bladder Cancer Cell Lines-a Model of Acquired Resistance.

We performed a phenotypic analysis of a parental bladder cancer cell line 5637 and a daughter cell line 5637R that has developed resistance to platinum-based drugs by exposure to increasing concentrations of oxaliplatin over several months. The cell lines were tested for cytotoxic response to oxaliplatin using the MTT assay, as well as cytotoxic response to several other commonly used chemotherapy drugs. Drug-DNA adduct formation and repair was measured by accelerator mass spectrometry. In this example we show that an isogenic cell line that has acquired resistance to oxaliplatin can be differentiated from its sensitive parent cell line by measuring total oxaliplatin-DNA adducts after subjecting the cells to a therapeutically relevant concentration of [$^{14}$C]oxaliplatin. We also show that this oxaliplatin resistant cell line is partially resistant to other platinum agents, but susceptible to several other chemotherapy drugs, demonstrating that a predictive oxaliplatin-DNA adduct assay for chemoresistance has utility to direct patients away from oxaliplatin to other potentially useful chemotherapy drugs.

To develop Pt-resistant sub-cell lines, 5637 (HTB-9) cells were cultured around the $IC_{50}$ concentrations of oxaliplatin intermittently with stepwise increase of oxaliplatin concentration. After 10 months of culture, the resistant sub-cell line 5637R was developed. To confirm that 5637 was the original ATCC cell line, and that 5637R originated from the parental 5637 cell line, both cultures were sent to the ATCC Cell Line Authentication Service for cell verification per the ATCC protocol. More specifically, fifteen short tandem repeat (STR) loci plus the gender determining locus, amelogenin, were amplified using the commercially available PowerPlex® 16HS Kit from Promega.

To characterize the oxaliplatin-DNA adduct frequency in these cell lines, cells from each cell line were seeded in 60-mm dishes at a density of $1 \times 10^6$ cells/dish and allowed to attach overnight in a 37° C. humidified atmosphere containing 5% $CO_2$. At hour 0, cells were dosed and incubated 10 µM oxaliplatin (a therapeutically relevant concentration), supplemented with 0.1 µM [14C]oxaliplatin at 5,000 dpm/mL for 24 hours. The 24-hour incubation was used to mimic the average in vivo oxaliplatin half-life (16.8 hours) in patients. The cells were then washed twice with phosphate-buffered solution (PBS) and maintained thereafter with oxaliplatin-free culture media. DNA was harvested at hours 0, 2, 4, 8, 24, 28 and 48 hours using a Promega Wizard DNA Purification Kit. Ten micrograms of DNA per sample was converted to graphite and measured by AMS for $^{14}$C quantification. Triplicate sets of AMS experiments were performed and the data was plotted as time vs oxaliplatin-DNA adducts per $10^8$ nt. For DNA repair studies, the decrease of oxaliplatin-DNA adducts at several time points during the 24 hour culture period without oxaliplatin was used to calculate the drug-DNA adduct repair velocity.

Statistics were calculated with n=3 for each cell line. ANOVA analysis of $IC_{50}$ and AUC data were based on a one-sided t-test.

Figure 16A:
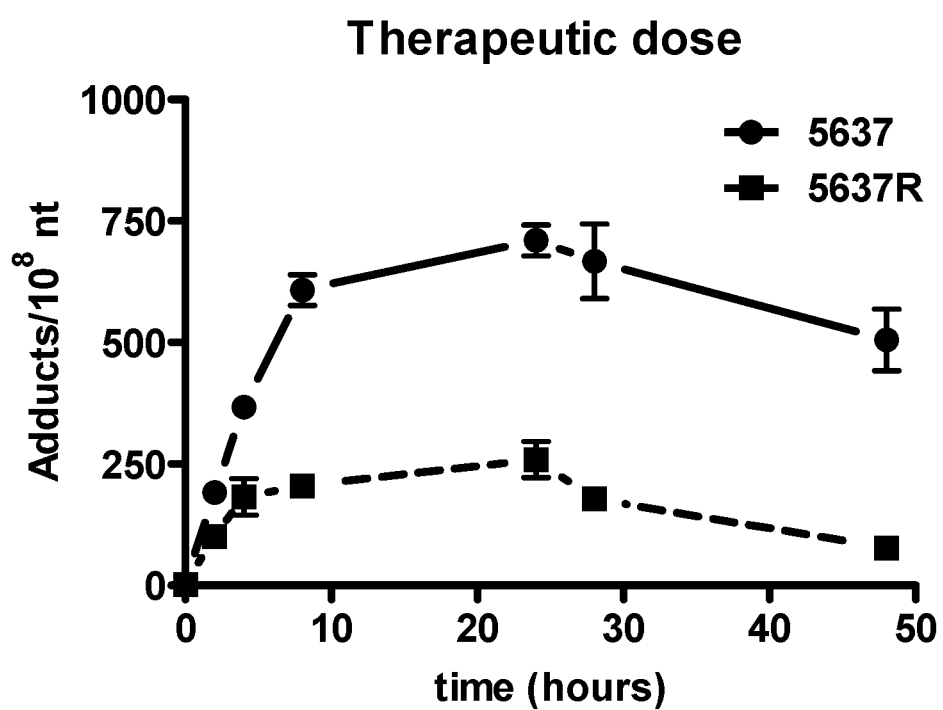
FIG. 16 shows oxaliplatin-DNA adduct data for 5637 and 5637R cells in culture. A) Oxaliplatin-DNA adducts over 48 hours, B) oxaliplatin-DNA adduct formation and repair, C) cytotoxicity data ($IC_{50}$ values) for several commonly used chemotherapy drugs.

First, we confirmed that 5637R originated from the parental 5637 cells by sending one aliquot of each cell line to ATCC for determination of clonal fidelity. The 15 short tandem repeat (STR) loci plus amelogenin of the 5637R cell line used for this study were an exact match for the ATCC human cell line 5637 in the ATCC database. The 5637 line had three alleles that 5637R lacked while all other alleles examined were the same for both cell lines, suggesting that 5637R is a derivative of 5637. Using the MTT assay, the $IC_{50}$ of 5637R to oxaliplatin increased by approximately 10-fold ($IC_{50}$=27.27 µM, p<0.0001) compared to the oxaliplatin $IC_{50}$ of the parental 5637 cell line ($IC_{50}$=2.45 µM). Additionally, we determined that the 5637R cell line formed fewer oxaliplatin-DNA adducts upon drug exposure compared to 5637 cells. Accordingly, [14C]oxaliplatin was used in this study to enable quantitation of oxaliplatin-DNA adduct formation. Cells were cultured with [$^{14}$C]oxaliplatin at 10 µM (the peak human oxaliplatin plasma concentration during chemotherapy) for 24 hours. Cells were sampled for DNA extraction and AMS analysis over 48 hours. There was a time-dependent increase in oxaliplatin during the 24-hour incubation. At all time points, the oxaliplatin-DNA adduct levels in 5637R cells were always lower than the adduct levels in chemosensitive 5637 cells (FIG. 16A). At 24 hours, 5637R cells had much lower DNA adducts than the parental 5637 cells (259.2±37.3 versus 710.0±32.2 adducts per $10^8$ nucleotide, p<0.0001) (FIG. 16B). During the 48 hour study time period, the area under curve (AUC) of oxaliplatin-DNA adducts were 9,426±2457 adducts per $10^8$ nucleotide-hour for 5637R cells, compared to 27,720±2,985 adducts per $10^8$ nucleotide-hour for 5637 cells (p=0.001). Therefore, the chemoresistant 5637R cell line has lower oxaliplatin-induced DNA damage compared to its sensitive parent cell line. 5637R cells had a repair rate of 3.48±0.15 adducts per $10^8$ nucleotide-hour and 1.34±0.30 adducts per $10^8$ nucleotides-hour for 5637 cells (p=0.0004), indicating that DNA repair is a contributing factor to oxaliplatin resistance in the daughter cell line. Substantial repair was observed out to at least 24 hours after removal of oxaliplatin from the culture media, suggesting that single time point sampling for oxaliplatin-DNA adducts should be made at least 48 hours after initial dosing to reflect repair of oxaliplatin adducts in resistant cells.

These two cell lines were also cultured with a range of concentrations of cisplatin, carboplatin, gemcitabine, doxorubicin, methotrexate and vinblastine for 72 hours to determine $IC_{50}$ for these other drugs (FIG. 16C). These drugs were chosen because of their frequent use in the treatment of bladder cancer. The 5637R cell line also displayed some resistant to cisplatin ($IC_{50}$ 2.99 µM for 5637R versus 0.59 µM for 5637, p=0.049) and to carboplatin ($IC_{50}$=72.18 µM for 5637R versus 24.34 µM for 5637, p<0.0001), but to a much lesser extent than for oxaliplatin. It was also more resistant to the antimetabolite drug gemcitabine ($IC_{50}$=1.44 µM for 5637R versus 0.12 µM for the parental 5637, p=0.0015), but was equally sensitive to doxorubicin ($IC_{50}$=0.27 µM for 5637R versus 0.29 µM, p=0.45 for 5637), methotrexate ($IC_{50}$=1.24 µM for 5637R versus 2.01 µM for 5637, p=0.18) and vinblastine ($IC_{50}$=0.61 nM for 5637R versus 0.60 nM for 5637, p=0.48). These results are not surprising considering acquired resistance to one drug often selects for one or more mechanistic pathways that have multiple drugs as substrates. In the clinic, response to first line platinum-based therapy is 40-50% for muscle invasive bladder cancer, but once resistance ensues, subsequent treatments have just 5-10% response rates (Sweeney, Christopher J., et al. "Phase II study of pemetrexed for second-line treatment of transitional cell cancer of the urothelium." *Journal of Clinical Oncology* 24.21 (2006): 3451-3457; Vaughn, David J., et al. "Phase II trial of weekly paclitaxel in patients with previously treated advanced urothelial cancer." *Journal of Clinical Oncology* 20.4 (2002): 937-940). These results clearly show that it is feasible to have substantial cytotoxic response to subsequent chemotherapy after the onset of platinum drug resistance if the correct treatment is selected.

Example 12

Human Pharmacokinetics of a Microdose of 1$^{14}$C]oxaliplatin and Kinetics of Microdose Induced Oxaliplatin-DNA Adduct Formation in PBMC Although the pharmacokinetics of oxaliplatin are well known for therapeutic doses, is not known if human pharmacokinetic parameters obtained using a microdose of oxaliplatin will track those obtained with therapeutic oxaliplatin dosing. Here we established that a patient's plasma exposure to a microdose injection of oxaliplatin is consistent with the known plasma $T_{1/2}$ for oxaliplatin given at therapeutic doses. This relationship is a requirement for a microdose-based diagnostic assay to be predictive of response to a therapeutic dose. The kinetics of microdose induced oxaliplatin-DNA adduct formation and repair in PBMC was also measured in this same patient. This was done to establish that 48 hours post administration of a microdose of oxaliplatin is an appropriate time for sampling a patient for this predictive diagnostic assay to be useful.

We obtained oxaliplatin pharmacokinetic parameters in a metastatic breast cancer patient administered a microdose of [$^{14}$C]oxaliplatin. Single agent oxaliplatin chemotherapy is given by IV at a personalized dose of 130 mg/m$^2$ of body surface area using the Du Bois and Du Bois formula (Du Bois, D., and E. F. Du Bois. "A formula to estimate the approximate surface area if height and weight be known. 1916." Nutrition (Burbank, Los Angeles County, Calif.) 5.5 (1989): 303).

Figure 17A:
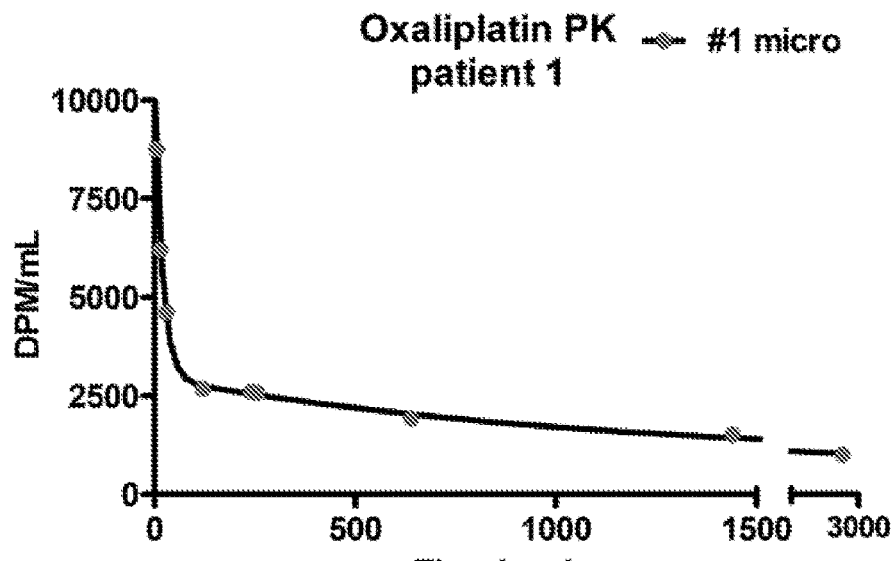
FIG. 17 shows the results of oxaliplatin microdosing of a metastatic breast cancer patient. (a) Plasma elimination kinetics of oxaliplatin administered as a microdose. (b) Time course for microdose induced oxaliplatin adduct formation in PBMC.

Radiolabeled oxaliplatin containing $C^{14}$ carbon atoms in the cyclohexane ring was formulated for human use as a sterile, pyrogen free solution at 0.5 mg/mL in water. This reagent was found to be stable upon storage at −20° C. (<2% loss of radiopurity per year) and stable to free/thaw with no observed precipitation of the drug upon freezing. The microdose was given by IV over 2 minute interval at dose of 1% of the calculated therapeutic dose for this patient and containing 2×10$^6$ DPM/kg body weight of [$^{14}$C]oxaliplatin, corresponding to a specific activity of 11.2 mCi/mM. Unlabeled oxaliplatin and [$^{14}$C]oxaliplatin were mixed just before dosing to achieve the required microdose, and injected through the peripheral vein at one arm. Peripheral blood specimens were drawn into BD Vacutainer CPT' tubes with sodium heparin from the other arm at specific time points before and after the administration of the microdose. Plasma samples collected at −5 min, 5 min, 15 min, 30 min, 2 h, 4 h, 8 h, 24 h, and 48 h post microdose injection were analyzed by liquid scintillation counting (FIG. 17A). An essentially bi-phasic elimination curve was observed, with the first (fast) phase having a $T_{1/2}$ (α) of 13.3 minutes and the second (slow) phase having a $T_{1/2}(\beta)$ of 589 minutes (9.8 hrs). Both of these values are in the middle of the ranges of the corresponding half-lives for oxaliplatin administered at a therapeutic dose (Graham, Martin A., et al. "Clinical pharmacokinetics of oxaliplatin: a critical review." *Clinical Cancer Research* 6.4 (2000): 1205-1218).

Figure 17B:
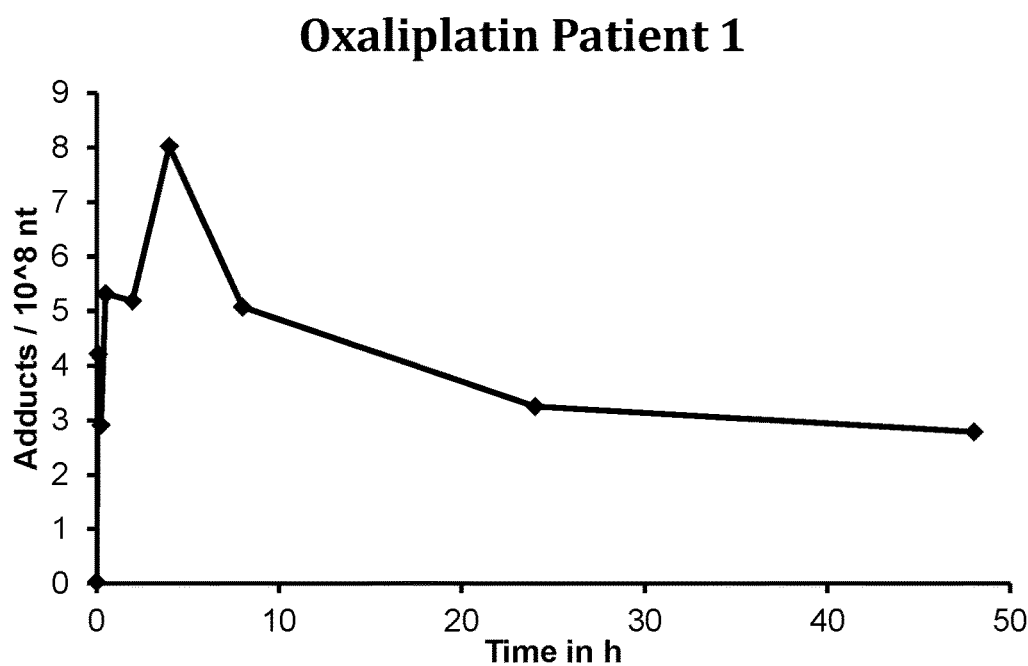
Figure 18A:
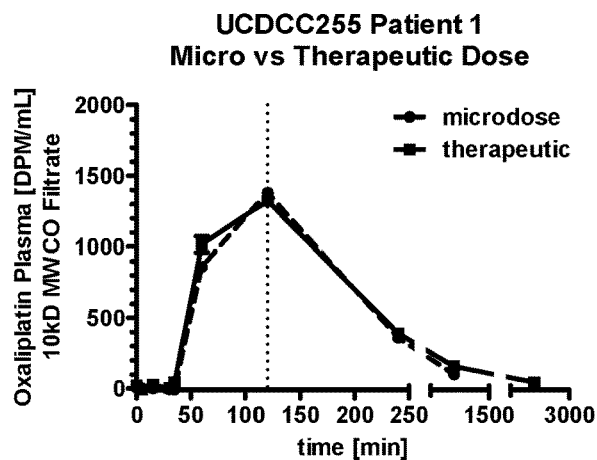
FIG. 18 shows the results of oxaliplatin microdosing of three colon cancer patients. (A, B, &C) Comparision of elimination kinetics of oxaliplatin administered as a microdose or therapeutic dose in three patients. (D, E, &F) Time course for microdose induced oxaliplatin adduct formation in PBMC in these same three colon cancer patients. (G, H, &I) Time course for oxaliplatin adduct formation in PBMC in these same three colon cancer patients after receiving a thereapeutic dose of oxaliplatin.
Figure 18B:
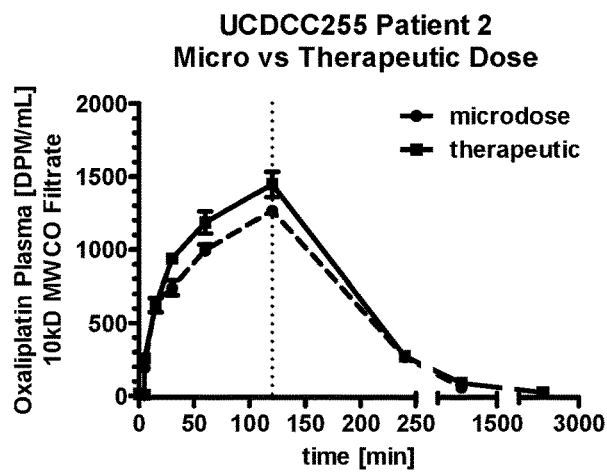
Figure 18C:
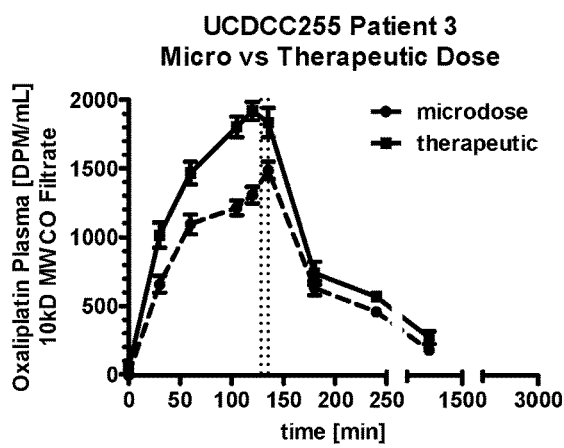
Figure 18D:
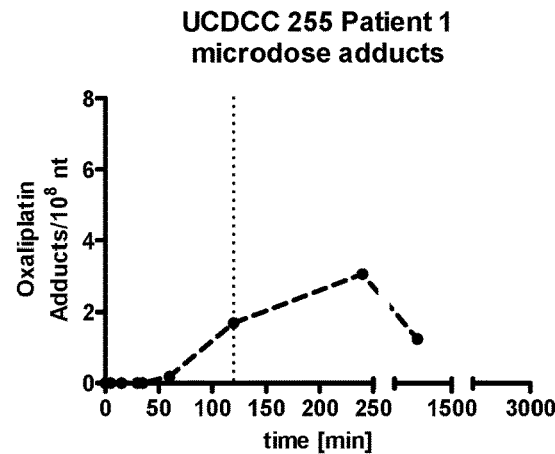
Figure 18E:
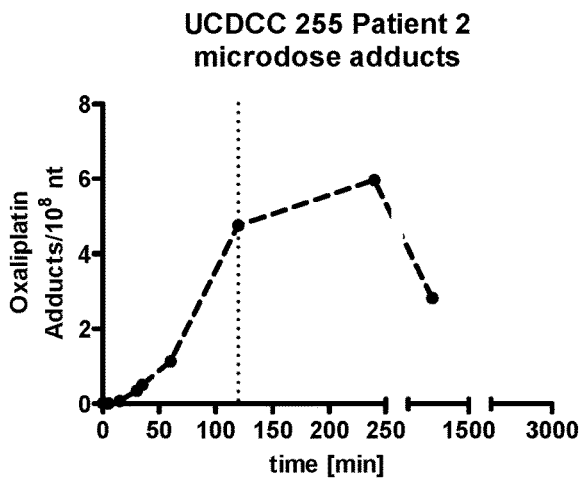
Figure 18F:
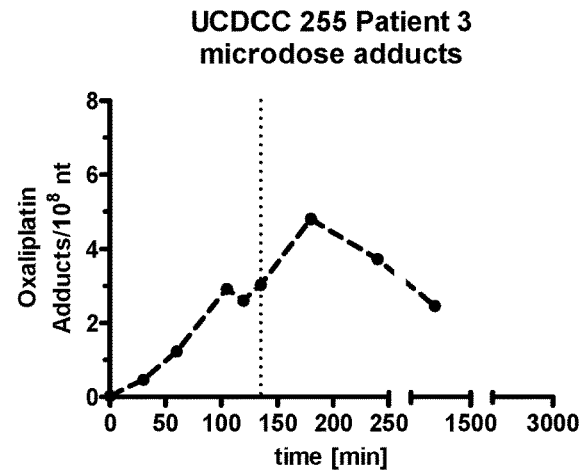
Figure 18G:
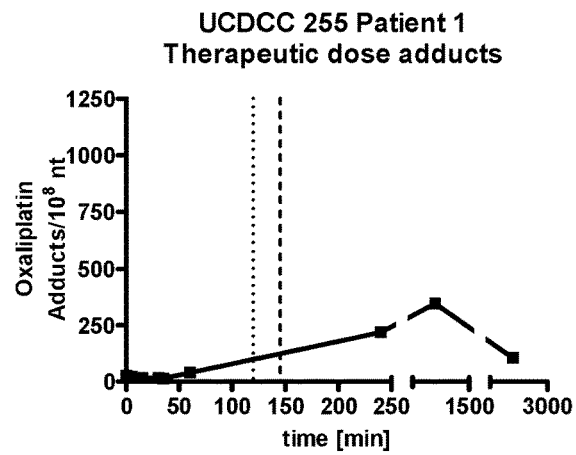
Figure 18H:
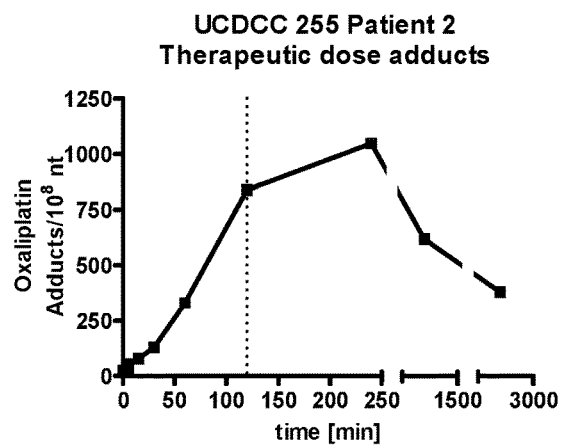
Figure 18I:
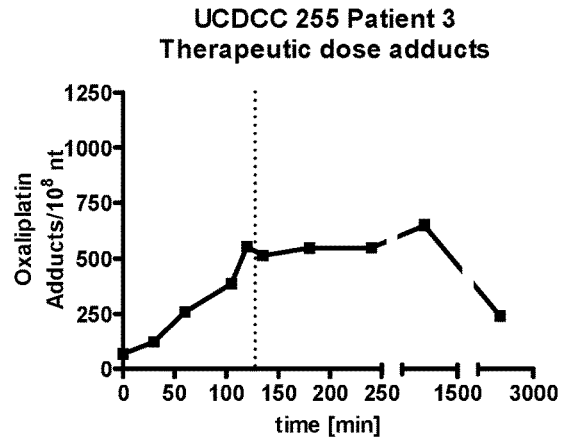

The plasma samples were additionally processed to isolate PBMC, and the DNA was extracted and analyzed using AMS to calculate the oxaliplatin-DNA adduct frequency (both monoadducts and diadducts combined) (FIG. 17B). The [$^{14}$C]oxaliplatin microdose was sufficient to quantitate oxaliplatin-DNA adducts in humans. Oxaliplatin adducts were formed continually during the first 4 hours to a maximum of 8 adducts per $10^8$ nt. These adduct levels then decrease substantially out to 48 hours post microdosing. This finding is consistent with the fast $T_{1/2}$ ($\alpha$) dominating the rate of adduct accumulation in PBMC or that this one patient had a high rate of DNA repair. Compared to the cell culture experiments of Example 11 where the cells were dosed for 24 hours, a smaller oxaliplatin-DNA adduct frequency was observed in the human microdosing experiment, which is again likely due to fast pharmacokinetics limiting the exposure of tissues in vivo compared to the cell culture experiments. Overall, the plasma PK and time course of oxaliplatin-DNA adduct formation and repair in PBMC allowed determination of the best time to dose patients prior to biopsy in order to maximize the oxaliplatin-DNA adduct formation, allow for repair in those patients with high repair capacity, minimize the risk of radioactive contamination of PBMC and tumor samples, and also minimize the risk of radioactive contamination of the operating room by blood-borne radiocarbon. Thus, we identified 48h after administration of the [$^{14}$C]oxaliplatin microdose as an optimal time point for collection of tumor tissue for analysis of oxaliplatin-DNA adducts.

Therefore, a tumor biopsy sample from the bone marrow of this same metastatic breast patient was collected 48 hours post microdose administration and analyzed by AMS for oxaliplatin-DNA adducts. This patient had an oxaliplatin-DNA adduct frequency of 14.6±4.9 (n=2 repeats) per $10^8$ nt. Therefore, in one embodiment, a useful range of oxaliplatin-DNA adduct frequency after microdosing is 0.5-50 adducts per $10^8$ nt.

Similar microdosing and pharmacokinetic studies have been performed using oxaliplatin on locally advanced or metastatic colon cancer patients. These patients are enrolled on an intent to treat basis with a chemotherapy regimen containing 5-florouracil, leucovorin, and oxaliplatin (FOLFOX) according to standard clinical practice. For this study, patients receive an oxaliplatin chemotherapy dose 85 mg/m$^2$ of body surface area using the Du Bois and Du Bois formula by IV over 2 hours. The microdose is also given by IV over 2 hours but at a dose of 1% of the calculated therapeutic dose for each patient and containing $2\times10^6$ DPM/kg body weight of [$^{14}$C]oxaliplatin, corresponding to a specific activity of 11.2 mCi/mM. Three patients also received $2\times10^6$ DPM/kg body weight of [$^{14}$C]oxaliplatin along with their thereapeutic dose of oxaliplatin so that pharmacokinetics of microdose and thereapeutic dose could be compared in each of these patients. Plasma samples were collected, filtered, and counted by liquid scintillation counting to determine plasma oxaliplatin levels. FIGS. 18 A, B, &C show that the pharmacokinetic profiles of the microdose and thereapeutic dose are very similar. The equivalence in plasma PK data suggests that diagnostic microdosing may therefore be useful as a tool to predict PK of therapeutic oxaliplatin for personalized dosing. As shown, there is some residual plasma oxaliplatin at 24 hours post dosing that is lost by 48 hours. FIG. 18 also shows the time course for the formation and loss of oxaliplatin-DNA adducts in PBMC DNA extracted from these patients when they received a microdose (FIGS. 18 D, E, & F) or a thereapeutic (FIGS. 18 G, H, & I) dose of oxaliplatin. The range of microdose-induced adduct levels (frequencies) for the three colorectal patients was 0.1-6 adducts per $10^8$ nt. Overall, these data support the use of 48 hours post oxaliplatin dosing as the optimum time to collect samples for analysis of oxaliplatin-DNA adducts.

Example 13

Safety of [$^{14}$C]oxaliplatin administered as a microdose

The dose of oxaliplatin in the diagnostic microdose was chosen to be sub-toxic and non-therapeutic, to minimize patient chemical and radiation exposure, and to result in AMS measurable oxaliplatin-DNA adducts. Patient toxicity related to the microdose in this above patient was monitored from the time of IV microdose until the patients received their first chemotherapy. The radiolabeled microdose was well tolerated. None of the clinical side effects associated with standard therapeutic doses of oxaliplatin were observed. The radiation exposure due the IV administration of $2.0\times10^6$ DPM/kg of body weight of [$^{14}$C]oxaliplatin is comparable to other diagnostic procedures that are considered safe. The total radioactive dose given to a 75 kg patient after an IV microdose of [$^{14}$C]oxaliplatin is calculated to be 68 µci. Using an exposure of 84 hours (5 half-lives×16.8 hours=84 hours), this conservatively calculates to a total patient radiation exposure of $7.8\times10^{-5}$ joules/kg, which is approximately 0.08 mSv. The annual effective radiation dose equivalent from natural internal sources is 1.6 mSv per person. The radiation exposure for an abdominal CT scan is 10 mSv. The radiation exposure to 14C from administration of this microdose diagnostic reagent is 0.08 mSv÷10 mSv=0.8% of an abdominal CT scan, which is generally considered as a safe radiation dose for diagnostic procedures.

Example 14

Oxaliplatin Microdose Administration to Cancer Patients and Database Creation

Colon cancer patients will be administered a microdose of [$^{14}$C]oxaliplatin by IV injection. The microdose will comprise a dose of [$^{14}$C] oxaliplatin that is 1% of the therapeutic dose for the patient calculated using the DuBois and DuBois formula. The microdose will comprise around $2.0\times10^6$ DPM/kg of patient bodyweight, corresponding to a specific activity of about 11.2 mCi/mM. A 6 mL blood sample will be obtained immediately prior to IV administration of a oxaliplatin microdose. A second 6 mL blood sample will be taken 48 h after microdose administration, followed by a single biopsy sample. DNA will be isolated from the blood and tumor samples. DNA analysis will be performed by UV spectrophotometry and AMS to determine the frequency of $^{14}$C oxaliplatin-DNA monoadducts in each sample as described herein.

As early as two days after the microdose procedure, but within four weeks, patients will begin oxaliplatin chemotherapy in order to collect patient response and toxicity data. For this study, tumor response and radiographic disease progression is defined as progressive disease using RECIST 1.1 for soft tissue disease or by appearance of two or more new lesions. From this, we will determine if oxaliplatin-DNA monoadducts induced by oxaliplatin microdosing in tumor tissue and peripheral blood mononuclear cells (PBMCs) correlate with an objective therapeutic response to platinum-based chemotherapy. We will also determine if the therapeutic treatment will result in a toxic response or other side effects. Toxic response can be assessed using criteria such as Common Terminology Criteria for Adverse Events (CTCAE).

Statistically, differences between responders and non-responders with respect to oxaliplatin-DNA monoadduct formation will be demonstrated by disproving the null hypothesis that the difference of means of adduct levels between responders and nonresponders do not differ. We will compare the mean level of monoadducts in responders to chemotherapy to that of non-responders using a 2-sample t-test at the 0.05 level (2-sided). If the result is statistically significant, we will consider the use of monoadducts levels in PBMC or tumor tissue feasible for treatment stratification. This will statistically demonstrate a range of clinically useful predictive adduct frequencies that may be used to determine a correlation between adduct frequency and likelihood of response to therapeutic administration of oxaliplatin. The clinically useful adduct frequency range will be between 0.5 and 50 adducts per $10^8$ nucleotides.

The Youden index will be used to estimate an optimal threshold or threshold range differentiating responders from non-responders. This threshold can be the midpoint between the mean level of responders and the mean level of non-responders for normally distributed data with equal variance. This can be used as a threshold adduct frequency above which patients are expected to respond to therapy. The threshold will be in the range of 0.5 and 50 adducts per $10^8$ nucleotides.

Although we have previously determined an optimal time point of tissue or blood collection at 48 hours after microdose administration, the method described herein may also be performed at alternative time points of tissue or blood collection after administration of a microdose, e.g., at a time point from 8-96 hours. The correlation of monoadduct frequency to treatment outcome probability is dependent upon this timepoint.

The dose of the radiolabeled oxaliplatin administered from the microdose formulation may also be adjusted within a range that is non-toxic to the patient, e.g., from 0.1-1% of a therapeutic dose. The correlation of monoadduct frequency to treatment outcome probability is dependent upon the initial dose of the radiolabeled oxaliplatin administered to the patient.

The correlation of adduct frequency with treatment outcome may also depend upon the type of tumor the patient has. The database will distinguish adduct frequency correlations to treatment outcome based on cancer type.

Example 15

Prediction of Therapeutic Outcome in a Patient Administered $^{14}C$ Oxaliplatin Once the adduct frequency correlation with therapeutic outcome is established for the preferred microdose formulation at a preferred time of sample collection after administration for a given tumor type, a non-toxic, in vivo diagnostic assay that predicts patient response to subsequent chemotherapy, and possible toxic response will be performed.

Cancer patients will be administered a microdose of $[^{14}C]$ oxaliplatin by IV injection. The microdose will comprise a dose of $[^{14}C]$ oxaliplatin that is 1% of the therapeutic dose for the patient calculated using the DuBois and DuBois formula and having a specific activity of about 11.2 mCi/mM. A 6 mL blood sample will be obtained immediately prior to IV administration of a oxaliplatin microdose. A second 6 mL blood sample will be taken 48 h after microdose administration, followed by a single biopsy sample. DNA will be isolated from the blood and tumor samples. DNA analysis will be performed by UV spectrophotometry and AMS to determine the frequency of $^{14}C$ oxaliplatin-DNA monoadducts in each sample as described herein.

The probability that a cancer will respond to subsequent chemotherapy using the patient's personalized drug-DNA adduct frequency measurement will be determined by comparing the adduct frequency with a clinically derived database specific to the microdose formulation, tissue collection time after administration of the microdose formulation, and cancer and/or tissue type analyzed. A report will be issued to a physician and/or patient about the probability for response to the specific chemotherapy so that a decision to use the specific chemotherapy on the patient can be made.

Example 16

Microdose Assay for Chemosensitivity of Bladder Cancer Cell Lines to Gemcitabine In this example, 5637 and 5637R cell lines, which display differential sensitivity to gemcitabine, were treated in culture to a sub therapeutic dose of $[^{14}C]$gemcitabine. The 5637 cell line has an $IC_{50}$ of 0.12 µM for gemcitabine, while the 5637R cell line has an $IC_{50}$ of 1.44 µM for gemcitabine (FIG. 16C). The frequency of gemcitabine molecules incorporated into genomic DNA was assessed by measuring the $^{14}C$ content of DNA extracted from the cultured cells over time by AMS. The level of incorporated gemcitabine, reported as gemcitabine adducts per $10^6$ nucleotides, was found to be predictive of gemcitabine resistance in cell culture.

Figure 19:
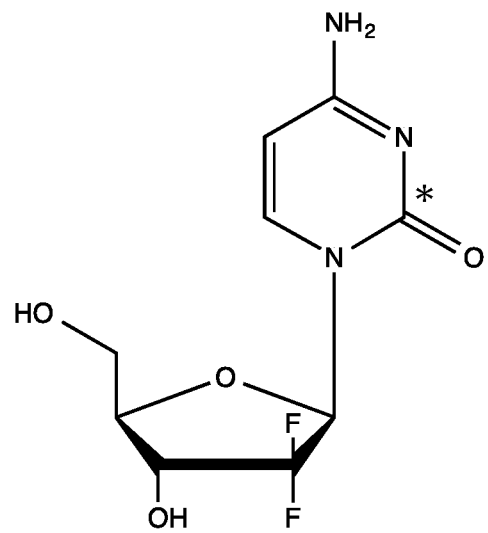
FIG. 19 depicts the structure of radiolabeled gemcitabine (2'-Deoxy-2',2'-difluorocytidine, [cytosine-2-$^{14}$C]-), with the asterisk (*) denoting the location of $^{14}$C.
Figure 20:
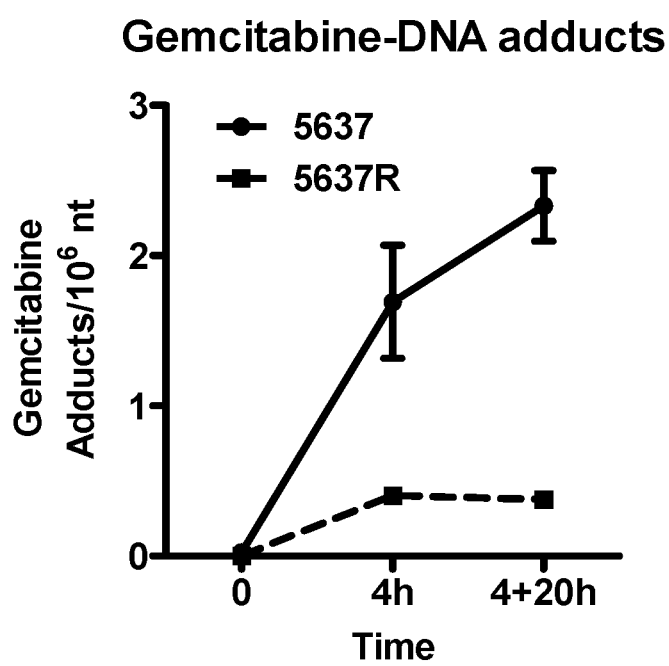
FIG. 20 shows microdose-induced gemcitabine-DNA adducts in cell culture for 5637 and 5637R (gemcitabine resistant) cell lines at 0, 4 and 24 hours after dosing with gemcitabine.
Figure 21A:
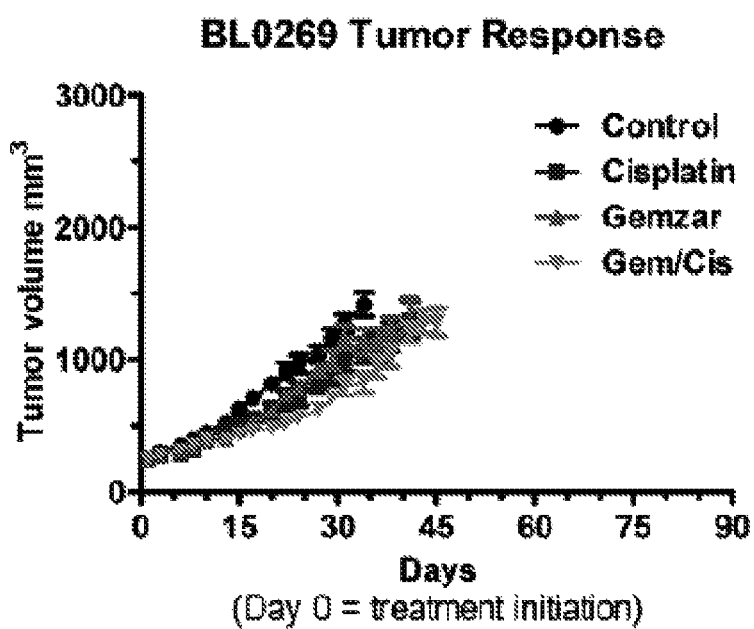
FIG. 21 shows the response of patient derived xenograft tumor growth in NSG mouse models to chemotherapy. A) PDX Model BL0269, B) PDX Model BL0293, C) PDX Model BL0440 and D) PDX Model BL0645. Circles=Vehicle control, Squares=Cisplatin 2 mg/kg IV Q7Dx3, Triangles=gemcitabine 150 mg/kg IP Q7Dx4, Upside down triangles=Cisplatin/gemcitabine combination
Figure 21B:
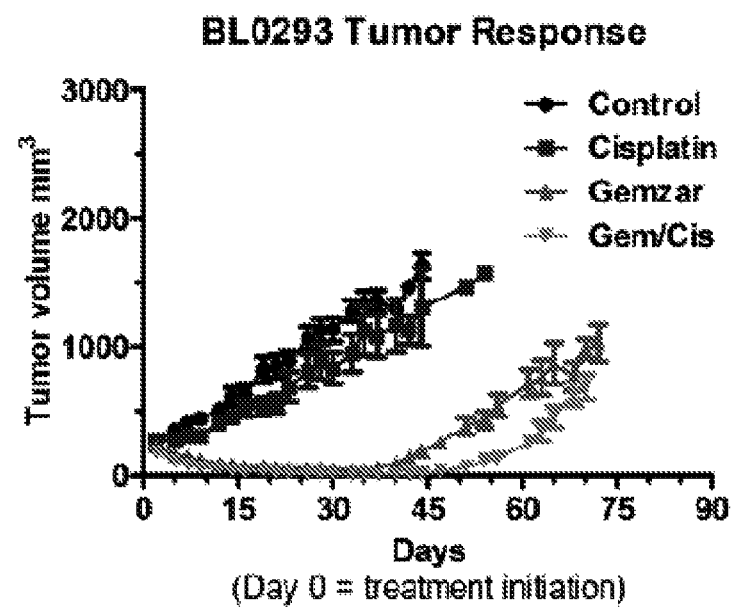
Figure 21C:
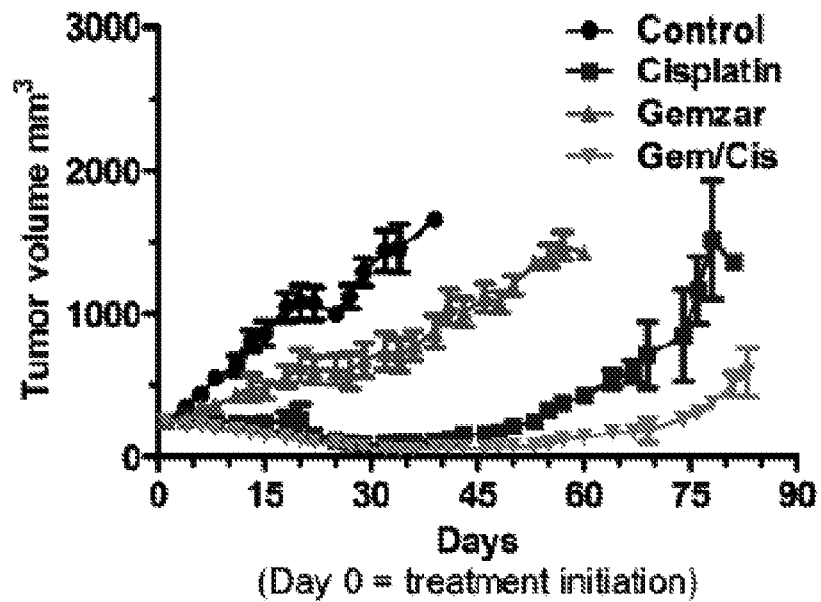
Figure 21D:
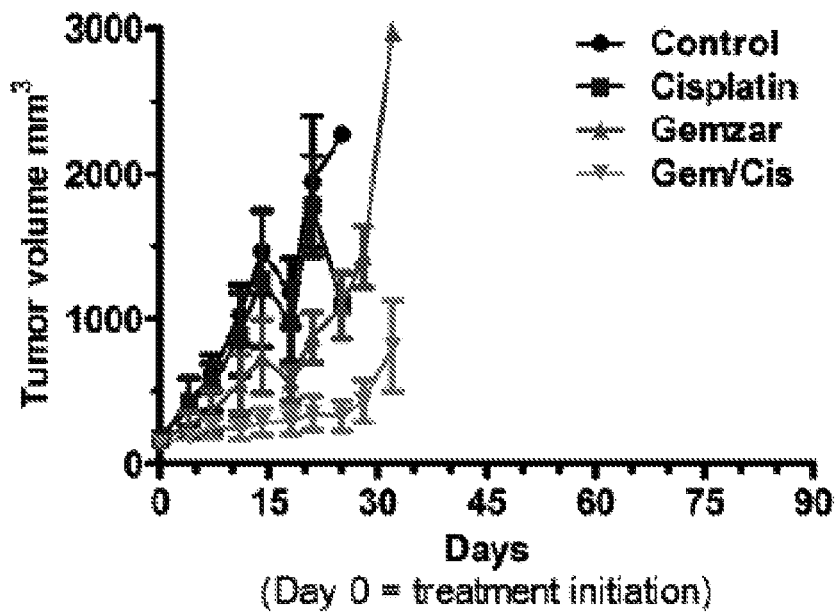

The two cell lines were cultured as described above in Example 11. $[^{14}C]$Gemcitabine (FIG. 19) was labeled at position 2 (on the aromatic nucleobase) with a specific activity of 58.8 mCi/mmol (purchased from Moravek Biochemical). Unlabeled gemcitabine (USP Pharmaceutical Grade) was mixed with the labeled gemcitabine to achieve the correct specific activity for this experiment. Gemcitabine chemotherapy in humans is usually an IV dose of 1000 mg/m$^2$ over 30 minutes, which results in a plasma concentration of about 30µM and a plasma half-life of about 60 minutes. Cells were cultured with $[^{14}C]$gemcitabine at 0.03 µM and 1000 DPM/mL for 4 hours, a subtherapeutic dose with no cytotoxicity. This microdose is approximately 0.1% of a therapeutically relevant concentration. Cells were sampled for DNA extraction and AMS analysis of $^{14}C$ in DNA over 24 hours. There was a time-dependent increase in gemcitabine incorporation into DNA during the 4-hour incubation in both cell lines. At all time points, the gemcitabine incorporation levels in 5637R cells were always lower than the incorporation levels in chemosensitive 5637 cells (FIG. 20). At 24 hours, 5637R cells had much lower gemcitabine incorporation than the parental 5637 cells. Cleary, subtherapeutic dosing with gemcitabine results in measurable adducts, whose levels are indicative of gemcitabine cytotoxicity in cell culture. This result is important because it demonstrates the feasibility of microdose-based diagnostics for a completely different class of drugs than the platinum-based alkylating agents, and that a very low diagnostic dose is feasible (0.1% of the therapeutic dose).

Example 17

Gemcitabine Microdose Administration to Cancer Patients and Database Creation

Cancer patients will be administered a microdose of [$^{14}$C] gemcitabine by IV injection. The microdose will comprise a concentration of [$^{14}$C] gemcitabine that is 1% of the therapeutic dose for the patient. The microdose will comprise around $8.3 \times 10^4$ DPM/kg of patient bodyweight, corresponding to a specific activity of about 1.5 mCi/mM. A 6 mL blood sample will be obtained immediately prior to IV administration of a gemcitabine microdose. A second 6 mL blood sample will be taken 24 h after microdose administration, followed by a single biopsy sample. DNA will be isolated from the blood and tumor samples. DNA analysis will be performed by UV spectrophotometry and AMS to determine the frequency of $^{14}$C gemcitabine-DNA monoadducts in each sample as described herein.

As early as two days after the microdose procedure, but within four weeks, patients will begin gemcitabine chemotherapy in order to collect patient response and toxicity data. For this study, tumor response and radiographic disease progression is defined as progressive disease using RECIST 1.1 for soft tissue disease or by appearance of two or more new lesions. From this, we will determine if gemcitabine-DNA monoadducts induced by gemcitabine microdosing in tumor tissue and peripheral blood mononuclear cells (PBMCs) correlate with an objective response to platinum-based chemotherapy.

Statistically, differences between responders and non-responders with respect to gemcitabine-DNA monoadduct formation will be demonstrated by disproving the null hypothesis that the difference of means of adduct levels between responders and nonresponders do not differ. We will compare the mean level of monoadducts in responders to chemotherapy to that of non-responders using a 2-sample t-test at the 0.05 level (2-sided). If the result is statistically significant, we will consider the use of monoadducts levels in PBMC or tumor tissue feasible for treatment stratification. This will statistically demonstrate a range of clinically useful predictive adduct frequencies that may be used to determine a correlation between adduct frequency and likelihood of response to therapeutic administration of gemcitabine. The clinically useful adduct frequency range will be between 0.5 and 50 adducts per $10^8$ nucleotides.

The Youden index will be used to estimate the optimal cut-point differentiating responders from non-responders. This cut-point is the midpoint between the mean level of responders and the mean level of non-responders (28) for normally distributed data with equal variance. This may be used as a threshold adduct frequency above which patients are expected to respond to therapy. The threshold will be in the range of 0.5 and 50 adducts per $10^8$ nucleotides.

Although we have previously determined an optimal time point of tissue or blood collection at 24 hours after microdose administration, the method described herein may also be performed at alternative time points of tissue or blood collection after administration of a microdose, e.g., at a time point from 4-48 hours. The correlation of monoadduct frequency to treatment outcome probability is dependent upon this timepoint.

The dose of the radiolabeled gemcitabine administered in the microdose formulation may also be adjusted within a range that is non-toxic to the patient, e.g., from 0.1-10% of a therapeutic dose. The correlation of monoadduct frequency to treatment outcome probability is dependent upon the initial dose of the radiolabeled gemcitabine administered to the patient.

The correlation of adduct frequency with treatment outcome may also depend upon the type of tumor the patient has. The database will distinguish adduct frequency correlations to treatment outcome based on cancer type.

Example 18

Prediction of Therapeutic Outcome in a Patient Administered $^{14}$C gemcitabine Once the adduct frequency correlation with therapeutic outcome is established for preferred microdose formulation at a preferred time of sample collection after administration for a given tumor type, a non-toxic, in vivo diagnostic assay that predicts patient response to subsequent chemotherapy, and possible toxic response will be performed.

Cancer patients will be administered a microdose of [$^{14}$C]gemcitabine by IV injection. The microdose will comprise a dose of [$^{14}$C]gemcitabine that is 1% of the therapeutic dose for the patient. The microdose will comprise around $8.0 \times 10^4$ DPM/kg of patient bodyweight, corresponding to a specific activity of about 1.5 mCi/mM in the microdose formulation. A 6 mL blood sample will be obtained immediately prior to IV administration of a gemcitabine microdose. A second 6 mL blood sample will be taken 24 h after microdose administration, followed by a single biopsy sample. DNA will be isolated from the blood and tumor samples. DNA analysis will be performed by UV spectrophotometry and AMS to determine the frequency of $^{14}$C gemcitabine-DNA monoadducts in each sample as described herein.

The probability that a cancer will respond to subsequent chemotherapy using the patient's personalized drug-DNA adduct frequency measurement will be determined by comparing the adduct frequency with a clinically derived database specific to the microdose formulation, tissue collection time after administration of the microdose formulation, and cancer and/or tissue type analyzed. A report will be issued to a physician and/or patient about the probability for response to the specific chemotherapy so that a decision to use the specific chemotherapy on the patient can be made.

Example 19

Microdose Diagnostic Efficacy in the PDX Mouse Model

Patient derived tumor xenographs (PDX) are created by implanting cancerous tissue from a patient's primary tumor directly into an immunodeficient mouse. Tumor fragments obtained by mechanically sectioning the tumor into smaller fragments are believed to retain cell-cell interactions as well as some tissue architecture of the original tumor, therefore better mimicking the tumor microenvironment. The NSG mouse (Nod-Scid Gamma severe combined immunodeficient mouse) is commercially available and commonly used for PDX models because it is considered one of the most immunodeficient mouse strains that lacks mature T and B cells and also is unable produce natural killer cells. In this example, we report on four PDX mouse models created from primary bladder cancer tissues in NSG mice, each having different sensitivities to gemcitabine/cisplatin (G/C) combination therapy commonly used to treat bladder cancers. In these experiments, drug sensitivity was determined by measuring tumor growth in the PDX models while the mice received chemotherapy consisting of the individual drugs alone or in combination. We show 1) that different PDX tumors can be insensitive to both drugs, sensitive to one drug alone, simultaneously sensitive to both drugs, or display sensitivity only to the combination of drugs (synergistic efficacy), 2) that the levels of microdosed induced carboplatin-DNA monoadducts in the different PDX models are correlated to cisplatin sensitivity, 3) that the levels of microdose induced gemcitabine incorporation (expressed as gemcitabine-DNA adducts) in the different PDX models are correlated to gemcitabine sensitivity, and 4) that the levels of carboplatin-DNA monoadducts and the levels of gemcitabine-DNA adducts both increase in a PDX model that exhibits synergistic efficacy upon exposure to gemcitabine/carboplatin (G/Carbo) combination treatment. This synergistic effect is seen both when the combination treatment is administered as a chemotherapeutic dose or as a diagnostic microdose.

Methods

Unlabeled gemcitabine (USP Pharmaceutical Grade) was obtained from Eli Lilly (Indianapolis, Ind., USA), and unlabeled carboplatin (USP Pharmaceutical Grade) from Hospira (Lake Forest, Ill., USA). [$^{14}$C] labeled carboplatin (specific activity 53 mCi/mmol) and gemcitabine (specific activity 58.8 mCi/mmol) were obtained from Moravek Biochemicals (Brea, Calif., USA). Mixtures of [$^{14}$C] labeled and unlabeled drug were used to minimize the usage of radiocarbon and achieve the different specific activities required for microdoses and therapeutic doses. Drug solutions for the indicated experiments were prepared immediately before use.

Female NSG mice (5-8 weeks of age, body weight: 20 to 25 g) were obtained from Jackson Laboratories (CA, USA). All animals were kept under pathogen-free conditions and were allowed to acclimatize for at least 4 days prior to any experiments. PDX models bearing the indicated patient derived xenografts were created by subcutaneous injection at the flank of 1 mm$^3$ tumor tissue. To establish multiple PDXs to allow efficacy studies with multiple drugs, PDXs from passage 2-4 were minced into 1 mm$^3$ sections and injected subcutaneously into multiple mice. At least 3 mice were used for each treatment group. Tumors were allowed to grow to at about 100 mm$^3$ before being assessed for drug sensitivity or the induction of DNA adducts by the administration of a microdose or a therapeutic dose of labeled drug. To assess tumor response to chemotherapy, cisplatin was administered at 2 mg/kg IV every 7 days for a total of 3 cycles, or gemcitabine was administered at 150 mg/kg IP every 7 days for a total of 4 cycles. G/C combination chemotherapy consisted of the simultaneous administration of both drugs using the schema described above. Tumor growth was assessed by measuring palpable tumors with a caliper and calculating tumor volume. Drug-DNA adduct frequencies were measured in tumor tissue collected 24 hours after intravenous injection of labeled drug and stored at −80° C. until DNA isolation. DNA was isolated using a modified Wizard procedure (Promega), quantitated by spectrophotometry, and then stored frozen at −20° C. until AMS analysis. Ten micrograms of DNA per sample was converted to graphite and measured by AMS for 14C quantification as previously described.

All experiments were carried out at least in triplicate in order to enable statistically significant comparisons of the results. All results are expressed as the mean±standard error of the mean (SEM) unless otherwise noted. Statistical analyses were performed using GraphPad Prism™ software (GraphPad Software Inc., CA, USA) and included two-tailed Student's t-test or one-way ANOVA followed by Bonferroni's multiple comparison test of selected pairs of columns. A value of $p<0.05$ was considered statistically significant. For in vivo experiments, animals were unbiasedly assigned into different treatment groups. No formal randomization was used in any experiment. Group allocation and outcome assessment was not performed in a blinded manner. No animals or samples were excluded from data analysis.

Chemotherapy Sensitivity of Four Bladder Cancer PDX Models

Primary tumor tissue from four bladder cancer patients were implanted in NSG mice to create the PDX models described in Table 5. When the tumor xenographs had grown to about 100-200 mm$^3$, each of the PDX models were subjected to chemotherapy to assess sensitivity to either gemcitabine or cisplatin as single agents, and also to G/C combination chemotherapy (FIG. 21). Of the four distinct tumors tested in the PDX model, three were resistance to cisplatin (BL0269, BL0293, BL0645) and two were resistance to gemcitabine (BL0269, BL0645) as single agent therapies. Platinum agents in combination with gemcitabine are known to achieve additive and sometimes synergistic anti-tumor activity. The PDX models constructed here were more sensitive to the combination therapy than the single agent therapy, with PDX model BL0645 showing synergistic anti-tumor activity. These PDX models show that chemoresistance to one drug could be overcome by the other drug (BL0293, BL0440), or the combination of both drugs (BL0645).

TABLE 5

Primary tumor tissue from four bladder cancer patients characterization

| PDX | Patient | | Tumor | | Tumor | Xenograph Sensitivity | |
|---|---|---|---|---|---|---|---|
| Model # | Sex | Age | Site | Diagnosis | Type | Cisplatin | Gemcitabine |
| BL0269 | M | 58 | Bladder | Urothelial Carcinoma | Invasive | RES | RES |
| BL0293 | F | 77 | Bladder | Urothelial Carcinoma | Invasive | RES | SEN |
| BL0440 | M | 71 | Bladder | Urothelial Carcinoma | ND | SEN | SEN |

TABLE 5-continued

Primary tumor tissue from four bladder cancer patients characterization

| PDX Model # | Patient Sex | Age | Tumor Site | Diagnosis | Tumor Type | Xenograph Sensitivity Cisplatin | Gemcitabine |
|---|---|---|---|---|---|---|---|
| BL0645 | F | 75 | Bladder | Urothelial Carcinoma | Invasive | RES SEN(G/C) | RES SEN(G/C) |

Figure 22A:
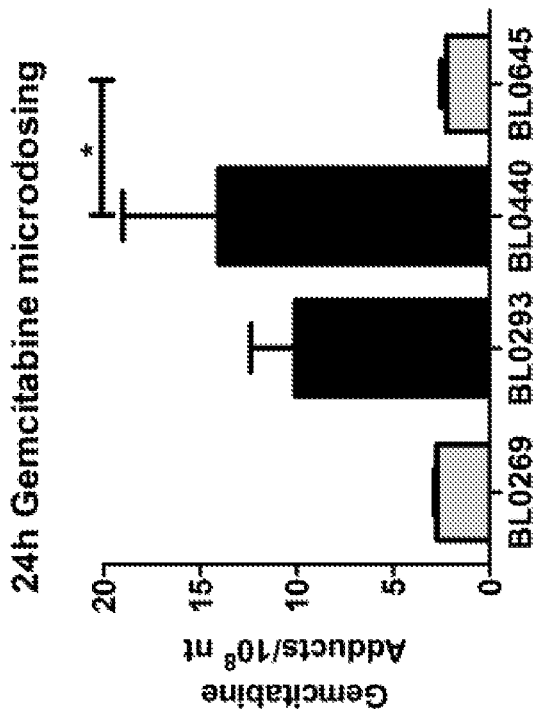
FIG. 22 shows microdose-induced carboplatin and gemcitabine DNA-adduct levels in drug sensitive (BL0440 for carboplatin, BL0293 and BL0440 for gemcitabine) and drug resistant (BL0269, BL0293, and BL0645 for carboplatin, BL0269 and BL0645 for gemcitabine) PDX models. Animals were dosed via tail vein injection with A) 0.375 mg/kg carboplatin, 50,000 dpm/g or B) 0.092 mg/kg gemcitabine, 1000 dpm/g. Data shown is from DNA isolated from tumors collected 24 h after injection of the labeled drug. The upper straight bars indicate statistical differences in adducts levels between sensitive and resistant PDX models (*p<0.05, **p<0.01).
Figure 22B:
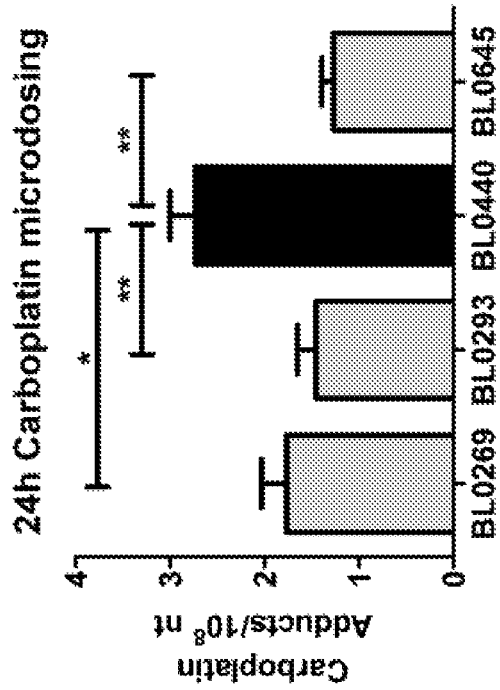

Microdose Induced Carboplatin and Gemcitabine DNA-Adduct Levels Correlate with PDX Drug Sensitivity in NSG Mice NSG mice bearing the indicated PDX tumors were injected with a microdose of $^{14}$C-labeled carboplatin (FIG. 22A) or $^{14}$C-labeled gemcitabine (FIG. 22B). The microdose of $^{14}$C-labeled carboplatin was 0.375 mg/kg carboplatin, 50,000 dpm/g. The microdose of $^{14}$C-labeled gemcitabine was 0.092 mg/kg gemcitabine, 1000 dpm/g. The doses of each drug administered to the mice were chosen to target 1 µM in plasma concentration of carboplatin and 0.3 µM in plasma concentration of gemcitabine. These plasma concentrations represent 1% of the approximate peak plasma concentration during human chemotherapy. Animals were sacrificed after 24 h and drug-DNA adduct frequency was determined from collected tumor tissue by AMS measurements of $^{14}$C in tumor DNA. Carboplatin DNA-adduct levels correlate with PDX model sensitivity to cisplatin at 24h after microdosing (FIG. 22A). Gemcitabine DNA-adduct levels correlate with PDX model sensitivity to gemcitabine at 24 h after microdosing (FIG. 22B). The cisplatin and gemcitabine sensitive bladder cancer PDX model BL0440 shows higher mean carboplatin-DNA monoadduct frequencies compared to the cisplatin resistant models. At 24 hours, BL0440 tumor DNA exhibits a significant higher mean carboplatin-DNA monoadduct level than BL0269, BL0293 and BL0645 (2.73±0.661 versus 1.77±0.706, 1.46±0.520, and 1.27±0.307 adducts per $10^8$ nucleotides, respectively, p<0.05 and p<0.01) (FIG. 22A). There is no significant difference in carboplatin-DNA monoadduct levels between the three resistant PDX models. In addition, administration of a microdose of gemcitabine shows that the two gemcitabine sensitive PDX models BL0293 and BL0440 display higher gemcitabine adduct levels than the resistant PDX models BL0269 and BL0645 (10.0±5.92, 13.1±10.2 versus 3.17±0.278 and 2.44±0.880, respectively, p<0.05 and <0.01). We conclude that microdose induced carboplatin-DNA monoadducts predicts sensitivity to cisplatin chemotherapy, and microdose induced gemcitabine incorporation predicts sensitivity to gemcitabine chemotherapy.

Figure 23A:
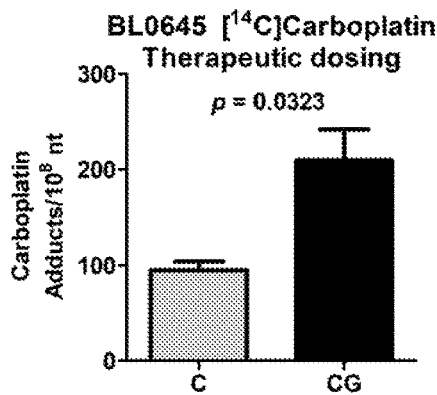
FIG. 23 shows microdosed induced adduct frequency in a synergetic PDX model upon exposure to combination therapy given at either therapeutic or microdose concentrations. C=carboplatin single agent treatment; G=gemcitabine single agent treatment; GC or CG=gemcitabine/carboplatin combination treatment. A) Therapeutic treatment of BL0645 consisting of [$^{14}$C]carboplatin (37.5 mg/kg, 50,000 dpm/g) alone or in combination with gemcitabine (9.2 mg/kg). B) Therapeutic treatment of BL0645 consisting of [$^{14}$C]gemcitabine (9.2 mg/kg, 1000 dpm/g) alone or in combination with carboplatin (37.5 mg/kg). C) Microdose treatment of BL0645 consisting of [$^{14}$C]carboplatin (0.375 mg/kg, 50,000 dpm/g) alone or in combination with gemcitabine (0.092 mg/kg). D) Microdose treatment of BL0645 consisting of [$^{14}$C]gemcitabine (0.092 mg/kg, 1000 dpm/g) alone or in combination with carboplatin (0.375 mg/kg). E) Microdose treatment of BL0269 consisting of [$^{14}$C]carboplatin (0.375 mg/kg, 50,000 dpm/g) alone or in combination with gemcitabine (0.092 mg/kg). F) Microdose treatment of BL0269 consisting of [$^{14}$C]gemcitabine (0.092 mg/kg, 1000 dpm/g) alone or in combination with carboplatin (0.375 mg/kg).
Figure 23B:
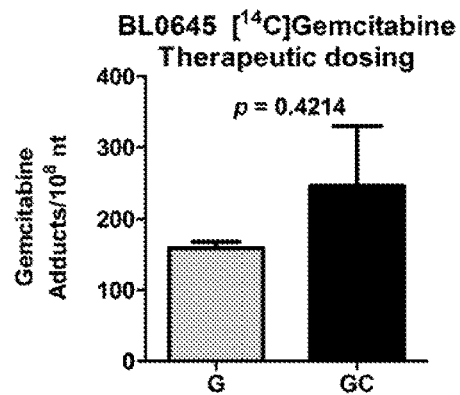
Figure 23C:
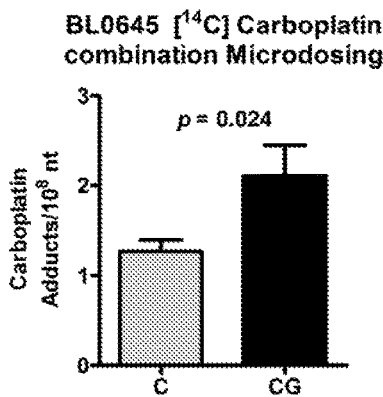
Figure 23D:
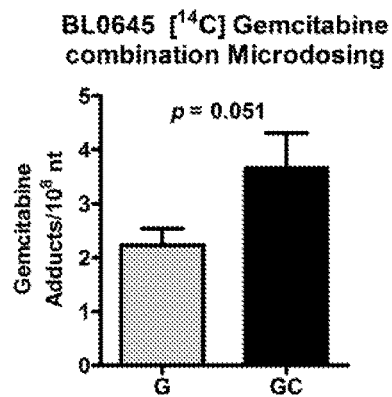
Figure 23E:
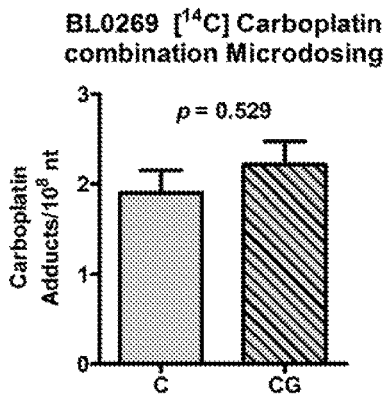
Figure 23F:
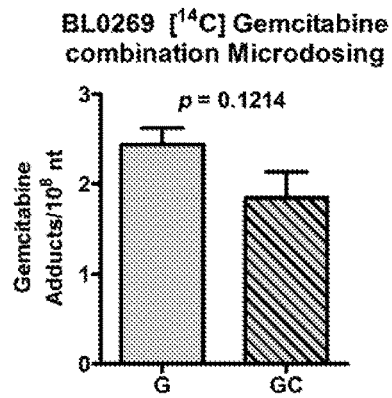

Enhancement of Drug-DNA Adduct Frequency by Combination Chemotherapy in a Synergetic Sensitive PDX Model The PDX model BL0645 shows treatment resistance towards each of the single agents, cisplatin and gemcitabine, but sensitivity toward G/C combination therapy. In this example we test whether gemcitabine/carboplatin (G/Carbo) combination therapy has an effect on the formation of drug-DNA adducts in this synergistic tumor model. In FIG. 23A, NGS mice bearing BL0645 xenographs were administered via tail vein injection a therapeutic dose of [$^{14}$C] carboplatin alone or a therapeutic dose of [$^{14}$C]carboplatin in combination with a therapeutic dose of gemcitabine. Carboplatin-DNA monoadducts were measured in tumor tissue 24 h after dosing. A therapeutic dose of the combination [$^{14}$C]carboplatin plus unlabeled gemcitabine leads to a significant increase in carboplatin-DNA monoadduct level (94.84±16.02 versus 209.6±64.66 adducts per $10^8$ nucleotides, p=0.032) compared to treatment with carboplatin alone. In FIG. 23B, the same experiment was conducted in which the mice received a therapeutic dose of [$^{14}$C]gemcitabine alone or a therapeutic dose of [$^{14}$C]gemcitabine in combination with a therapeutic dose of unlabeled carboplatin. The combination treatment of therapeutic doses of [$^{14}$C]gemcitabine with unlabeled carboplatin increases gemcitabine adduct level (169.2±9.129 versus 268.1±182.8 adducts per $10^8$ nucleotides) compared to gemcitabine alone. We repeated the experiment of FIGS. 23A and B to see if a combination diagnostic microdose treatment also leads to increased formation of drug-DNA adducts. FIGS. 23C and D show [$^{14}$C]carboplatin or [$^{14}$C]gemcitabine induced DNA adduct levels of tumor model BL0645 after microdoses of single drug or G/Carbo combination. Simultaneous exposure of BL0645 tumors to microdoses of both drugs lead to an increase in mean carboplatin-DNA monoadducts after 24 h (1.27±0.307 versus 2.10±0.596 adducts per $10^8$ nucleotides, p=0.024, FIG. 23C) and gemcitabine adducts (2.44±0.880 versus 3.98±1.22 adducts per $10^8$ nucleotides, p=0.051, FIG. 23D) compared to single agent frequencies. To confirm the observation that combination therapy synergy leads to enhanced levels of microdose induced drug-DNA adduct levels, a control experiment was conducted with PDX model BL0269, which is resistant to both single agent and combination therapy. FIGS. 23E and 23F show [$^{14}$C]carboplatin or [$^{14}$C]gemcitabine induced DNA adduct levels of tumor model BL0269 after diagnostic microdoses of single drug or G/Carbo combination. In contrast to the results with the synergistic PDX model, BL0269 shows no increase in adduct formation when treated with a diagnostic microdose of G/Carbo combination, compared to single agent microdose treatment. Carboplatin-DNA monoadduct levels were not significantly different (1.85±0.798 versus 2.22±0.442 adducts per $10^8$ nucleotides, p=0.529) between the single agent and combination (G/Carbo) microdose treatments (FIG. 23E). Similarly, gemcitabine-DNA adduct levels showed no significant change (2.44±0.492 versus 1.85±0.492 adducts per $10^8$ nucleotides, p=0.121) between treatment groups (FIG. 23F).

The observation that diagnostic microdosing leads to increased drug-DNA adduct formation when given as a combination of drug products shows that the diagnostic assay of the instant invention can predict enhanced tumor response to the synergistic effects of combination therapy.

Dose linearity between the diagnostic microdose and the chemotherapeutic treatment dose is also demonstrated in this set of experiments for the PDX mouse model. By comparing FIGS. 23A and B with FIGS. 23C and D, there is approximately 100-fold difference in drug-DNA adduct formation when a 100-fold difference in drug concentration was administered.

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method of screening a cancer patient for treatment with oxaliplatin, comprising:
    administering a diagnostic reagent comprising a patient dose of a microdose formulation of a radiolabeled oxaliplatin to a patient, wherein said radiolabeled oxaliplatin binds to the DNA of said patient to form a DNA-oxaliplatin adduct;
    obtaining a tumor tissue sample from said patient about 36-72 hours after said administration, wherein said sample comprises said DNA-oxaliplatin adduct;
    measuring a frequency of said DNA-oxaliplatin in said sample; and
    comparing said frequency with a first predetermined threshold.

2. The method of claim 1, further comprising administering oxaliplatin to said patient based on said comparison of said DNA-drug adduct frequency with said first predetermined threshold.

3. The method of claim 1, further comprising administering oxaliplatin to said patient if said DNA-drug adduct frequency is above said first predetermined threshold.

4. The method of claim 3, further comprising administering oxaliplatin to said patient if said DNA-drug adduct frequency is below a second predetermined threshold, wherein said second predetermined threshold is indicative of drug toxicity.

5. The method of claim 1, wherein said microdose formulation is administered to a patient at a dose of 10% or less, 1% or less, or 0.1% or less of a therapeutic dose of oxaliplatin.

6. The method of claim 1, wherein said radiolabel is $^{14}C$ or $^{3}H$.

7. The method of claim 1, wherein said comparison provides a likelihood of responsiveness to a therapeutic dose of oxaliplatin based on said DNA-drug adduct frequency.

8. The method of claim 1, wherein said DNA drug adduct comprises a monoadduct or a diadduct or both.

9. The method of claim 8, wherein the patient dose of said microdose formulation comprises $1 \times 10^6$ to $10 \times 10^6$ DPM/kg body weight of [$^{14}C$]oxaliplatin, and wherein said DNA-drug adduct frequency is between 0.5 and 50 per $10^8$ nucleotides.

10. A method of screening a cancer patient for combination chemotherapy treatment, comprising:
    administering a diagnostic reagent comprising a microdose formulation of a plurality of chemotherapeutic drugs to a patient, wherein at least one of said plurality of chemotherapeutic drugs is radiolabeled oxaliplatin and binds to the DNA of said patient to form a DNA-oxaliplatin adduct;
    obtaining a tumor tissue sample from said patient about 36-72 hours after said administration, wherein said sample comprises said DNA-oxaliplatin adduct;
    measuring a frequency of said DNA-oxaliplatin adduct in said sample; and
    comparing said frequency with a first predetermined threshold.

11. The method of claim 1, wherein said tumor tissue sample is obtained from said patient about 48 hours after said administration of said microdose formulation to said patient.

* * * * *